(12) United States Patent
Yoo et al.

(10) Patent No.: US 11,896,609 B2
(45) Date of Patent: Feb. 13, 2024

(54) PHARMACEUTICAL COMPOSITION FOR TREATING INFLAMMATORY DISEASES COMPRISING GERMANIUM TELLURIDE NANOSHEETS COATED WITH POLYVINYLPYRROLIDONE

(71) Applicant: Industry-Academic Cooperation Foundation, Seoul (KR)

(72) Inventors: Kyung-Hwa Yoo, Seoul (KR); Jun Ho Song, Seodaemun-gu (KR); Yong-Beom Park, Seocho-gu (KR); Sun-Mi Lee, Gangseo-gu (KR); Chin Hee Mun, Gyeonggi-do (KR); Taejun Yoon, Seodaemun-gu (KR)

(73) Assignee: Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 17/893,937

(22) Filed: Aug. 23, 2022

(65) Prior Publication Data

US 2023/0080524 A1 Mar. 16, 2023

(30) Foreign Application Priority Data

Aug. 24, 2021 (KR) .................. 10-2021-0111826

(51) Int. Cl.
| | | |
|---|---|---|
| A61K 33/24 | (2019.01) | |
| A61K 9/00 | (2006.01) | |
| A61K 9/28 | (2006.01) | |
| A61K 9/51 | (2006.01) | |
| A61K 33/00 | (2006.01) | |
| A61K 33/04 | (2006.01) | |
| A61P 1/04 | (2006.01) | |
| A61P 29/00 | (2006.01) | |
| A61P 37/00 | (2006.01) | |
| A61K 47/32 | (2006.01) | |

(52) U.S. Cl.
CPC ............ *A61K 33/24* (2013.01); *A61K 9/0029* (2013.01); *A61K 9/0056* (2013.01); *A61K 9/284* (2013.01); *A61K 9/5115* (2013.01); *A61K 33/00* (2013.01); *A61K 33/04* (2013.01); *A61P 1/04* (2018.01); *A61P 29/00* (2018.01); *A61P 37/00* (2018.01); *A61K 47/32* (2013.01)

(58) Field of Classification Search
CPC .... A61K 33/24; A61K 9/0029; A61K 9/0056; A61K 9/284; A61K 47/32; A61K 9/5115; A61K 33/00; A61K 33/04; A61P 1/00; A61P 29/00; A61P 37/00
See application file for complete search history.

(56) References Cited

U.S. PATENT DOCUMENTS 9,492,805 B2 * 11/2016 Gleason .................. B01J 13/04

FOREIGN PATENT DOCUMENTS

WO WO-2014104617 A1 * 7/2014 ........... A61N 1/0436

OTHER PUBLICATIONS

Buck, Matthew R., et al. "Polymer-assisted synthesis of colloidal germanium telluride nano-octahedra, nanospheres, and nanosheets." Chemistry of Materials 25.10 (2013): 2163-2171. (Year: 2013).*
Song, Jun Ho, et al. "GeTe nanosheets as theranostic agents for multimodal imaging and therapy of inflammatory bowel disease." Advanced Functional Materials 32.2 (2022): 2107433. (Year: 2022).*
Zamora, R., Vodovotz, Y. & Billiar, T.R. Inducible Nitric Oxide Synthase and Inflammatory Diseases. Mol Med 6, 347-373 (2000). (Year: 2000).*
Pesce JT, Ramalingam TR, Mentink-Kane MM, Wilson MS, El Kasmi KC, Smith AM, Thompson RW, Cheever AW, Murray PJ, Wynn TA. Arginase-1-expressing macrophages suppress Th2 cytokine-driven inflammation and fibrosis. PLoS Pathog. Apr. 2009;5(4):e1000371 (Year: 2009).*

* cited by examiner

*Primary Examiner* — Abigail VanHorn
(74) *Attorney, Agent, or Firm* — Casimir Jones, S.C.; Robert A. Goetz

(57) ABSTRACT

The present invention relates to a composition for treating inflammatory diseases comprising germanium telluride nanosheets coated with polyvinylpyrrolidone, and the nanosheets have excellent anti-inflammatory and thus are excellent in treating inflammatory bowel disease and psoriasis.

7 Claims, 45 Drawing Sheets

| Average | 1.3 | 4.8 | 4.5 | 2.0 |

PHARMACEUTICAL COMPOSITION FOR TREATING INFLAMMATORY DISEASES COMPRISING GERMANIUM TELLURIDE NANOSHEETS COATED WITH POLYVINYLPYRROLIDONE

CROSS-REFERENCE TO RELATED APPLICATION

This application claims priority to and the benefit of Korean Patent Application No. 10-2021-0111826, filed on Aug. 24, 2021, the disclosure of which is incorporated herein by reference in its entirety.

BACKGROUND

1. Field of the Invention

The present invention relates to a pharmaceutical composition for treating inflammatory diseases comprising germanium telluride nanosheets coated with polyvinylpyrrolidone and a method for treating inflammatory diseases using the same.

2. Discussion of Related Art

Inflammatory bowel disease (IBD), also known as ulcerative colitis (UC) and Crohn's disease (CD), is a chronic disease, in which recurrence and exacerbation are repeated, thus not only worsening the patient's quality of life but also increasing the risk of developing colorectal cancer 2- to 8-fold (Non-Patent Documents 1 and 2). Although examples of traditional therapeutic agents for IBD include arsenal, aminosalicylate, steroids, immunosuppressants (cyclosporine, azathioprine, and 6-mercaptopurine), and the like, it is difficult to use these therapeutic agents due to serious side effects. Further, since currently used IBD therapeutic agents have serious side effects when used in high doses, there is a need for an effective IBD therapeutic agent capable of being safely used. Since inflammatory bowel disease and colorectal cancer are diseases of the digestive system, the side effects of therapeutic agents can be reduced only when the therapeutic agents can be orally administered.

Meanwhile, globally, cancer incidence and mortality are increasing every year. There are various types of cancer therapeutic agents, from traditionally used cytotoxic anticancer agents to recently developed targeted anticancer agents. Existing cytotoxic anticancer agents affect not only cancer cells but also normal cells to exhibit systemic toxicity and cytotoxicity, thereby causing various side effects. In order to overcome the limitations of cytotoxic anticancer agents, research and development of monoclonal antibody therapeutic agents that target and kill only cancer cells are continuously being conducted. Examples of monoclonal antibodies that have been approved by the US Food and Drug Administration (FDA) include cetuximab, avelumab, rituximab, ipilimumab, and the like. However, according to recent clinical results, it is known that some monoclonal antibodies are significantly less effective in patients with genetic mutations located downstream of the receptor in the intracellular signaling system. Therefore, there remains a need for a new cancer therapeutic agent.

Contrast agents are pharmaceutical products that help to clearly distinguish tissue or vascular lesions by enhancing the contrast of images during imaging diagnostic examinations. Contrast agents are categorized according to the type of imaging diagnostic examination method, and iodine-based contrast agents are frequently used for X-ray and CT imaging and gadolinium-based contrast agents are frequently used for MRI.

SUMMARY OF THE INVENTION

Under these circumstances, the present inventors confirmed that germanium telluride nanosheets having a single layer and coated with polyvinylpyrrolidone have excellent anti-inflammatory activity and target inflammation sites.

In addition, the present inventors confirmed that the nanosheet also has excellent anticancer activity, exhibits photothermal properties, absorbs light in the ultraviolet to near-infrared region, and thus has various activities.

Therefore, an object of the present invention is to provide a use of the nanosheet for treating inflammatory diseases, treating cancer and as a contrast agent.

To achieve the object, one aspect of the present invention provides a pharmaceutical composition for preventing or treating inflammatory diseases, containing single layer of germanium telluride nanosheets coated with polyvinylpyrrolidone as an active ingredient.

As used herein, the term "prevention" refers to all actions that suppress a disease or delay the onset of the disease by administering the pharmaceutical composition according to the present invention.

As used herein, the term "treatment" refers to all actions that ameliorate or beneficially change symptoms of a disease by administering the pharmaceutical composition according to the present invention.

Germanium telluride (GeTe) is a compound of germanium and tellurium, and is a small bandgap material of group IV-VI, which consists of atomic layers in which Ge and Te atoms are alternately bonded. Tellurium (Te) is an element having chemical properties similar to selenium (Se), and is known to be involved in the in vivo antioxidant function and selectively generate active oxygen only in cancer cells.

Therefore, the present inventors have conducted research to develop a therapeutic agent for inflammatory bowel disease, which can be orally administered using tellurium, and as a result, they confirmed that germanium telluride (GeTe) in the form of nanosheets has excellent anti-inflammatory activity (Examples 5, 9 and 11). In particular, the surface of the germanium telluride nanosheets of the present invention is coated with polyvinylpyrrolidone because the germanium telluride (GeTe) nanosheets themselves easily aggregate in liquids (see Preparation Example).

The inflammatory disease may be one or more diseases selected from the group consisting of inflammatory bowel disease (Crohn's disease or ulcerative colitis), psoriasis, atopic dermatitis, psoriatic arthritis, rheumatoid arthritis, ankylosing spondylitis and systemic lupus erythematosus, and may be preferably inflammatory bowel disease or psoriasis.

Specifically, the present inventors confirmed that when germanium telluride nanosheets coated with polyvinylpyrrolidone (referred to as GeTe-PVP NS) were orally administered to an animal model in which inflammatory bowel disease was induced, intestinal bleeding and intestinal length were reduced, the thickness of the intestine, which had increased due to inflammation, was reduced, and the inflammatory findings were also reduced.

The therapeutic effect of inflammatory bowel disease may be achieved by a decrease in pro-inflammatory factors selected from the group consisting of inducible nitric oxide synthase (iNOS), tumor necrosis factor-α (TNF-α) and interleukin-1β. Alternatively, the therapeutic effect may be achieved by an increase in anti-inflammatory factors selected from the group consisting of Arginase 1 (Arg 1) and cluster of differentiation 206 (CD206).

Therefore, it was confirmed that when GeTe-PVP NSs were subcutaneously injected into an animal model in which psoriasis was induced, the Psoriasis Area severity Index (PASI), which is the most commonly used evaluation method in the clinical evaluation of psoriasis, was improved and inflammatory responses such as scaling, redness, and skin thickening were reduced.

Although described in detail below, GeTe-PVP NS exhibits a photoacoustic effect, and thus enables imaging when administered in vivo, and may target an inflammatory site. Therefore, the pharmaceutical composition for treating inflammatory diseases of the present invention has an advantage of being able to target and treat an inflammatory site and track the course of treatment through imaging.

In the present invention, the pharmaceutical composition for treating inflammatory diseases may be a formulation for oral or parenteral administration. For example, the pharmaceutical composition for treating inflammatory diseases may be a formulation for oral administration when applied to inflammation in vivo such as inflammatory bowel disease, and may be a formulation for parenteral administration when used for the treatment of external inflammation such as psoriasis or dermatitis.

The pharmaceutical composition according to an exemplary embodiment of the present invention may be applied to all animals including humans, dogs, chickens, pigs, cows, sheep, guinea pigs or monkeys.

The pharmaceutical composition according to an exemplary embodiment of the present invention may include a diluent, an excipient, lubricants, a binder, a disintegrant, a buffer, a dispersant, a surfactant, a colorant, a flavorant or a sweetener, if necessary. The pharmaceutical composition according to an exemplary embodiment of the present invention may be prepared by a typical method in the art.

In the present invention, examples of a carrier, an excipient and a diluent, which may be included in the pharmaceutical composition, include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

The pharmaceutical composition according to an exemplary embodiment of the present invention may be administered orally, rectally, transdermally, intravenously, intramuscularly, intraperitoneally, intramedullary, intrathecally, intradermally, or the like.

Formulations for oral administration may be tablets, pills, soft or hard capsules, granules, powders, liquids or emulsions, but are not limited thereto. Formulations for parenteral administration may be injections, drops, gels, suspensions, emulsions, suppositories, patches or sprays, but are not limited thereto. The pharmaceutical compositions may be in the form of a sterile injectable preparation as a sterile injectable aqueous or oily suspension. The suspension may be formulated according to techniques known in the art using a suitable dispersant or wetting agent (for example, Tween 80) and a suspending agent. The sterile injectable preparation may also be a sterile injectable solution or suspension in a non-toxic parenterally acceptable diluent or solvent (for example, a solution in 1,3-butanediol). Examples of a vehicle and a solvent that may be acceptably used include mannitol, water, Ringer's solution, and an isotonic sodium chloride solution. Furthermore, sterile, non-volatile oils are typically used as a solvent or suspending medium. Any mild or non-volatile oil, including synthetic mono- or diglycerides, may be used for this purpose. Natural oils in which fatty acids such as oleic acid and glyceride derivatives thereof are pharmaceutically acceptable (for example, olive oil or castor oil), particularly polyoxyethylated versions thereof, are also useful in injectable preparations.

Parenteral administration of the pharmaceutical composition according to the present invention is particularly useful when a target treatment is associated with sites or organs readily accessible by topical application. Examples of a carrier for topical administration of the composition of the present invention include, but are not limited to, mineral oil, liquid paraffin, white petrolatum, propylene glycol, a polyoxypropylene compound, emulsifying wax and water.

An active ingredient of the pharmaceutical composition according to the present invention may vary depending on the age, sex, body weight, pathological condition, and severity of a subject to be administered, administration route, or the judgment of a prescriber. The determination of dosage based on these factors is within the level of those skilled in the art, and the daily dose thereof may be, for example, 10 ng/kg/day to 10 mg/kg/day, specifically 0.1 µg/kg/day to 1 mg/kg/day, more specifically 1 µg/kg/day to 100 µg/kg/day, and even more specifically 2 µg/kg/day to 50 µg/kg/day, but may be adjusted appropriately when different doses show different effects. The pharmaceutical composition according to an exemplary embodiment of the present invention may be administered once to three times a day, but is not limited thereto.

Meanwhile, the present inventors confirmed that GeTe-PVP NS has no toxicity to normal cells, kills cancer cells, and exhibits photothermal properties. Therefore, another aspect of the present invention provides a pharmaceutical composition for preventing or treating cancer, comprising single layer of germanium telluride nanosheets coated with polyvinylpyrrolidone as an active ingredient.

In the pharmaceutical composition for preventing or treating cancer, the details related to GeTe-PVP NS are the same as those described above, so the description on the duplicate content will be omitted.

In the present invention, the cancer may be selected from the group consisting of colorectal cancer, breast cancer, liver cancer, lung cancer, ovarian cancer, colon cancer, pancreatic cancer, liver cancer, cervical cancer, kidney cancer, gastric cancer, prostate cancer, brain tumors, uterine cancer and bladder cancer.

According to an exemplary embodiment of the present invention, the GeTe-PVP NS may be a photothermal material. The photothermal material refers to a material that generates heat by irradiating light (laser), and a treatment method that burns cancer cells by applying a near-infrared laser outside the body, using the weaknesses of cancer cells, which are more vulnerable to heat than normal cells refers to photothermal therapy.

According to an exemplary embodiment of the present invention, the temperature of a GeTe-PVP NS solution was increased by a laser in the near-infrared region (Example 4). Therefore, the pharmaceutical composition for preventing or treating cancer of the present invention may not only kill cancer cells by itself, but also exhibit an excellent anticancer effect when used in combination with photothermal therapy.

In the present invention, the pharmaceutical composition for preventing or treating cancer may be administered alone or in combination with other anticancer agents, the order of administration is not particularly limited when the pharmaceutical composition is administered in combination, and the pharmaceutical composition may be administered simultaneously or sequentially with other anticancer agents.

The present inventors confirmed that GeTe-PVP NS exfoliated into thin layers has an indirect bandgap in the vis-NIR region (about 1.84 eV), and thus absorbs and emits light in a region of not only NIR I (750 to 900 nm), but also NIR II (950 to 1350 nm).

Therefore, still another aspect of the present invention provides a contrast agent composition comprising single layer of germanium telluride nanosheets coated with polyvinylpyrrolidone.

In the contrast agent composition, the details related to GeTe-PVP NS are the same as those described above, so the description on the duplicate content will be omitted.

Contrast agents are drugs that help to clearly distinguish lesions in tissues and blood vessels by increasing the contrast of images during diagnostic imaging examinations, and in general, an iodinated contrast agent is used for CT examinations, a gadolinium contrast agent is used for MRI imaging, and a barium contrast medium is used for the gastrointestinal tract (stomach).

As described above, GeTe-PVP NS exfoliated into one or two thin layers absorbs and emits light in the near-infrared region to exhibit a photoacoustic effect, so it may be used as a NIR fluorescence contrast agent and a multi-imaging contrast agent for multispectral optoacoustic tomography (MSOT) imaging.

The photoacoustic effect refers to a process in which laser energy is converted into thermal energy in living tissue that has absorbed irradiated laser energy, and a photoacoustic signal is produced by the thermal expansion that occurs at this time. The generated photoacoustic signal has an ultrasonic frequency band of several MHz to several tens of MHz, and may be sensed using an ultrasonic transducer used for ultrasonic imaging. The signals thus sensed are visualized through various signal processing processes.

According to an exemplary embodiment of the present invention, since the GeTe-PVP NS can target an inflammation site, the contrast agent composition of the present invention may be useful for diagnosing an inflammation site in vivo.

The contrast agent composition according to the present invention may be formulated into an injection preparation, and when the composition is formulated into an injection preparation, the injection preparation may include a non-toxic buffer solution, which is isotonic to blood, as a diluent, and examples of the non-toxic buffer solution include a phosphoric acid buffer solution with a pH of 7.4, and the like. The contrast agent composition may include other diluents or additives in addition to the buffer solution. Excipients and additives which may be added to these injections are widely known to those with ordinary skill in the art, and can be found by referencing, for example, the following document (Dr. H. P. Fiedler "Lexikon der Hilfsstoffe fur Pharmazie, Kosmetik and angrenzende Gebiete" [Encyclopaedia of auxiliaries for pharmacy, cosmetics and related fields].

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

Hereinafter, one or more specific exemplary embodiments will be described in more detail through Examples. However, these Examples are provided only for exemplarily explaining the one or more specific exemplary embodiments, and the scope of the present invention is not limited to these Examples.

Preparation Example: Preparation of Germanium Telluride Nanosheets (GeTe-PVP NSs) Coated with Polyvinylpyrrolidone 1-1. Preparation of GeTe-PVP NSs Bulk germanium telluride (GeTe) powder was purchased from TRUNNANO (Henan, China). Phosphate buffered saline (PBS, pH 7.4), pH 2 and 8 buffers, ethanol and polyvinylpyrrolidone (PVP) with a molecular weight of about 29 K were purchased from Sigma-Aldrich (St. Louis, USA). All other agents used were of the highest commercial quality available. Deionized water was used to prepare all solutions.

Germanium telluride nanosheets (hereinafter referred to as GeTe-PVP NSs) coated with polyvinylpyrrolidone were prepared using liquid-phase exfoliation.

First, GeTe powders were sonicated in ethanol for exfoliation. However, GeTe NSs quickly aggregated and precipitated in the solution. To prevent aggregation, GeTe NSs were coated with polyvinylpyrrolidone (PVP) by sonicating.

Specifically, GeTe powder was dispersed in a 1 mg/ml mixture of ethanol and PVP with an initial concentration of 5 mg/ml. Then, the suspension was sonicated for 10 h in an ice-bath at 500 W and centrifuged at 3,000 rpm for 10 min to remove the clumps of un-exfoliated bulk GeTe. The supernatant was then centrifuged at 10,000 rpm for 30 min and washed with deionized water for three times. The final precipitate was dispersed in PBS and stored at 4° C. for future use.

Figure 1:
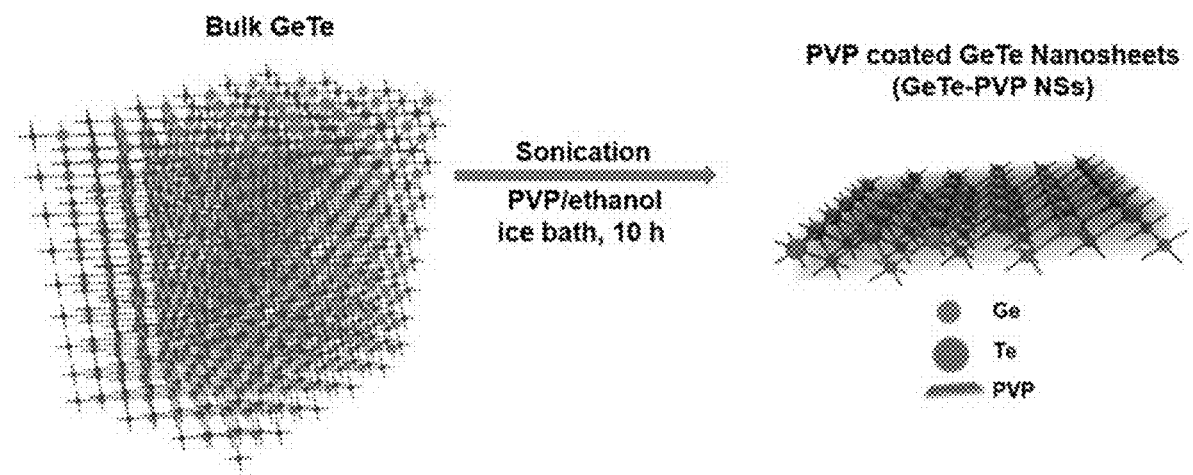
FIG. 1 illustrates the process of fabricating germanium telluride nanosheets coated with polyvinylpyrrolidone (hereinafter referred to as GeTe-PVP NS) according to an exemplary embodiment of the present invention.

The process of preparing GeTe-PVP NSs is schematically illustrated in FIG. 1.

1-2. Characterization of GeTe-PVP NSs

Figure 2A:
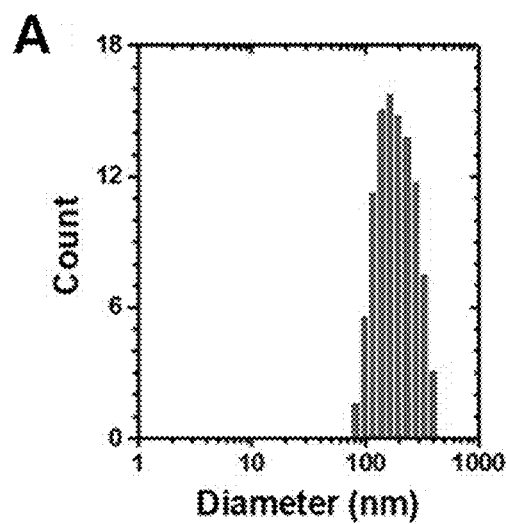
FIG. 2A illustrates the results of confirming the size of the fabricated GeTe-PVP NS.
Figure 2B:
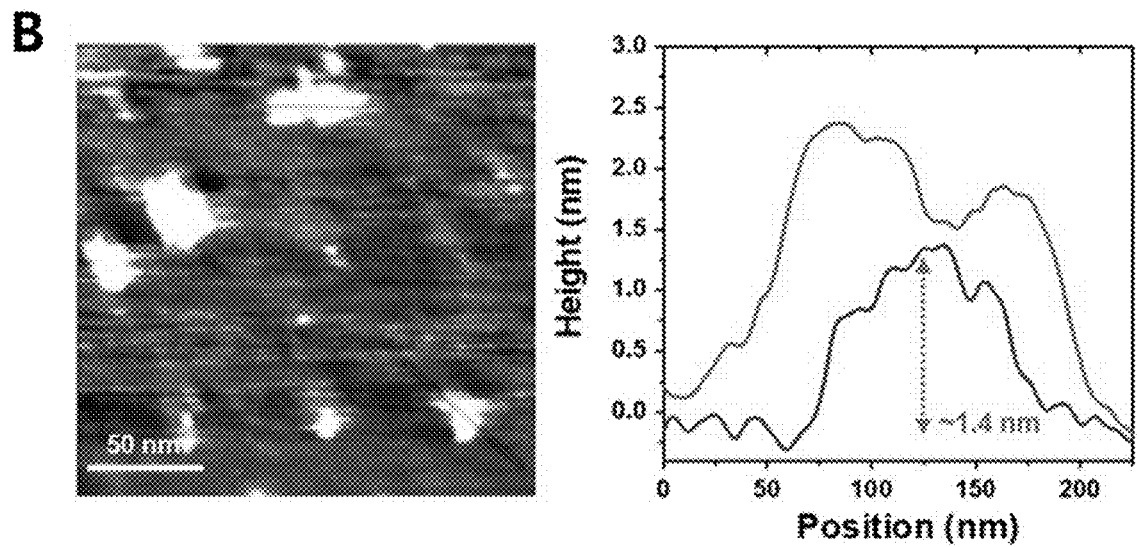
FIG. 2B illustrates the results of confirming the thickness of the fabricated GeTe-PVP NS.

The thicknesses of GeTe-PVP NSs were measured using direct light scattering analysis and atomic-force microscopy, AFM; NX-10, Park Systems, Korea). As a result, it could be seen that bulk GeTe was successfully exfoliated into a single layer by confirming that the GeTe-PVP NS had a thickness of about 1.4 nm with a single layer (FIG. 2B) and an average size of 166 nm (FIG. 2A).

In addition, as a result of observing the morphologies of the prepared GeTe-PVP NSs with a transmission electron microscope (TEM; JEM-F200, JEOL, Japan), a selected area electron diffraction (SAED) pattern could be observed.

Figure 3A:
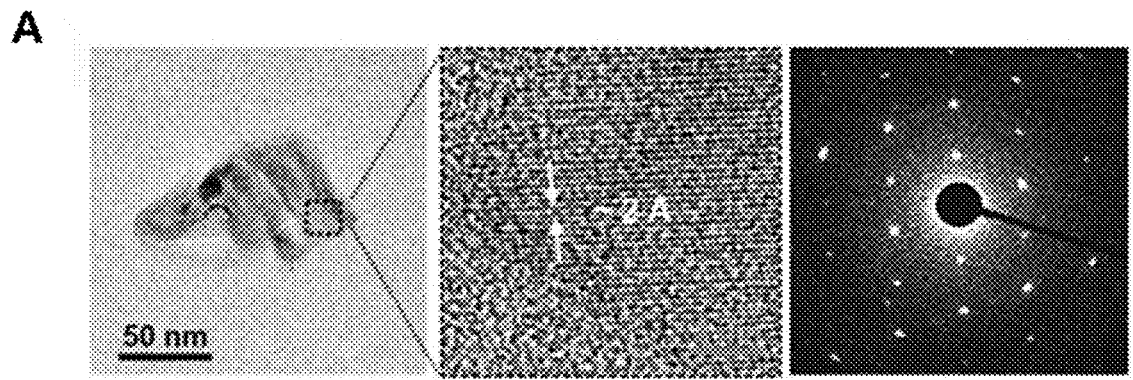
FIG. 3A illustrates the results of morphological analysis of the fabricated GeTe-PVP NS.
Figure 3B:
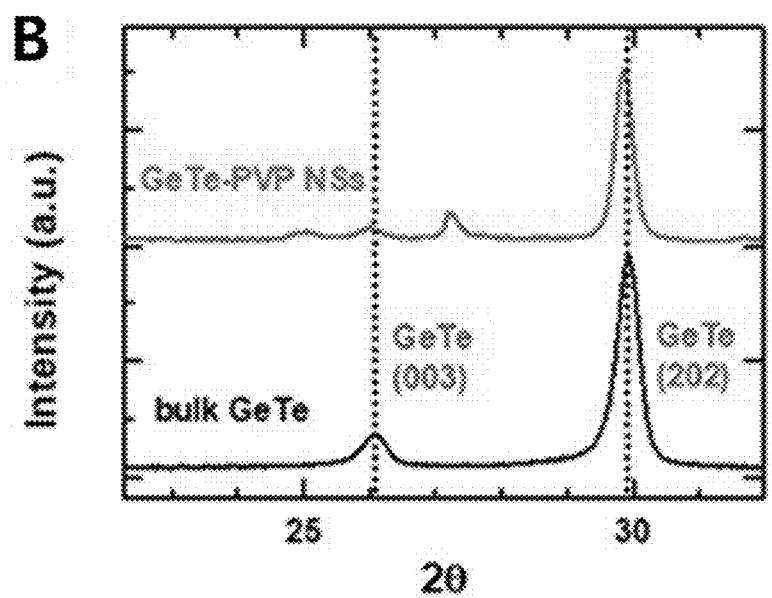
FIG. 3B illustrates the results of X-ray diffraction analysis of the fabricated GeTe-PVP NS.

In the X-ray diffractometry (XRD) spectrum results, a sharp peak was observed at $2\theta=29.8°$, and this peak is a characteristic peak of rhombohedral GeTe for both bulk GeTe and GeTe-PVP NSs (FIG. 3B). Therefore, the observation of this peak indicates that the crystallinity is well maintained even after exfoliation of bulk GeTe.

Next, it was confirmed whether GeTe NSs were coated with PVP.

Figure 4A:
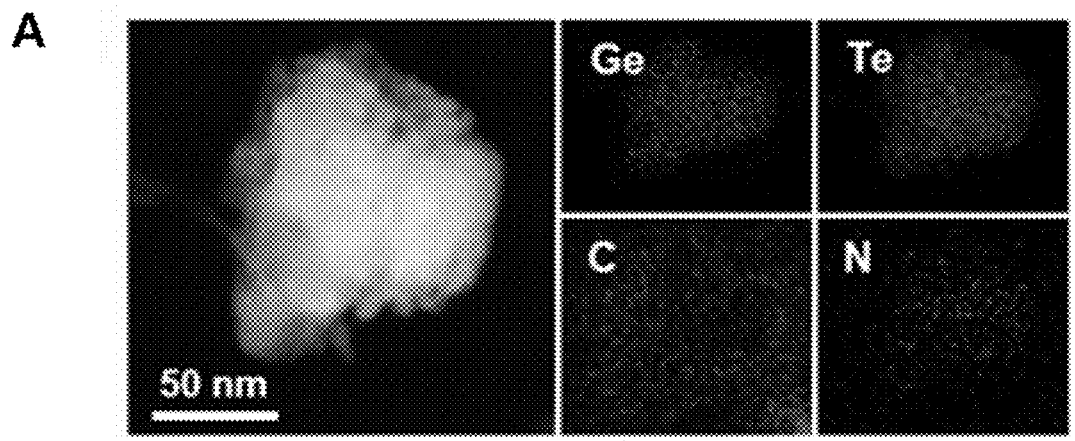
FIG. 4A illustrates the results of confirming whether the surface of the germanium telluride nanosheet is coated with polyvinylpyrrolidone by energy-dispersive X-ray spectroscopy.

Energy-dispersive X-ray spectroscope (EDS) mapping images showed that the surfaces of GeTe NSs were well coated with PVP (FIG. 4A).

Figure 4B:
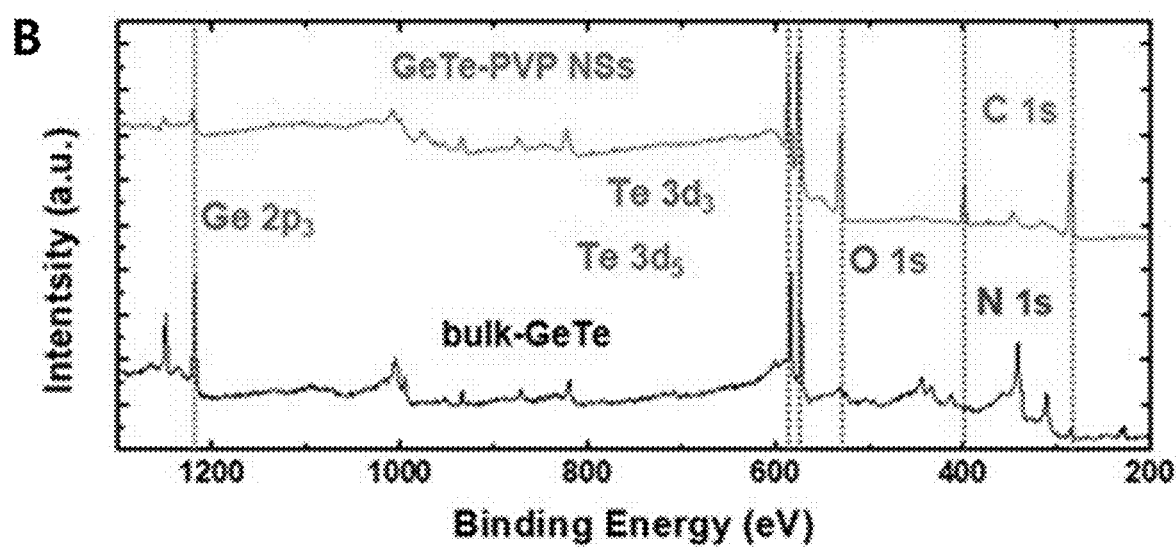
FIG. 4B illustrates the result of confirming whether the surface of the germanium telluride nanosheet is coated with polyvinylpyrrolidone by X-ray photoelectron spectroscopy.

X-ray photoelectron spectroscopy (XPS) spectra displayed Ge $2p_3$, Te $3d_3$ and Te3 $d_5$ peaks at 1218, 583 and 573 eV, respectively, for both GeTe and GeTe-PVP NSs. In contrast, O 1s, N 1s, and C 1s peaks originating from PVP were observed at 531, 398, and 285 eV, respectively, only in GeTe-PVP NSs (FIG. 4B). This result clearly indicates that GeTe NSs were well coated with PVP.

Comparative Example: Preparation of Gold Nanorods

Step 1 (gold seed solution): 5 ml of $HAuCl_4$ (0.01 M) was added to 5 ml of cetrimonium bromide (CTAB) (0.2 M). Thereafter, 60 μl of cold $NaBH_4$ was added thereto and stirred for 2 minutes to prepare a gold seed solution. The prepared gold seed solution was stored at room temperature for 3 hours or more, and then used.

Step 2 (growth of gold nanoparticles): 30 μl of $AgNO_3$ (0.01 M) and 5 ml of $HAuCl_4$ (0.01 M) were added to 5 ml of CTAB (0.2 M), and then the resulting mixture was stirred. When 55 μl of ascorbic acid (0.1M) was added to the reaction solution, a yellow reaction solution turned colorless. The reaction solution was reacted at 30° C. for 1 hour while being stirred at 150 rpm (shaking incubation), and 12 ml of the gold seed solution of Step 1 was added thereto. Gold nanorods (GNR) were grown by reacting the mixture at 30° C. with stirring at 150 rpm for 24 hours. The color of the solution changed from colorless to reddish-brown during this process. Thereafter, the reaction time was adjusted (900 ml of CTAB solution: 30° C., 18 hours) to standardize the length of the gold nanoparticles.

Example 1: Optical Spectral Analysis of GeTe-PVP NS

Optical spectra for GeTe-PVP NS (Preparation Example), gold nanorods (Comparative Example 1), and Indocyanine green (ICG; Sigma-Aldrich, St. Louis, USA) (Comparative Example 2) were confirmed by the Cary5000 UV-Vis-NIR spectrophotometer (Agilent, USA) and FL and PL fluorescence spectrophotometers (F-2500 fluorescence spectrophotometer; Hitachi, Japan).

Figure 5A:
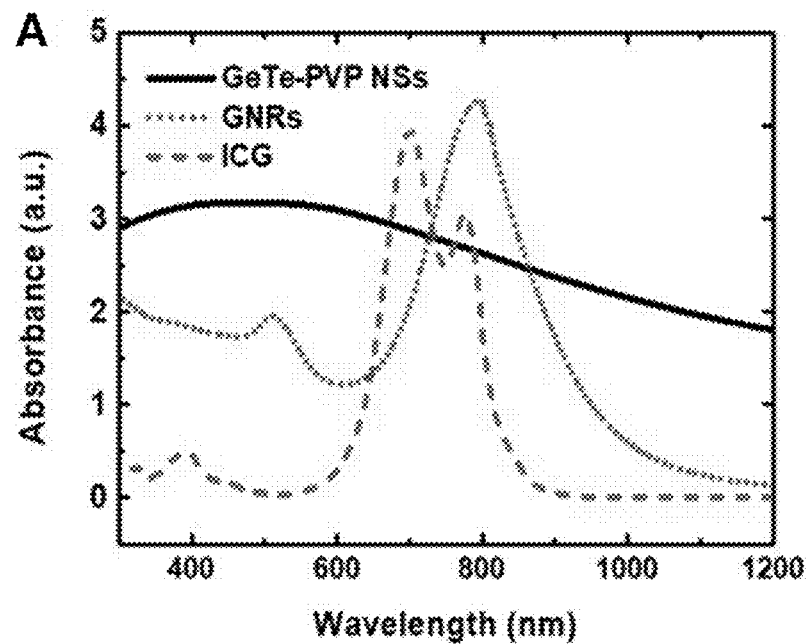
FIG. 5A illustrates the results of confirming the absorption spectra of GeTe-PVP NS, gold nanorods (GNRs), and an indocyanine green (ICG) solution in the ultraviolet to near-infrared regions.

As a result, absorption spectra and fluorescence properties in the ultraviolet (UV) to near-infrared (NIR) regions were confirmed for the solution. GeTe-PVP NSs exhibited absorbance similar to gold nanorods (GNRs) and the ICG solution at the same concentration in the NIR I region (750 to 900 nm), but exhibited much higher absorbance in the NIR II region (950 to 1350 nm) (FIG. 5A).

Figure 5B:
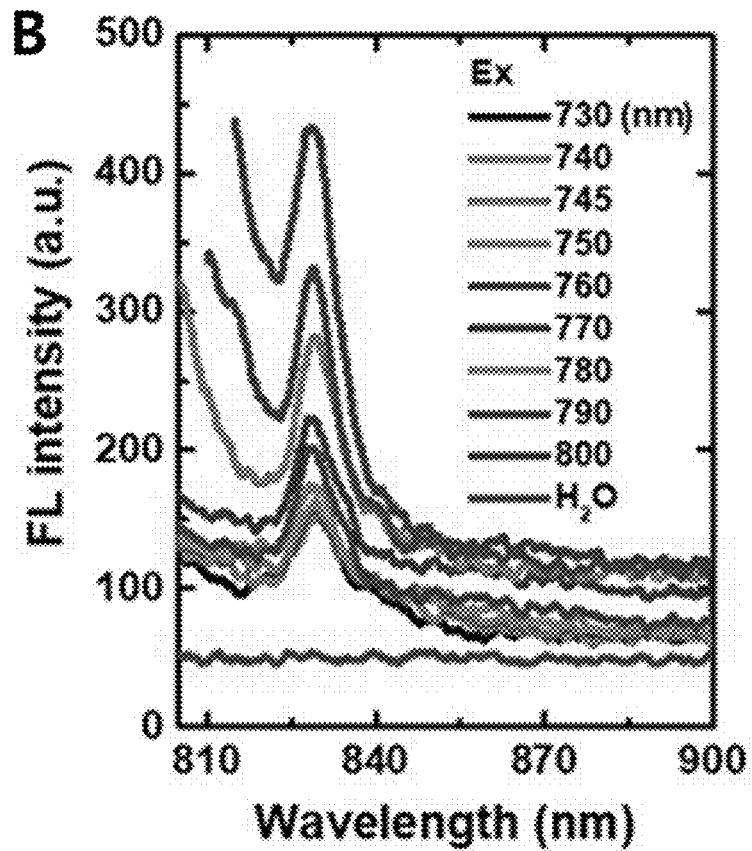
FIG. 5B illustrates the results of confirming the fluorescence spectra of the GeTe-PVP NS solution.

Further, as a result of measuring fluorescence (FL) spectra for GeTe-PVP NSs (25 μg/ml) at different wavelengths, an FL peak could be observed at approximately 830 nm, and its intensity systematically increased at longer excitation wavelengths (FIG. 5B). These results suggest that GeTe-PVP NSs can be used as contrast agents for FL and multispectral optoacoustic tomography (MSOT) imaging.

Figure 6A:
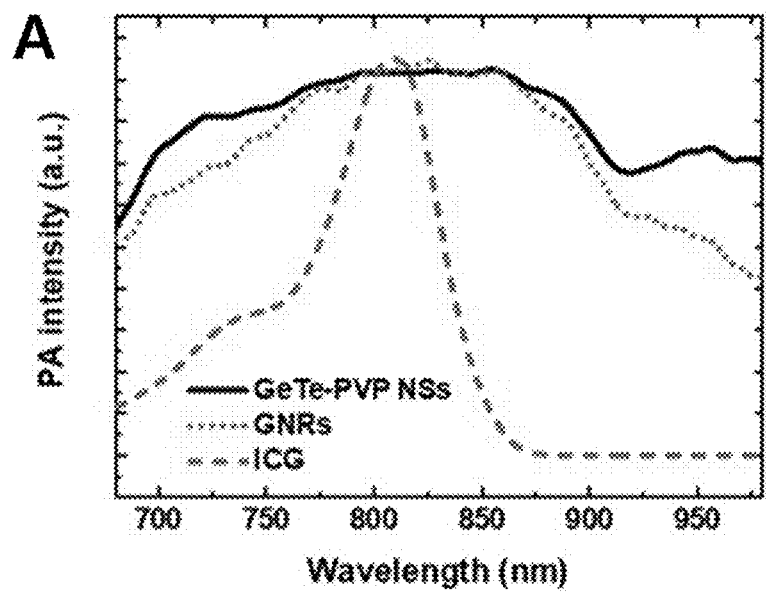
FIG. 6A illustrates the results of confirming the photoacoustic absorbance of the GeTe-PVP NS solution.
Figure 6B:
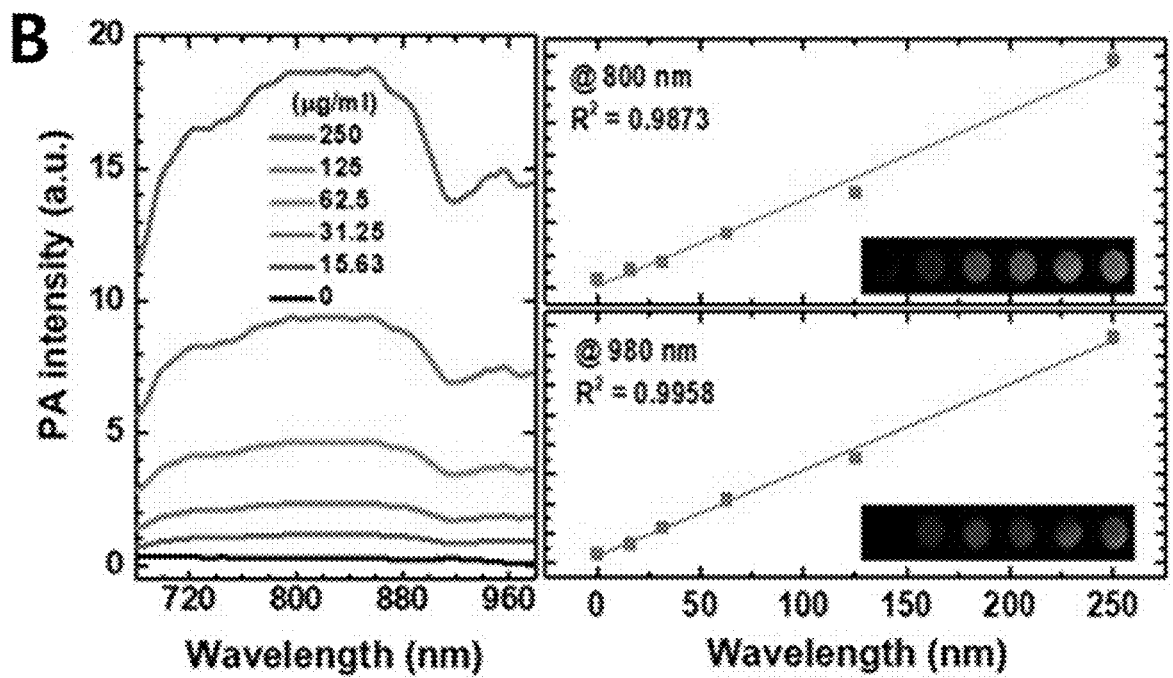
FIG. 6B illustrates the results of confirming the photoacoustic absorbance of solutions containing GeTe-PVP NS at various concentrations.

In addition, the changed optical absorption properties and fluorescence properties of GeTe-PVP NSs were confirmed through PA spectroscopy results using MSOT. As a result, it could be seen that GeTe-PVP NSs can be used for imaging by confirming the photoacoustic effect of GeTe-PVP NSs. The GeTe-PVP NS solution showed higher PA absorbance than GNRs and ICG at wavelengths equal to or higher than 900 μm, which is the NIR II region (FIG. 6A). Furthermore, it was shown that the photoacoustic absorbance further increased at 800 nm and 980 nm as the concentrations of GeTe-PVP NSs increased (FIG. 6B).

Example 2: Penetration Depth Measurement of GeTe-PVP NS s

Figure 7:
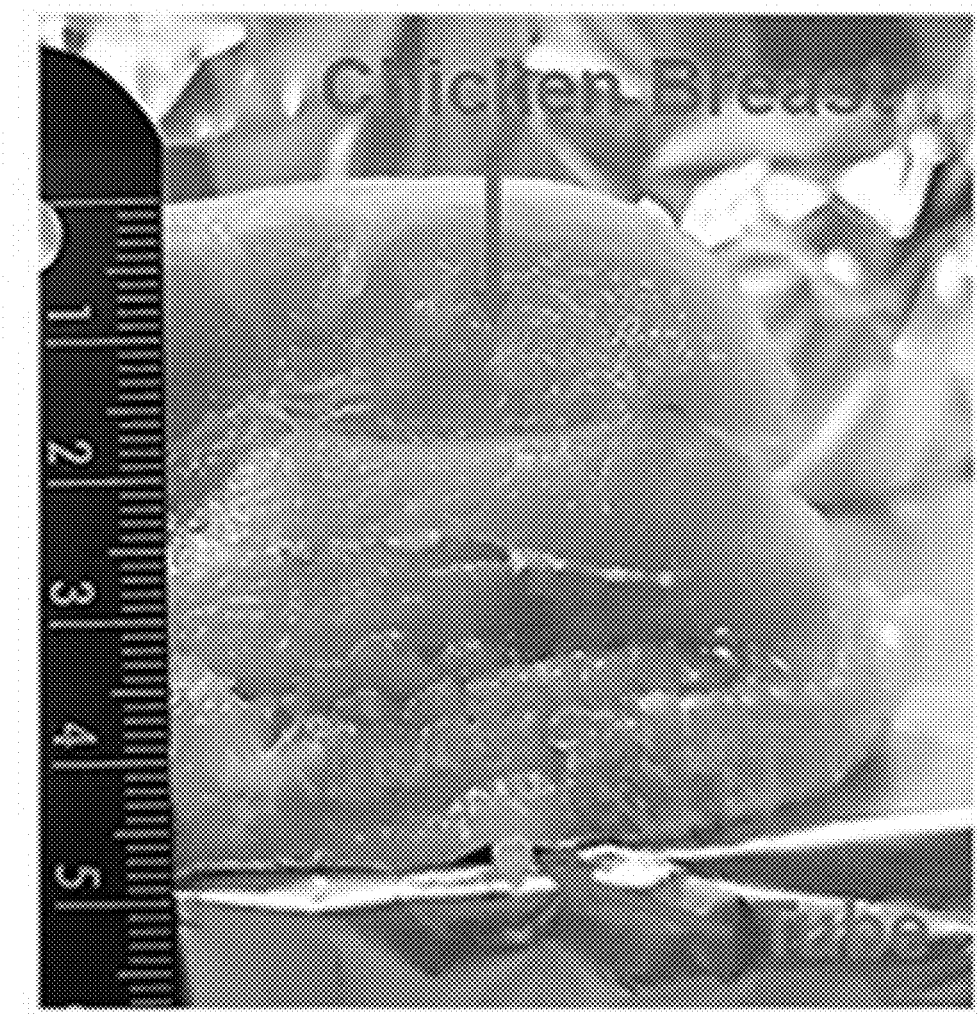
FIG. 7 shows a chicken breast stacked on top of a tube containing a GeTe-PVP NS solution.

Chicken breast tissues were stacked by varying the thicknesses from 1 cm to 5 cm (FIG. 7). A 3 mm diameter tube containing 0.1 ml of 0.5 mg/ml GeTe-PVP NS or gold nanorod solution was placed in the middle of the chicken breasts stacked layer by layer, and the tube was imaged with MSOT inVision 256-TF. The data was reconstructed and conducted using multispectral processing with ViewMSOT software (iThera Medical, Germany)

Figure 8A:
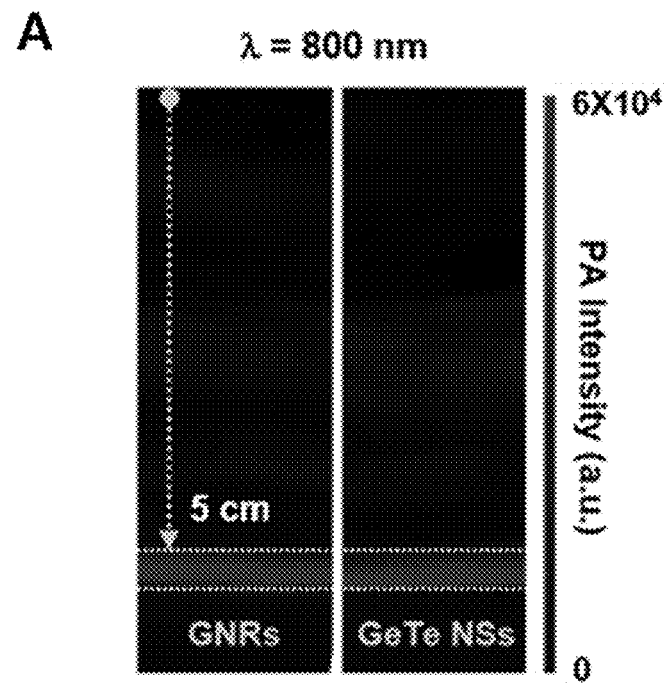
FIGS. 8A-F illustrates the results of confirming the changes in photoacoustic absorbance of GeTe-PVP NS according to the thickness of chicken breast tissue in the regions of $\lambda=800$ nm (A and B), $\lambda=950$ nm (C and D) and $\lambda=680$ to 980 nm (E and F)
Figure 8B:
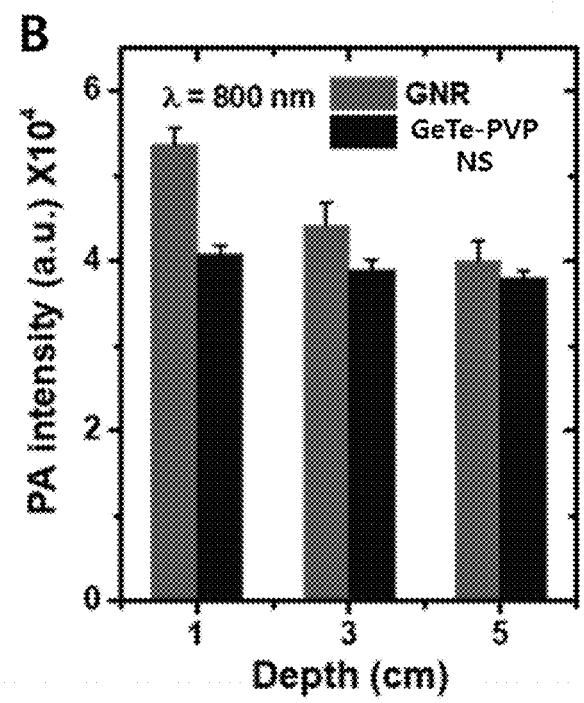
Figure 8C:
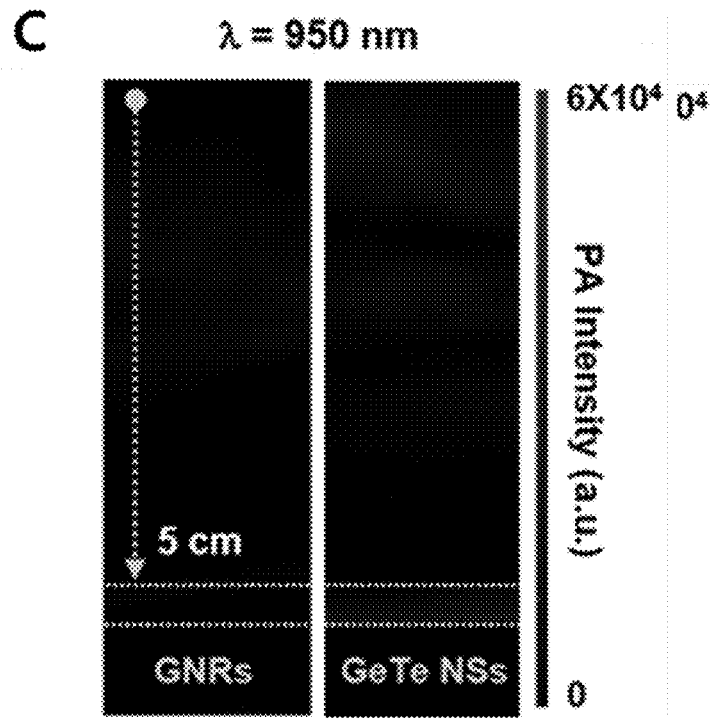
Figure 8D:
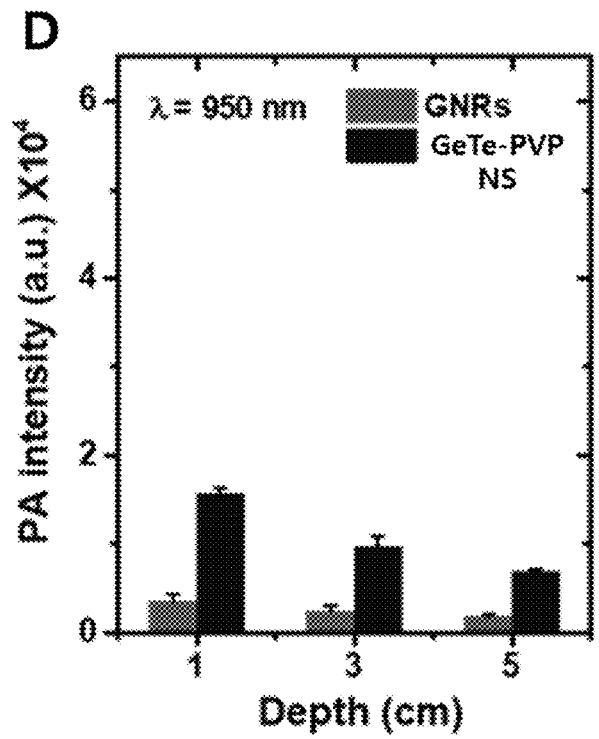
Figure 8E:
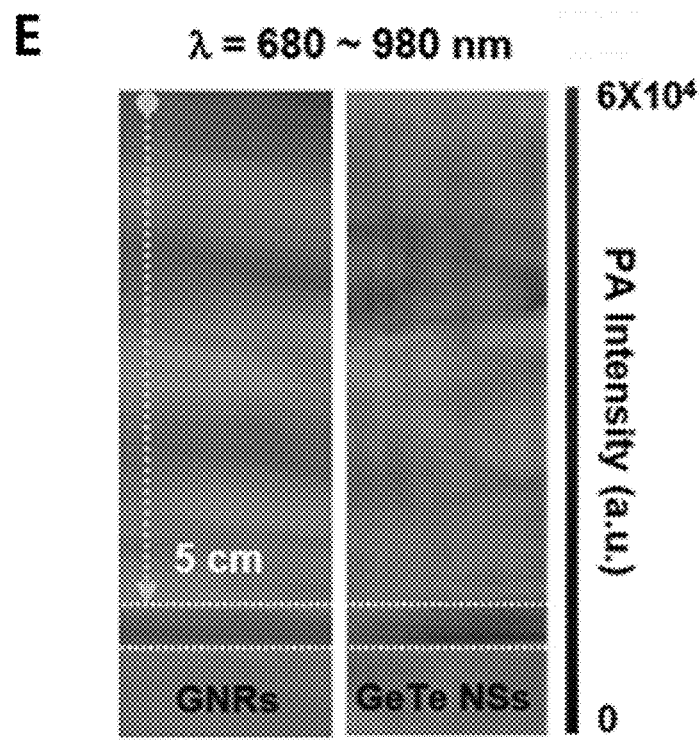
Figure 8F:
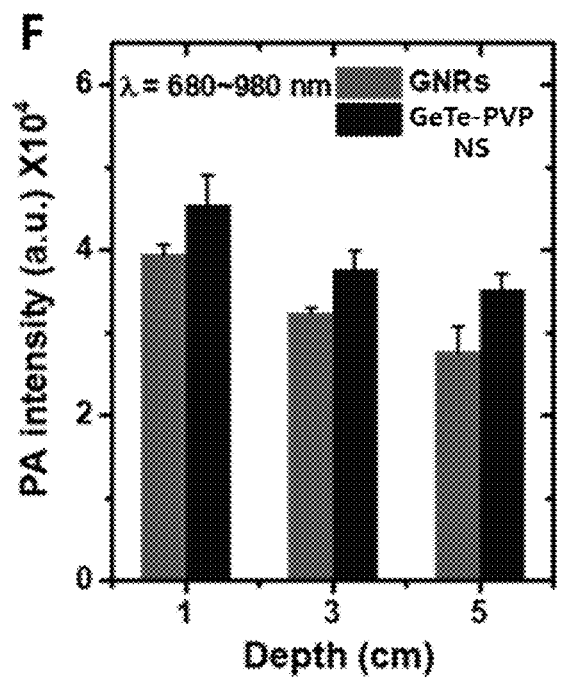

It could be confirmed that gold nanorods exhibited slightly higher PA intensities at λ=800 nm than GeTe-PVP NSs at a thickness of up to 5 cm (FIGS. 8A and 8B), but GeTe-PVP NSs exhibited remarkably higher PA intensities than gold nanorods at λ=950 nm at all thicknesses, and images can be acquired up to a depth of 5 cm (FIGS. 8C and 8D). When comparing the images taken in the region of =680 to 980 nm, clearer images and PA intensities could be confirmed at all thicknesses when GeTe-PVP NSs were used rather than gold nanorods (FIGS. 8E and 8F).

Example 3: Photothermal Effect of GeTe-PVP NSs 3-1. Photothermal effect of GeTe-PVP NS solution GeTe-PVP NS aqueous dispersions at a concentration of 0.25 mg/ml were exposed to an 808-nm NIR laser at power densities of 0.5, 1, 1.5, and 2 W cm$^{-2}$ for 100 min, respectively. The laser was turned on for 10 min and then turned off for 10 min, and this was repeated five times. The temperature change of the membranes was recorded every 1 min using an IR thermal camera (FLIR T335 Thermal Imaging Camera, FLIR, USA).

Figure 9:
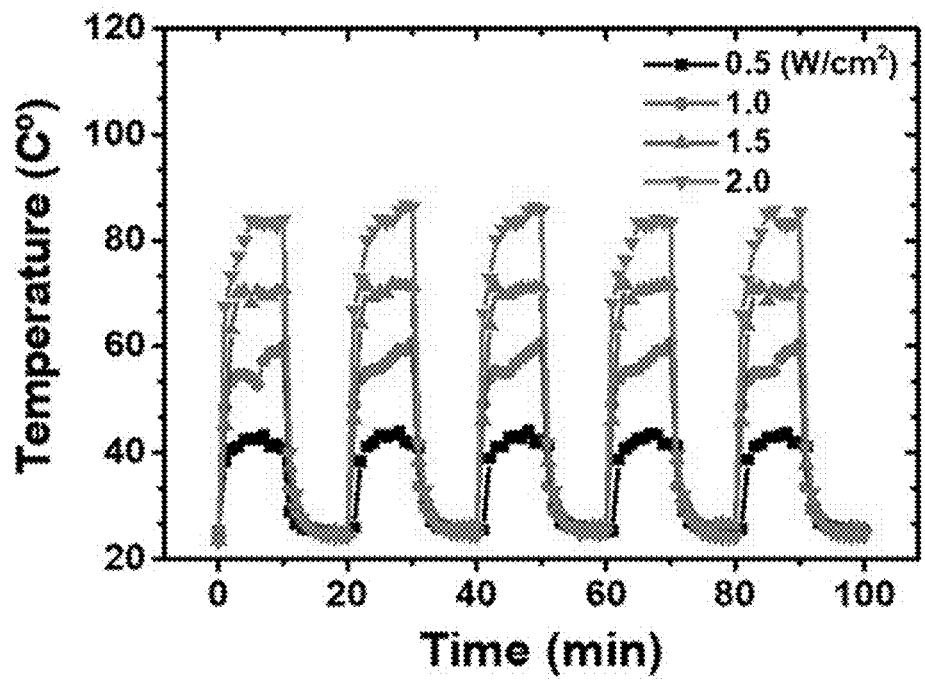
FIG. 9 illustrates the results of recording the temperature change while exposing the aqueous dispersion of GeTe-PVP NS to a laser.

As a result, it could be confirmed that the temperature of the dispersion increased to 18.4±0.4, 35.2±0.3, 47.8±0.4, and 61.9±1.3° C., respectively, and that the temperature of the dispersion immediately dropped to room temperature when the laser was turned off. Furthermore, it could be seen that the temperature rises and drops in the same way even though the experiment was repeated five times (FIG. 9).

Since the elevated temperature of the dispersion is the temperature that kills cancer cells, it is expected that GeTe-PVP NSs can be used for phototherapy, which is one method of cancer treatment.

3-2. Photothermal Effect of Phantom Containing GeTe-PVP NSs

Figure 10:
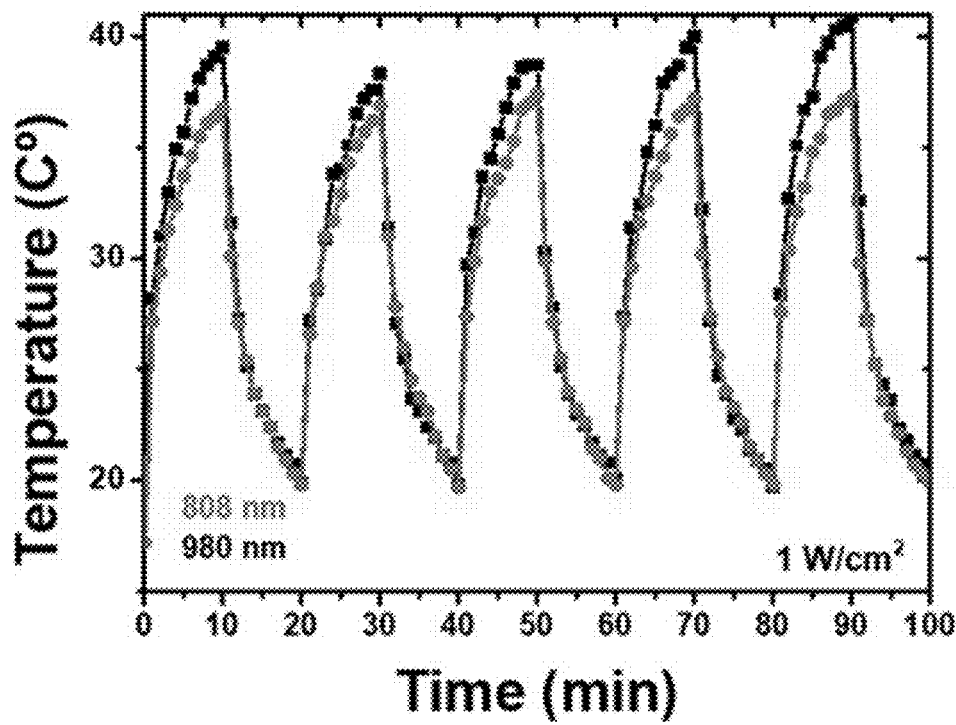
FIG. 10 illustrates the results of recording the temperature change of gelatin containing GeTe-PVP NS while irradiating the gelatin with a laser.

To measure the photothermal effect of GeTe-PVP NSs in vivo, gelatin containing GeTe-PVP NSs at a concentration of 0.25 mg/ml was prepared. The gelatin was irradiated with an 808 nm laser in the NIR I region and a 980 nm laser in the NIR II region at an intensity of 1 W/cm$^2$ for 10 minutes. As a result of measuring the temperature change of gelatin, it could be confirmed that the temperature of gelatin increased to 19.8±1.0 and 20.1±0.3° C. (FIG. 10). Since this is a temperature that sufficiently kills cancer cells, GeTe-PVP NSs can be used for the purpose of photothermal therapy in cancer therapy.

Example 4: Cytotoxicity and Anti-Inflammatory Assays of GeTe-PVP NSs 4-1. Cytotoxicity and GeTe-PVP NSs Two types of primary cells, human mesenchymal stem cells (hMSCs) and human fibroblast-like synoviocytes (FLSs) and two cell lines of murine macrophage cells (RAW264.7) and African green monkey kidney epithelial cells (Vero CCL-81) were seeded in 96-well plates at a density of 8,000 cells per well. Cells were cultured overnight in an incubator maintained at 37° C. in 5% $CO_2$ and a humidified atmosphere. The primary cells were cultured in a low glucose DMEM medium (Corning, USA) supplemented with 10% (v/v) FBS and the cell lines were cultured in a high glucose DMEM medium supplemented with 10% (v/v) FBS. The next day, the culture medium was replaced with a fresh culture medium containing different concentrations of GeTe-PVP NSs (0 to 50 μg/ml) and incubated for 24 hours. Cell viability was then determined by CCK-8 Assay (96992, Sigma). 10 μL of CCK-8 reagent was added to each well, and the plate was incubated for 2 hours. Cell viability was assessed by measuring the optical density at 450 nm.

Figure 11:
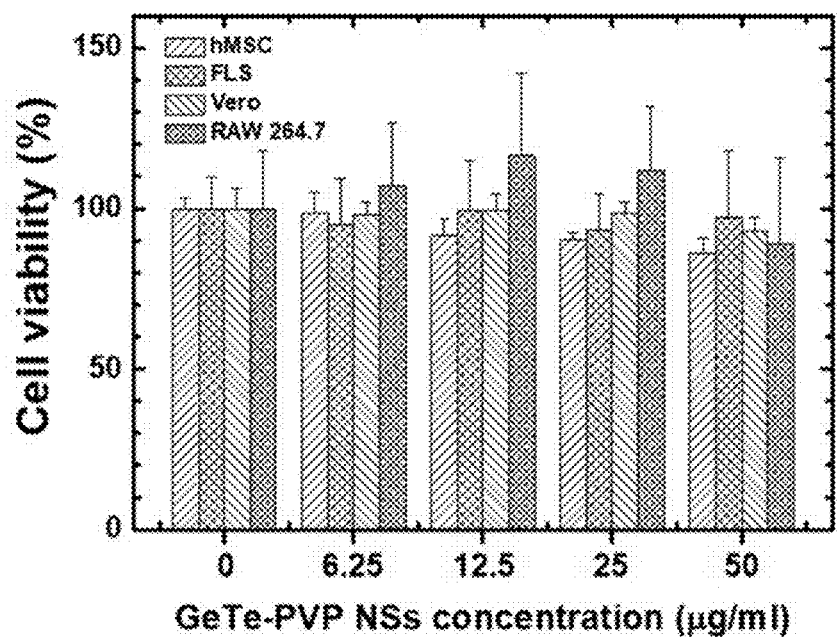
FIG. 11 illustrates the results of confirming cell viability according to treatment concentration after treating various types of normal cells with GeTe-PVP NS.

As a result, it could be confirmed that GeTe-PVP NSs have no cytotoxicity (FIG. 11).

4-2. Measurement of In Vitro Anti-Inflammatory Activity of GeTe-PVP NSs

RAW264.7 macrophage cells were purchased from Korea Cell Line Bank. Cells were seeded at a density of 8×10$^5$ cells per well in 6-well plates and cultured overnight in DMEM medium (Corning, USA) supplemented with 10% (v/v) FBS. The next day, cells were treated and stimulated with 1 μg/ml of LPS and treated with various concentrations of GeTe-PVP NSs (0, 6.25, 12.5, 25, and 50 μg/ml) for 24 hours. Then, the cells were collected by scraping, and RNA was extracted using the GeneJET RNA Purification Kit (Thermo Scientifics). cDNA was synthesized using the Maxime RT premix kit (iNtRON Biotechnology, Korea). Real-time PCR was performed with the Step One Plus real-time PCR machine (Applied Biosystems, USA) using PCRBIO SYBR Green (PCRBIOSYSTEM, UK). Relative mRNA expression levels for each sample were calculated using the $2^{-\Delta\Delta CT}$ method with GAPDH expression. The confirmed genes are pro-inflammatory factors inducible nitric oxide synthase (iNOS), tumor necrosis factor-α(TNF-α) and interleukin-1β, and anti-inflammatory factors Arginasel (Arg 1) and CD 206.

Figure 12A:
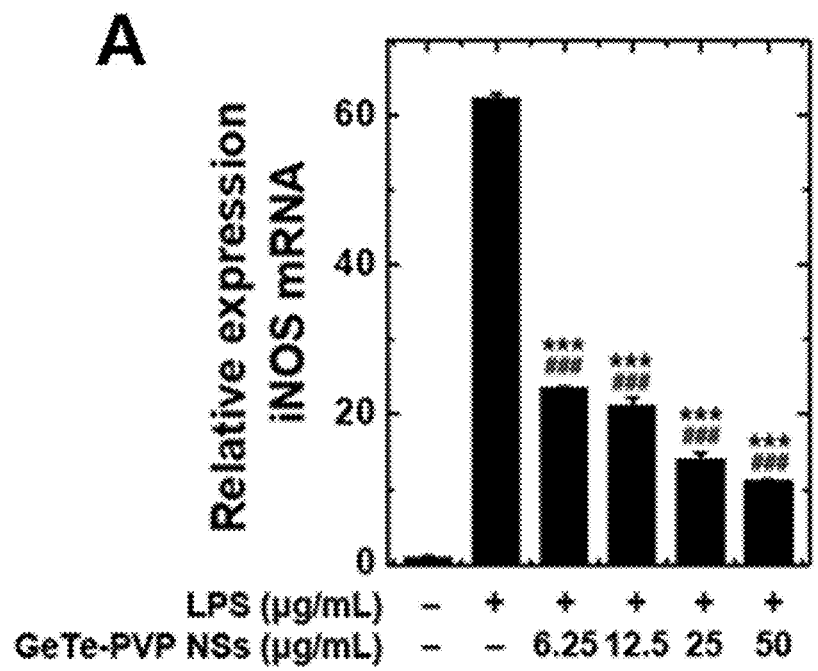
FIG. 12A illustrates the results of confirming the expression changes of iNOS (inducible nitric oxide synthase) mRNA after treating lipopolysaccharide (LPS)—stimulated macrophage cells with GeTe-PVP NS.
Figure 12B:
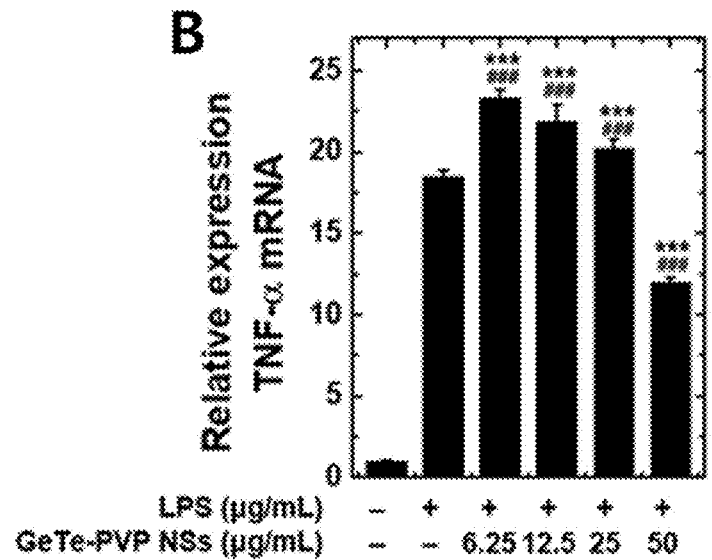
FIG. 12B illustrates the results of confirming the expression changes of TNF-α (tumor necrosis factor-α) mRNA after treating lipopolysaccharide (LPS)—stimulated macrophage cells with GeTe-PVP NS.
Figure 12C:
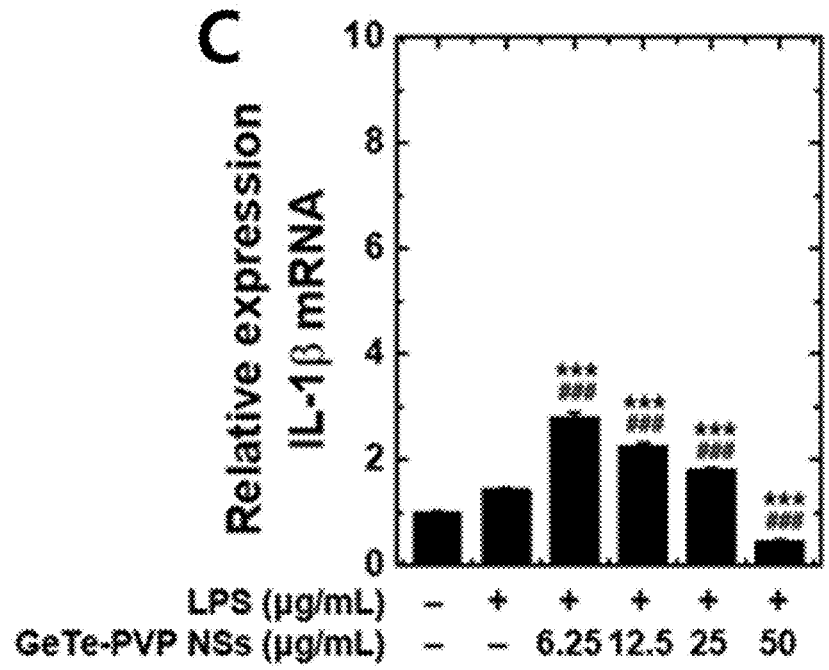
FIG. 12C illustrates the results of confirming the expression changes of IL-1β(interlukin-1β) mRNA after treating lipopolysaccharide (LPS)—stimulated macrophage cells with GeTe-PVP NS.
Figure 12D:
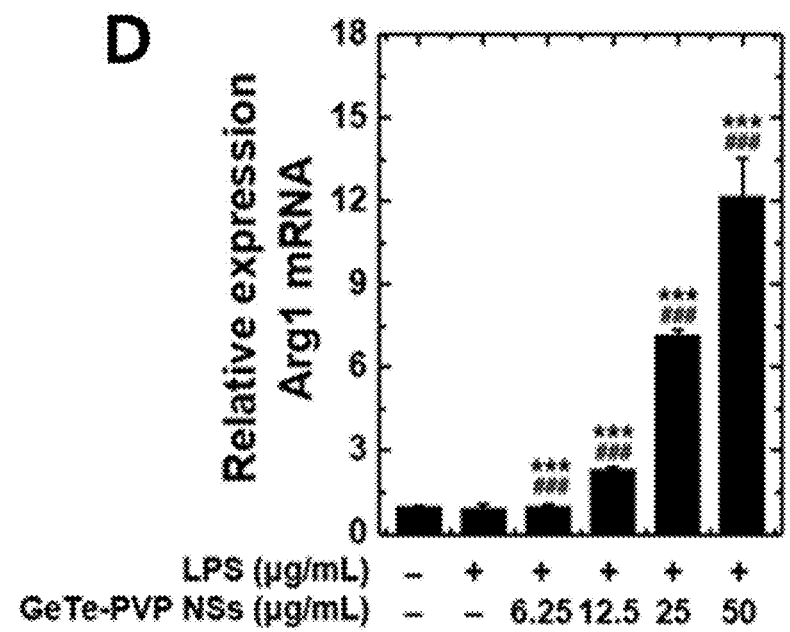
FIG. 12D illustrates the results of confirming the expression changes of Arg 1 (Arginase1) mRNA after treating lipopolysaccharide (LPS)—stimulated macrophage cells with GeTe-PVP NS.
Figure 12E:
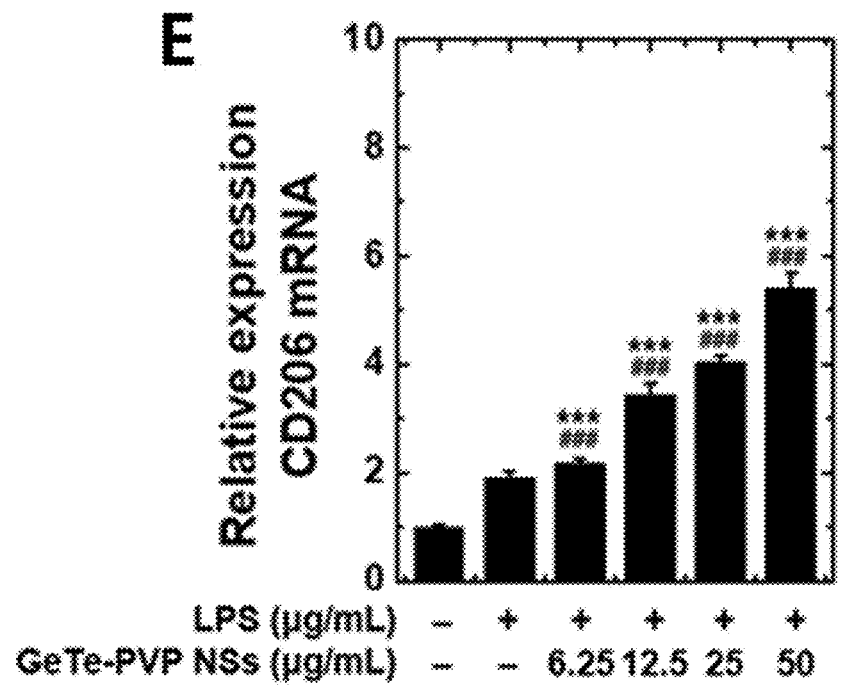
FIG. 12E illustrates the results of confirming the expression changes of CD 206 (Cluster of Differentiation 206) mRNA after treating lipopolysaccharide (LPS)—stimulated macrophage cells with GeTe-PVP NS.
Figure 12F:
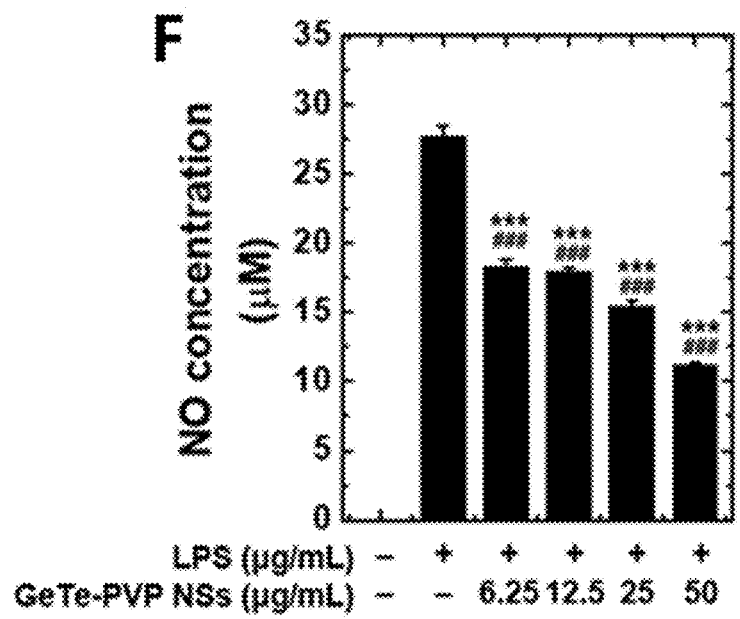
FIG. 12F illustrates the results of confirming the expression changes of nitro oxide (NO) mRNA after treating lipopolysaccharide (LPS)—stimulated macrophage cells with GeTe-PVP NS.

As a result of confirmation, it could be seen that the expression of pro-inflammatory factors decreased (FIGS. 12A, 12B and 12C) and the expression of anti-inflammatory factors increased depending on the treatment concentration of GeTe-PVP NSs (FIGS. 12D, 12E and 12F). This result means that GeTe-PVP NSs have excellent anti-inflammatory activity.

Example 5: In Vitro Anticancer Activity Assay of GeTe-PVP NSs

Figure 13A:
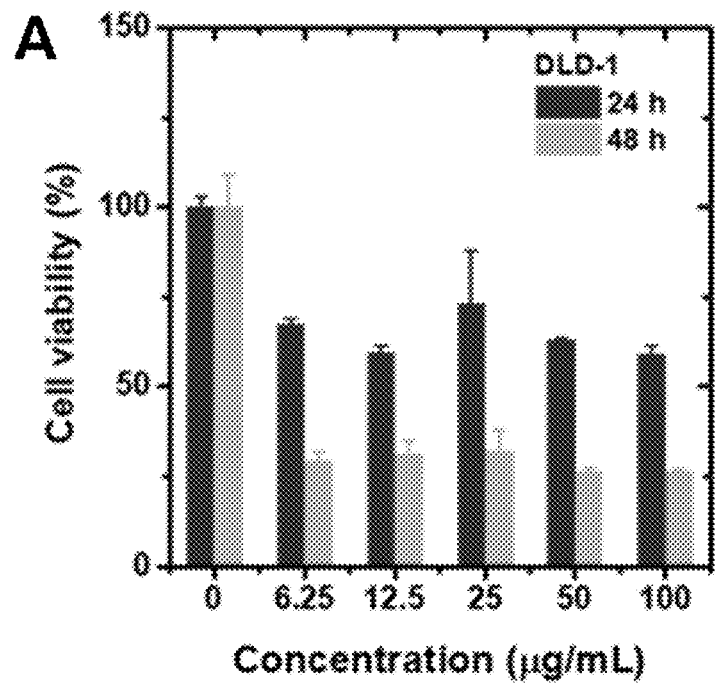
FIG. 13A illustrates the results of confirming cell viability according to treatment concentration and treatment time after treating colorectal cancer cell DLD-1 with GeTe-PVP NS.
Figure 13B:
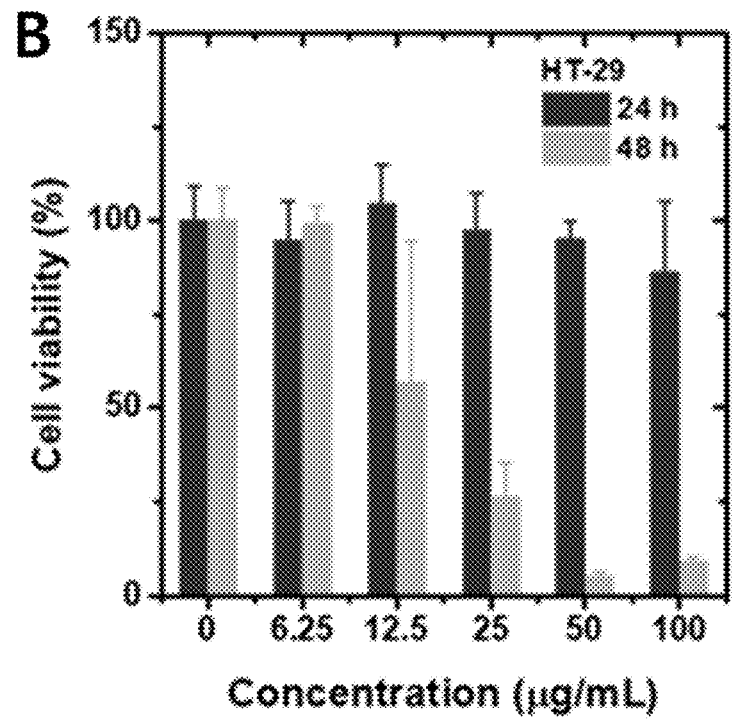
FIG. 13B illustrates the results of confirming cell viability according to treatment concentration and treatment time after treating colorectal cancer cell HT-29 with GeTe-PVP NS.
Figure 13C:
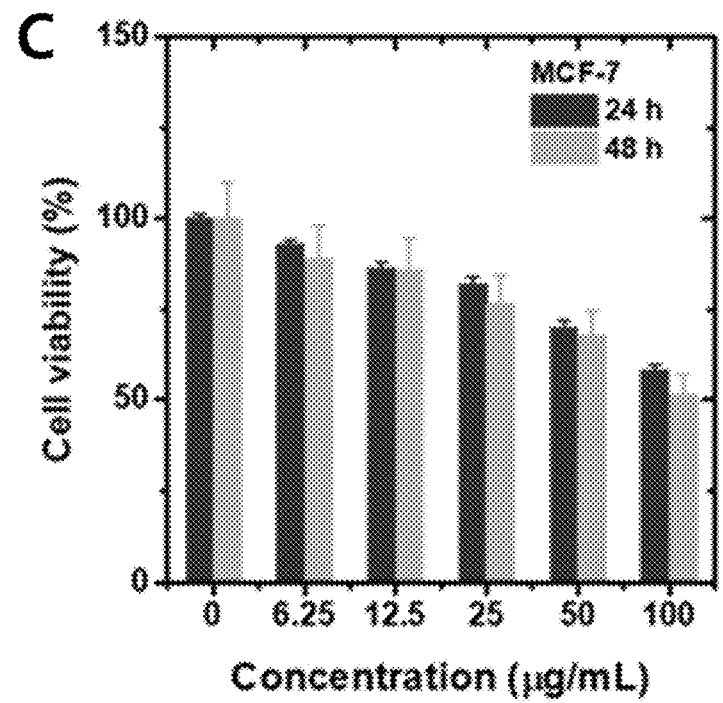
FIG. 13C illustrates the results of confirming cell viability according to treatment concentration and treatment time after treating breast cancer cell MCF-7 with GeTe-PVP NS.

Two types of colorectal cancer cells, DLD-1 and HT-29, and breast cancer cells, MCF-7, were treated with GeTe-PVP NSs at a concentration of 0 to 100 μg/ml and cultured for 24 or 48 hours, and cell activity was confirmed by CCK-8. As a result, unlike the results of Example 4 where GeTe-PVP NSs did not affect the viabilities of the four types of normal cells, it could be confirmed that GeTe-PVP NSs kill cancer cells (FIGS. 13A, 13B and 13C).

This is presumed to be due to the selective anti-cancer activity of Te caused by the generation of reactive oxygen species (ROS) in cancer cells. In the case of breast cancer treatment, when GeTe-PVP NSs are used as a combined treatment together with phototherapy using optical heat of Example 3, a more effective cancer treatment effect will be obtained.

Example 6: MSOT Imaging of Stomach and Intestine Using GeTe-PVP NSs

Figure 14:
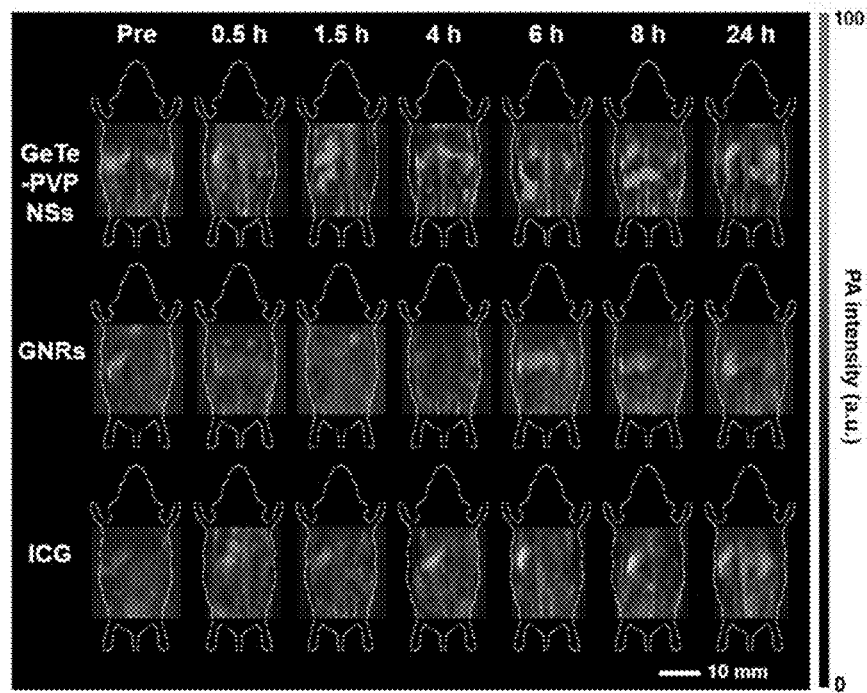
FIG. 14 is a photograph taken in the region of $\lambda$=6680 to 980 after administering GeTe-PVP NSs, gold nanorods or indocyanine green to Balb/C nude mice.

After GeTe-PVP NS (5 mg/kg, 100 μl), gold nanorods (5 mg/kg, 200 μl) and an ICG solution (5 mg/kg, 200 μl) to Balb/C nude mice, images were captured in a region of λ=680 to 980 nm and compared. As a result, it could be confirmed that not only clearer images of GeTe-PVP NSs could be obtained from experimental groups orally administered GeTe-PVP NSs compared to those of experimental groups orally administered gold nanorods or the ICG solution, but also GeTe-PVP NSs remained in the intestine for a longer period of time (FIG. 14).

Figure 15A:
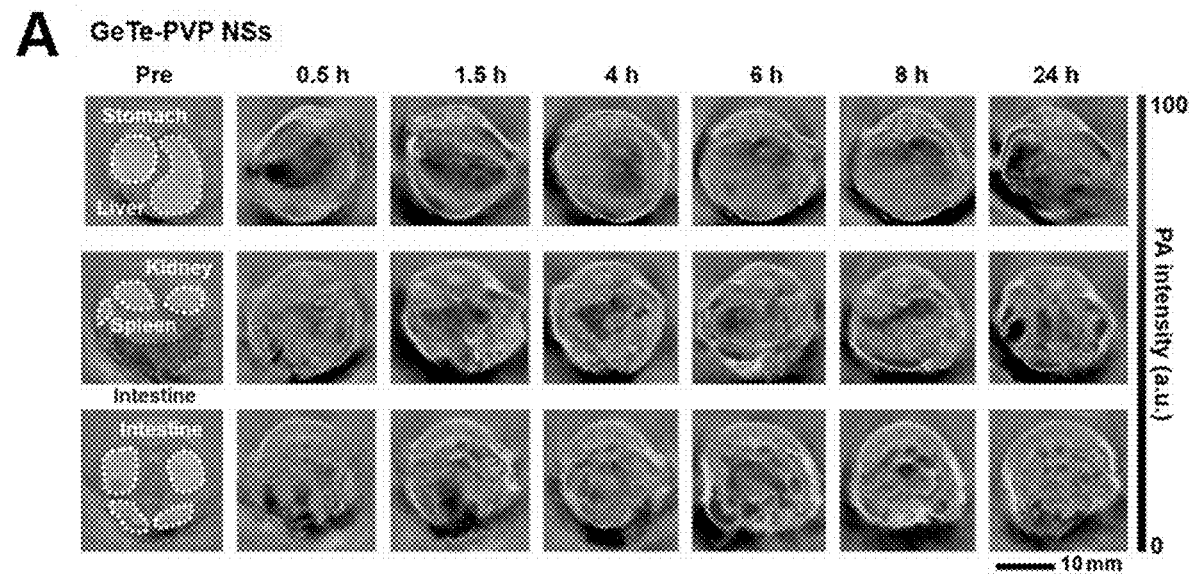
FIG. 15A is a set of photographs of each organ taken at predetermined times after administering GeTe-PVP NSs to Balb/C nude mice.
Figure 15B:
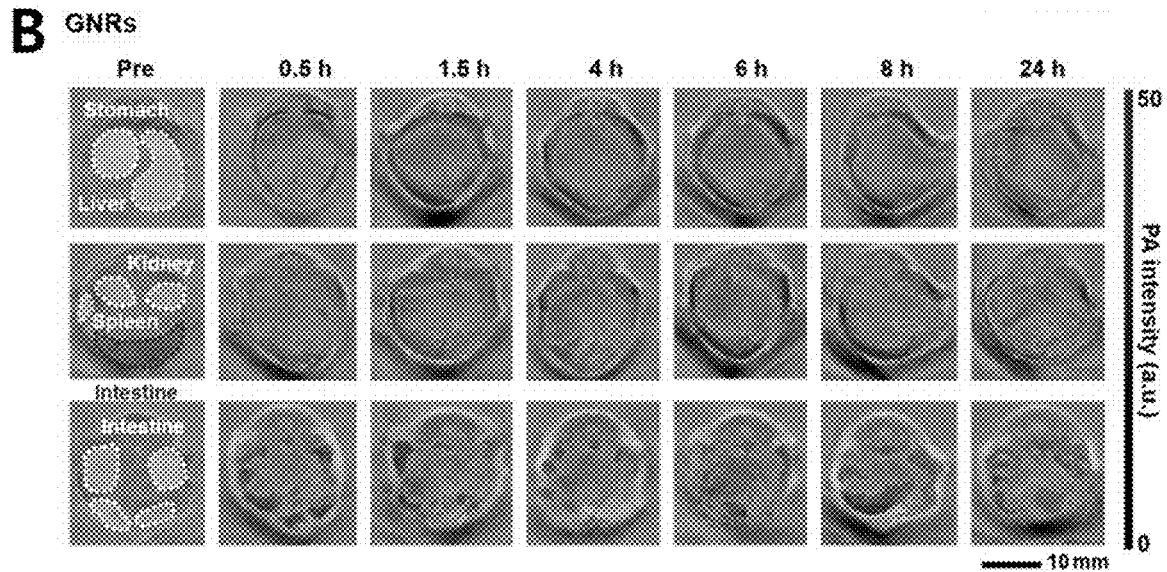
FIG. 15B is a set of photographs of each organ taken at predetermined times after administering gold nanorods to Balb/C nude mice.
Figure 15C:
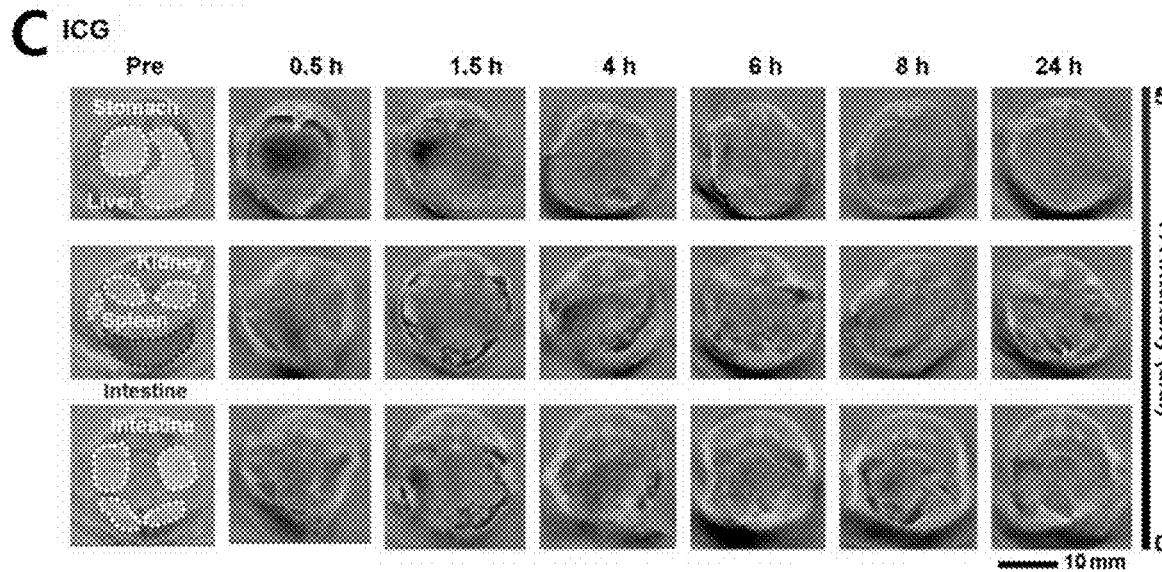
FIG. 15C is a set of photographs of each organ taken at predetermined times after administering indocyanine green to Balb/C nude mice.
Figure 16A:
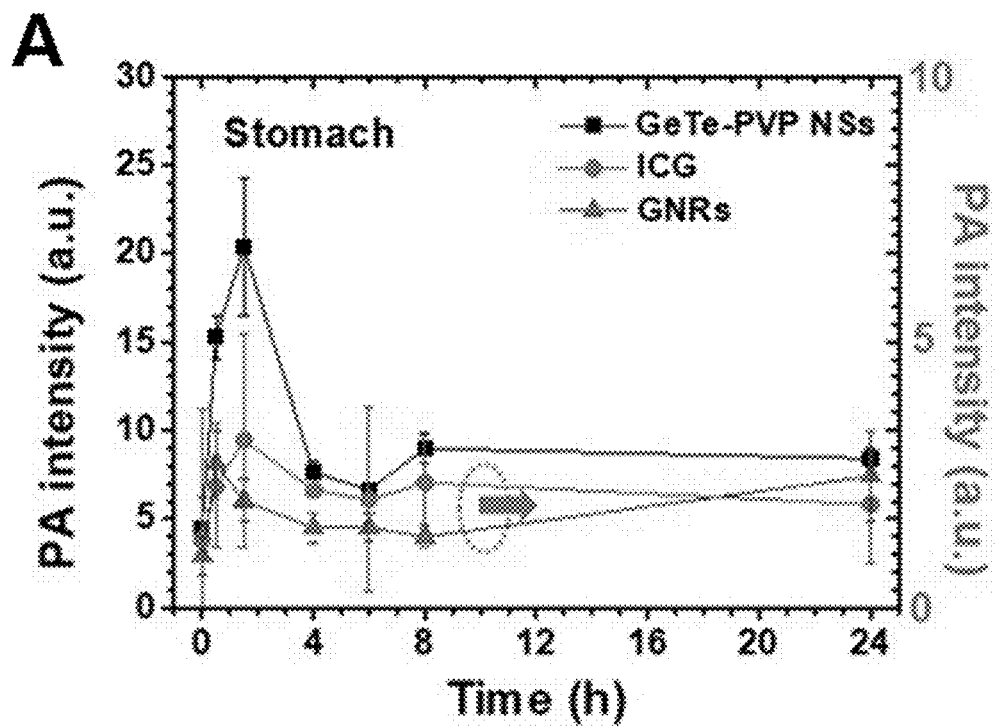
FIG. 16A illustrates the results of confirming the amounts remaining in the stomach at predetermined times after administering GeTe-PVP NSs, gold nanorods, or indocyanine green to Balb/C nude mice.
Figure 16B:
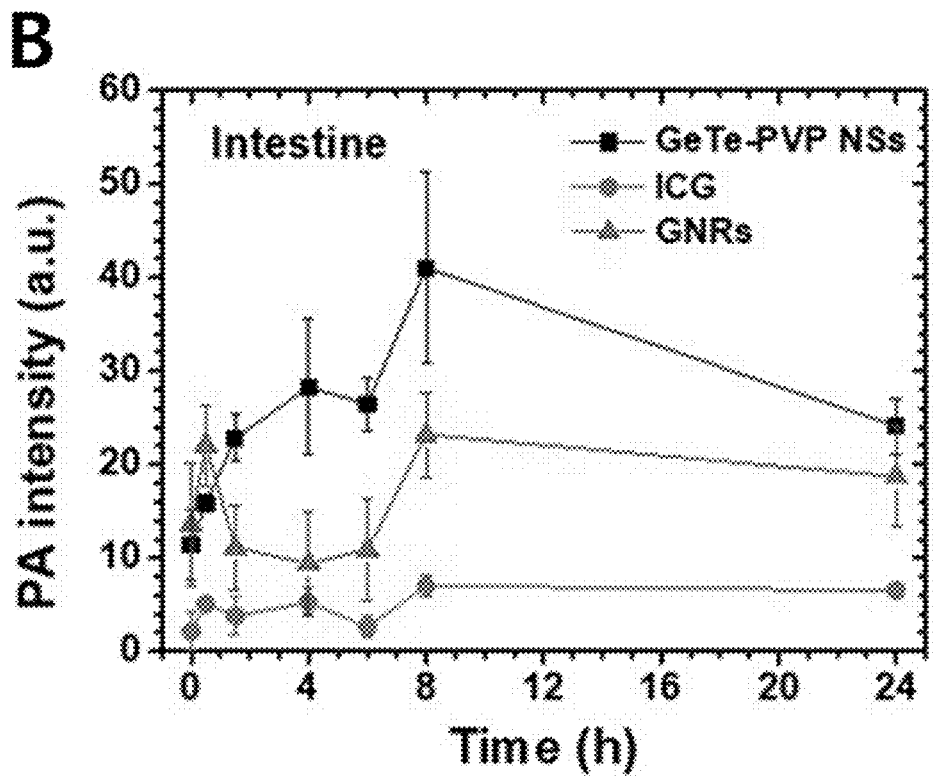
FIG. 16B illustrates the results of confirming the amounts remaining in the intestine at predetermined times after administering GeTe-PVP NSs, gold nanorods, or indocyanine green to Balb/C nude mice.

As a result of confirming images of each organ with MSOT, it was possible to confirm in vivo images of GeTe-PVP NSs, gold nanorods, and the ICG solution remaining in the stomach and intestine over time (FIG. 15). In addition, changes in the GeTe-PVP NSs, GNR, and ICG solution over time were confirmed using PA intensity. As a result, it could be confirmed that a larger amount of GeTe-PVP NSs remained in the gastrointestinal tract up to 2 hours after administration compared to gold nanorods and the ICG solution, and a larger amount remained in the intestines up to 24 hours after administration (FIGS. 16A and 16B).

Example 7: IVIS Fluorescence Imaging of Stomach and Intestine Using GeTe-PVP NSs After GeTe-PVP NSs (5 mg/kg, 100 μl) or an ICG solution (5 mg/kg, 200 μl) were orally administered, the mice were subjected to laparotomy at 1, 6, and 24 hours, and the biodistribution of GeTe-PVP NSs and the ICG solution was photographed with an in vivo imaging system (IVIS). Furthermore, the stomach, intestine, liver, lungs, pancreas, heart, and kidneys were removed at each time to confirm their biodistribution by fluorescence imaging with IVIS and quantify the amounts of GeTe-PVP NSs and ICG accumulated in each organ by FL intensity.

Figure 17A:
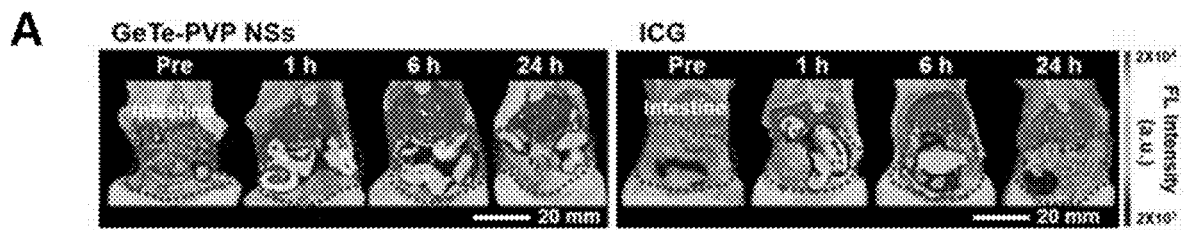
FIG. 17A illustrates the results of capturing the biodistribution of GeTe-PVP NS and an ICG solution by an in vivo imaging system (IVIS) at predetermined times after administering GeTe-PVP NSs or indocyanine green to Balb/C nude mice.
Figure 17B:
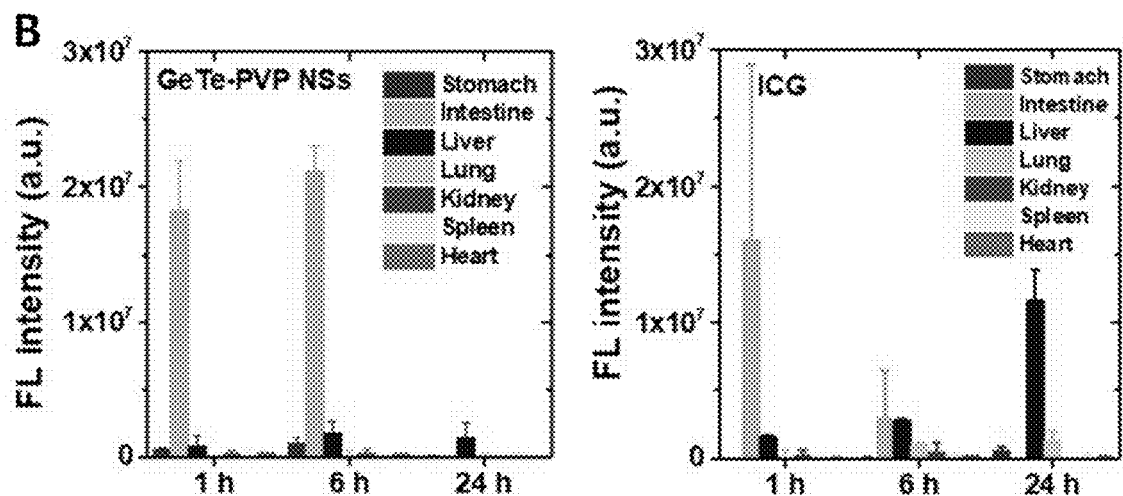
FIG. 17B illustrates the results of quantifying the biodistribution of GeTe-PVP NSs and an ICG solution by in vivo imaging system (IVIS) at predetermined times after administering GeTe-PVP NSs or indocyanine green to Balb/C nude mice.

As a result, it was confirmed that a large amount of GeTe-PVP NSs was accumulated in the intestine until 6 hours after administration, and a large amount of the ICG solution remained in the intestine until 1 hour after administration, but large amounts of GeTe-PVP NSs and the ICG solution were released from the intestine after 6 hours (FIGS. 17A and 17B).

Example 8: Confirmation of Biodistribution of GeTe-PVP NSs

Figure 18A:
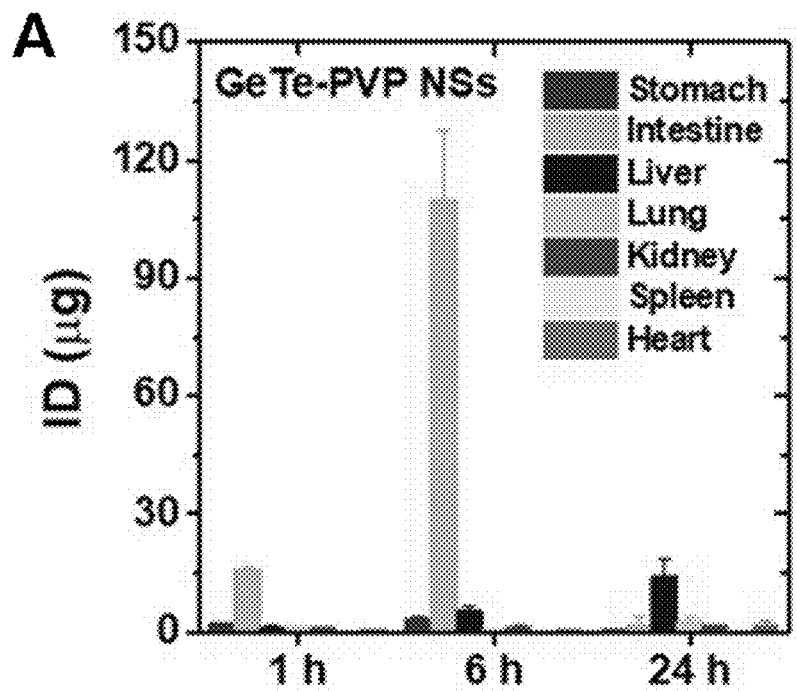
FIG. 18A illustrates the results of confirming the amount of GeTe-PVP NSs remaining in each organ at predetermined times after administering GeTe-PVP NSs to mice.
Figure 18B:
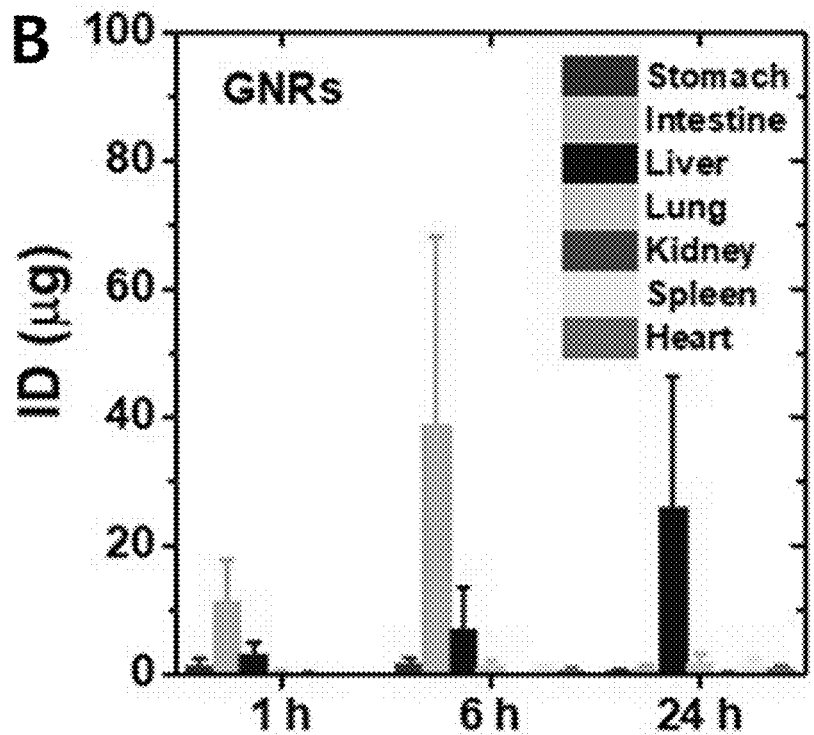
FIG. 18B illustrates the results of confirming the amount of gold nanorods remaining in each organ at predetermined times after administering gold nanorods to mice.

GeTe-PVP NSs (5 mg/kg, 100 μl) or gold nanorods (5 mg/kg, 200 μl) were orally administered to mice. Thereafter, in order to investigate a biodistribution, the stomach, intestine, liver, lungs, pancreas, heart, and kidneys were excised at 1 hour, 6 hours, and 24 hours after administration, and the biodistribution was confirmed by ICP-MS. As a result of confirmation, it could be seen that a large amount of GeTe-PVP NSs remained in the intestine 6 hours after oral administration, and it could be confirmed that GeTe-PVP NSs were present in a larger amount than the gold nanorods. 24 hours after oral administration, it could be confirmed that large amounts of GeTe-PVP NSs and gold nanorods were released from the body (FIGS. 18A and 18B; ID=injected dose).

Example 9: Evaluation of IBD Therapeutic Effect Using GeTe-PVP NSs

Since the in vitro anti-inflammatory effect of GeTe-PVP NSs was confirmed in Example 4, the therapeutic effect of GeTe-PVP NSs on inflammatory bowel disease was confirmed in an inflammatory bowel disease model.

Figure 19:
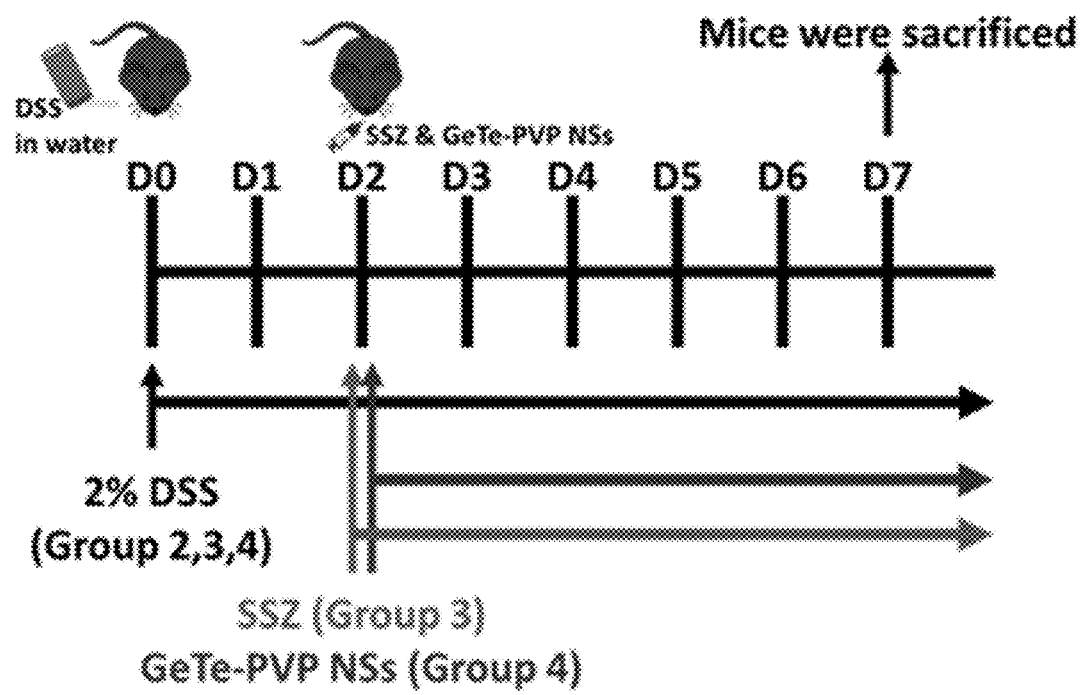
FIG. 19 schematically shows the process of making an animal model of inflammatory bowel disease.

9-1. Establishment of Inflammatory Bowel Disease Model 7- to 8-week-old male C57BL/6 mice (Orient Bio Inc.; Seongnam, Korea) were used for the experiments. Colitis was induced by allowing an acute inflammatory bowel disease model to ingest drinking water to which 2% dextran sodium sulfate (DSS; MP Biochemical, Irvine, Ca, USA) was added for 7 days. A normal control group was allowed to ingest the same amount of water for the same time (FIG. 19).

The experimental groups were classified into the following four groups (Table 1): a normal control group (Group 1, n=8), a group in which colitis is induced by DSS (Group 2, n=8), a group in which sulfasalazine (SAZ), which is a common therapeutic agent, was administered to a DSS-induced colitis model (Group 3, n=8, SAZ=200 mg/kg/day), and a group in which GeTe-PVP NSs were administered to a DSS-induced colitis model (Group 4, n=8, GeTe-PVP NS=5 mg/kg/day).

TABLE 1

| Group (n = 8) | Sample | Dosage |
|---|---|---|
| Group 1 | PBS | |
| Group 2 | dextran sodium sulfate (DSS) | 2 wt % * 8 days |
| Group 3 | dextran sodium sulfate (DSS) + Sulfasalazine (SAZ) | 2 wt % * 8 days + 200 mg/kg * 6 days |
| Group 4 | dextran sodium sulfate (DSS) + GeTe PVP NS | 2 wt % * 8 days + 5 mg/kg * 6 days |

Figure 20A:
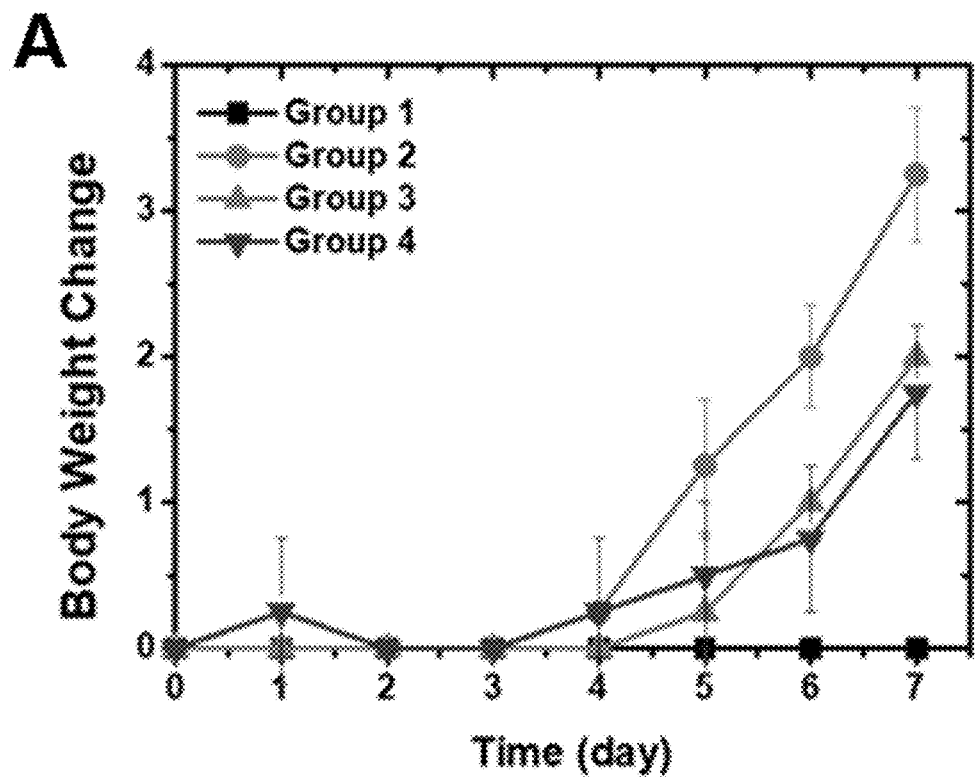
FIG. 20A illustrates the results of confirming the body weight loss index while administering materials corresponding to each group to mice: Group 1—normal control group (Group1, n=8); Group 2—inflammatory bowel disease-induced group; Group 3—inflammatory bowel disease induction+sulfasalazine (SAZ) administration; and Group 4—inflammatory bowel disease induction+GeTe-PVP NS administration.
Figure 20B:
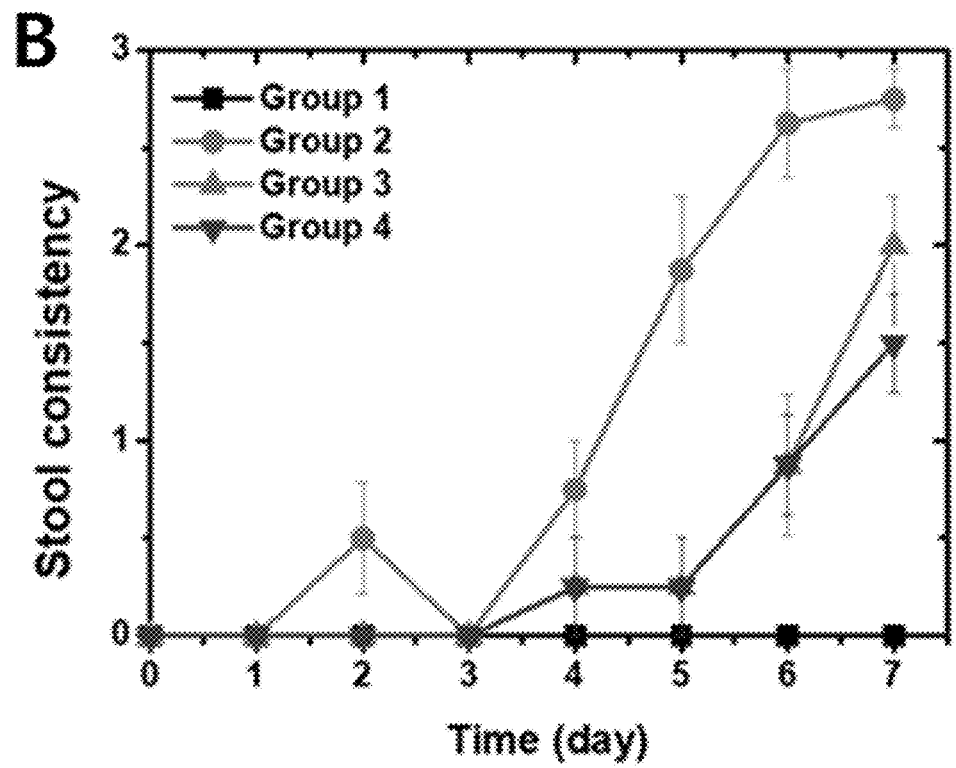
FIG. 20B illustrates the results of confirming the stool consistency while administering materials corresponding to each group to mice: Group 1—normal control group (Group 1, n=8); Group 2—inflammatory bowel disease-induced group; Group 3—inflammatory bowel disease induction+sulfasalazine (SAZ) administration; and Group 4—inflammatory bowel disease induction+GeTe-PVP NS administration.
Figure 20C:
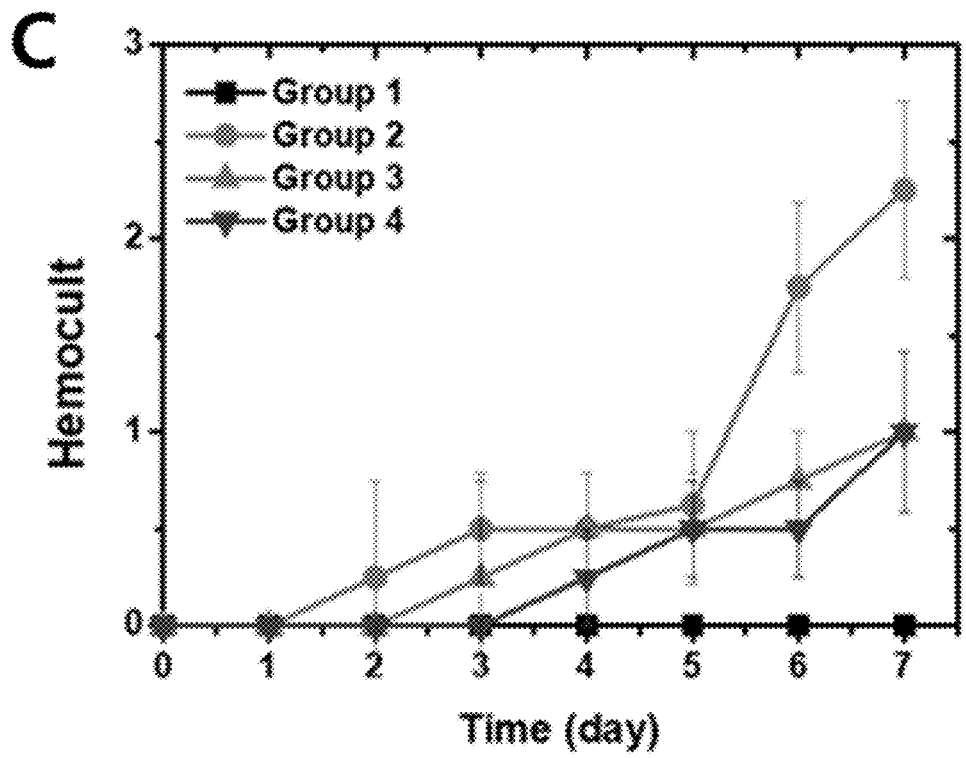
FIG. 20C illustrates the results of confirming the rectal bleeding (hemocult) while administering materials corresponding to each group to mice: Group 1—normal control group (Group 1, n=8); Group 2—inflammatory bowel disease-induced group; Group 3—inflammatory bowel disease induction+sulfasalazine (SAZ) administration; and Group 4—inflammatory bowel disease induction+GeTe-PVP NS administration.

9-2. Evaluation of Macroscopic Therapeutic Effect Including Disease Activity Measure Body weight changes and the disease activity index (DAI) of mice were confirmed every day for 7 days. Each score of weight loss index (0 to 4; FIG. 20A), rectal bleeding observed with the naked eye in the stool or anus (0 to 3; FIG. 20C), and stool consistency (0 to 3; FIG. 20B) is summed to evaluate the disease activity index on a 10-point scale (FIG. 20D). [Stevceva L, Pavli P, Husband A, Ramsay A, Doe WF. Dextran sulphate sodium-induced colitis is ameliorated in interleukin 4 deficient mice. Genes Immun 2001; 2:309-316.]

Figure 20D:
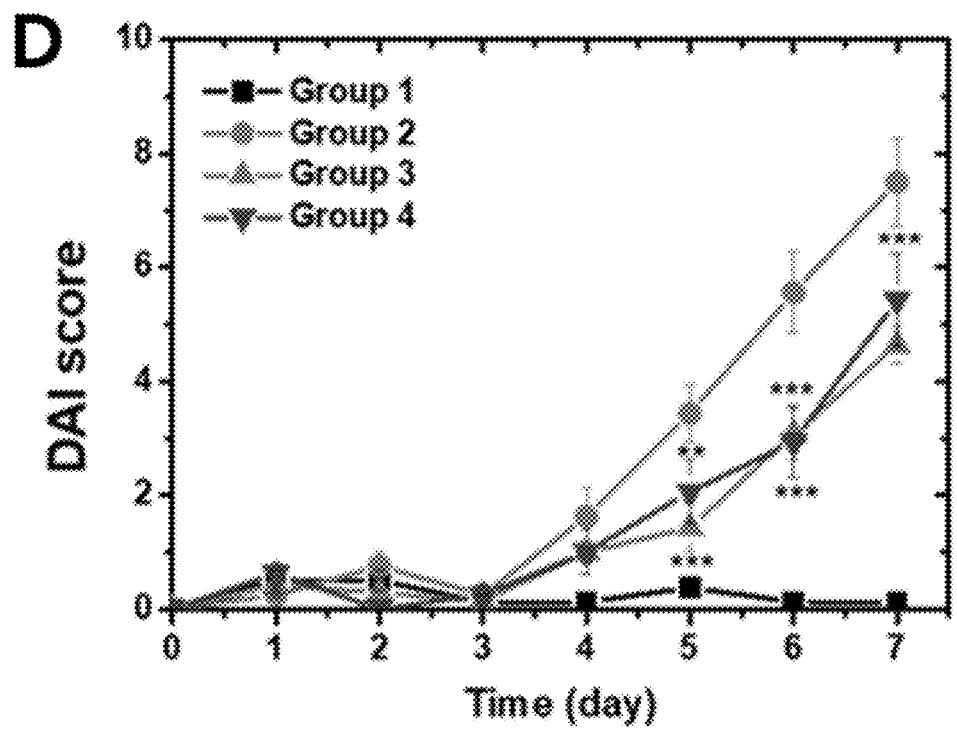
FIG. 20D illustrates the results of confirming the disease activity index (DAI) while administering materials corresponding to each group to mice: Group 1—normal control group (Group 1, n=8); Group 2—inflammatory bowel disease-induced group; Group 3—inflammatory bowel disease induction+sulfasalazine (SAZ) administration; and Group 4—inflammatory bowel disease induction+GeTe-PVP NS administration.

As a result of evaluation, Group 2 had severe intestinal bleeding and Group 4 had relatively minor bleeding (FIG. 20C). When the DAI was compared, Group 2 showed a continuous increase in DAI during the administration period, but Groups 3 and 4 showed a tendency to have a lower DAI compared to Group 2. The DAI was significantly lower in Group 4 compared to Group 3 on day 7 of administration (FIG. 20D).

Figure 21:
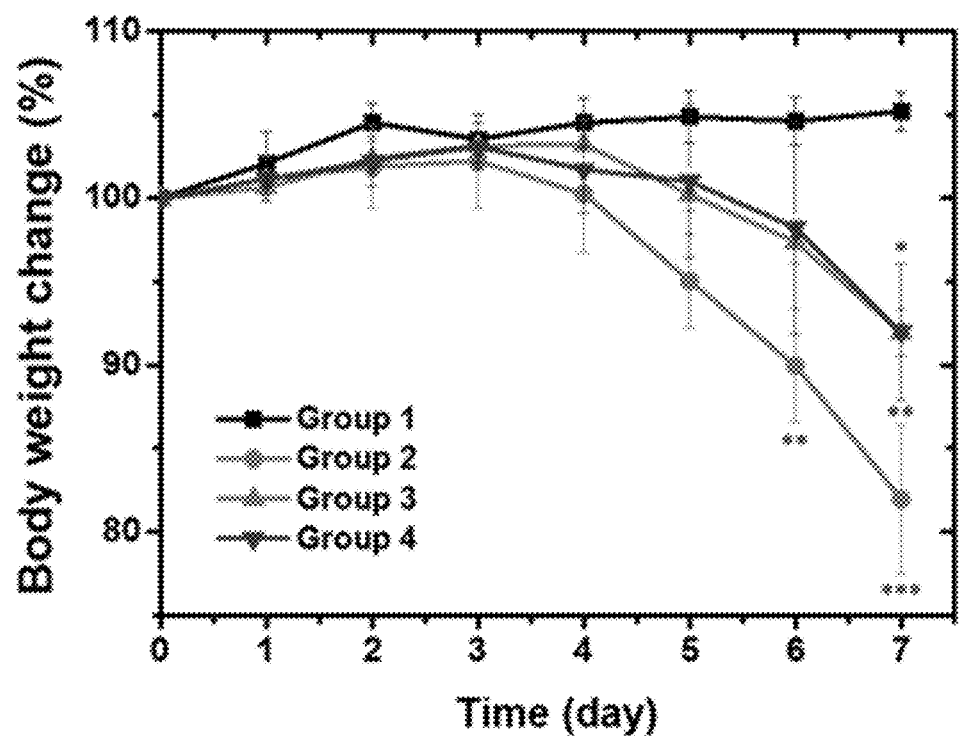
FIG. 21 illustrates the results of quantifying the degree of body weight loss while administering materials corresponding to each group to mice: Group 1—normal control (Group1, n=8); Group 2—inflammatory bowel disease-induced group; Group 3—inflammatory bowel disease induction+sulfasalazine (SAZ) administration; and Group 4—inflammatory bowel disease induction+GeTe-PVP NS administration.

Further, in Group 1, a sustained body weight gain was confirmed for 7 days, whereas in Group 2, a body weight loss was confirmed from day 4 of administration. A body weight loss was confirmed in Groups 2 and 4 after day 5 of administration, but it could be confirmed that the body weight was slowly decreased compared to Group 2 (FIG. 21).

Figure 22A:
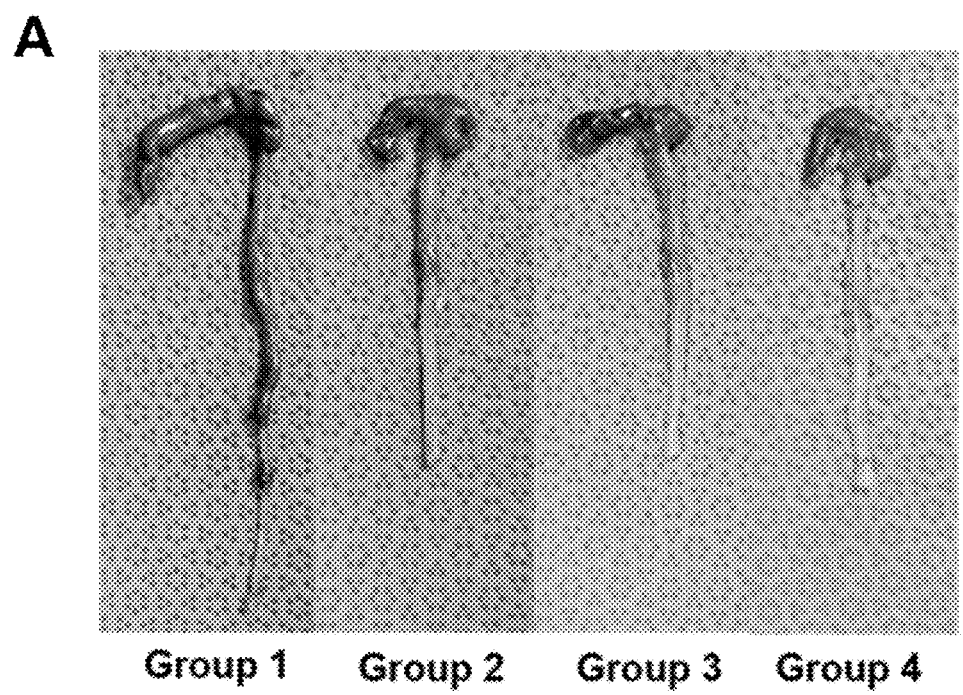
FIG. 22A is a photograph taken by removing the intestine after administering materials corresponding to each group to mice: Group 1—normal control group (Group 1, n=8); Group 2—inflammatory bowel disease-induced group; Group 3—inflammatory bowel disease induction+sulfasalazine (SAZ) administration; and Group 4—inflammatory bowel disease induction+GeTe-PVP NS administration.
Figure 22B:
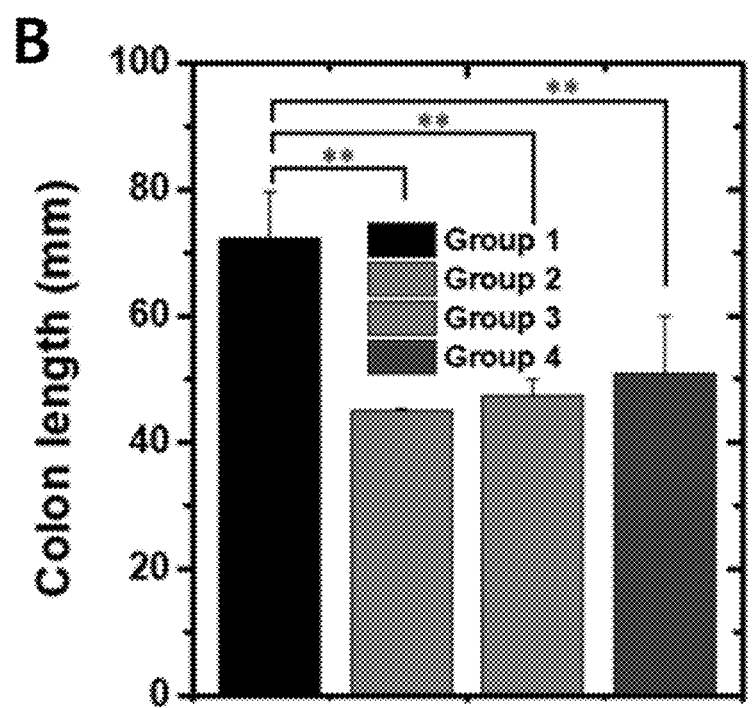
FIG. 22B illustrates the results of quantifying the length of the excised intestine: Group 1—normal control group (Group1, n=8); Group 2—inflammatory bowel disease-induced group; Group 3—inflammatory bowel disease induction+sulfasalazine (SAZ) administration; and Group 4—inflammatory bowel disease induction+GeTe-PVP NS administration.

After the corresponding sample administration was completed, the mice were sacrificed by cervical dislocation and the intestine from the cecum to the anus was excised to measure the length of the intestine. As a result, the average colorectal length in Group 1 was 72.2 mm, while the average colorectal length in Group 2 was 44.8 mm, which was significantly shorter compared to Group 1. In contrast, Group 4 had an average colorectal length of 50.9 mm, which was longer compared to Group 2 (FIGS. 22A and 22B).

9-3. Histological Evaluation of Therapeutic Effect

Tissue specimens were obtained from the proximal and distal regions of the excised intestine, fixed in formalin, and stained with hematoxylin-eosin and periodic acid-schiff (PAS).

Figure 23A:
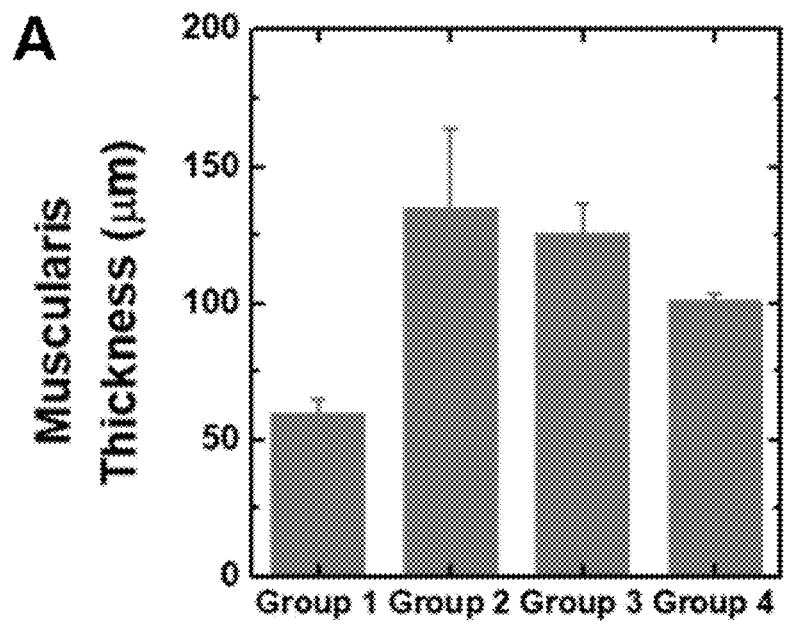
FIG. 23A illustrates the results of confirming the thickness of the intestine in the proximal and distal regions of the excised intestine: Group 1—normal control group (Group 1, n=8); Group 2—inflammatory bowel disease-induced group; Group 3—inflammatory bowel disease induction+sulfasalazine (SAZ) administration; and Group 4—inflammatory bowel disease induction+GeTe-PVP NS administration.
Figure 23B:
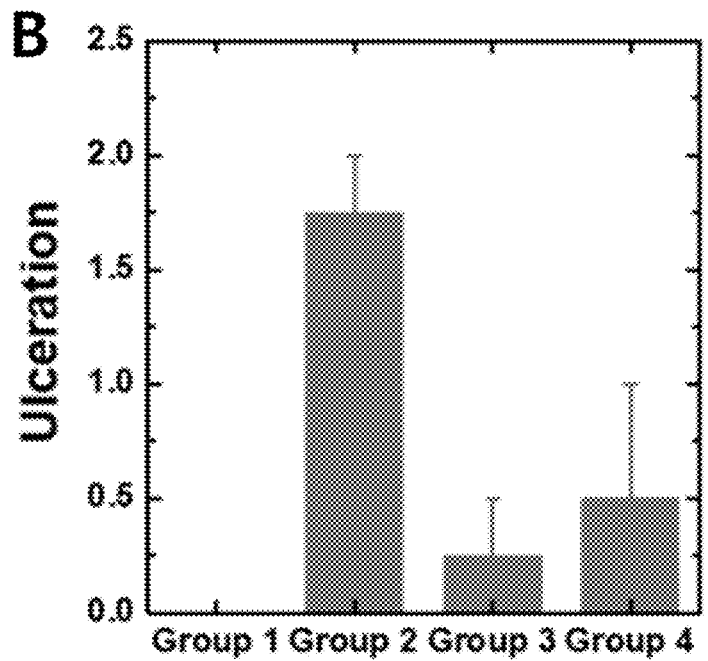
FIG. 23B illustrates the results of confirming the degree of inflammation in the proximal and distal regions of the excised intestine: Group 1—normal control group (Group 1, n=8); Group 2—inflammatory bowel disease-induced group; Group 3—inflammatory bowel disease induction+sulfasalazine (SAZ) administration; and Group 4—inflammatory bowel disease induction+GeTe-PVP NS administration.
Figure 23C:
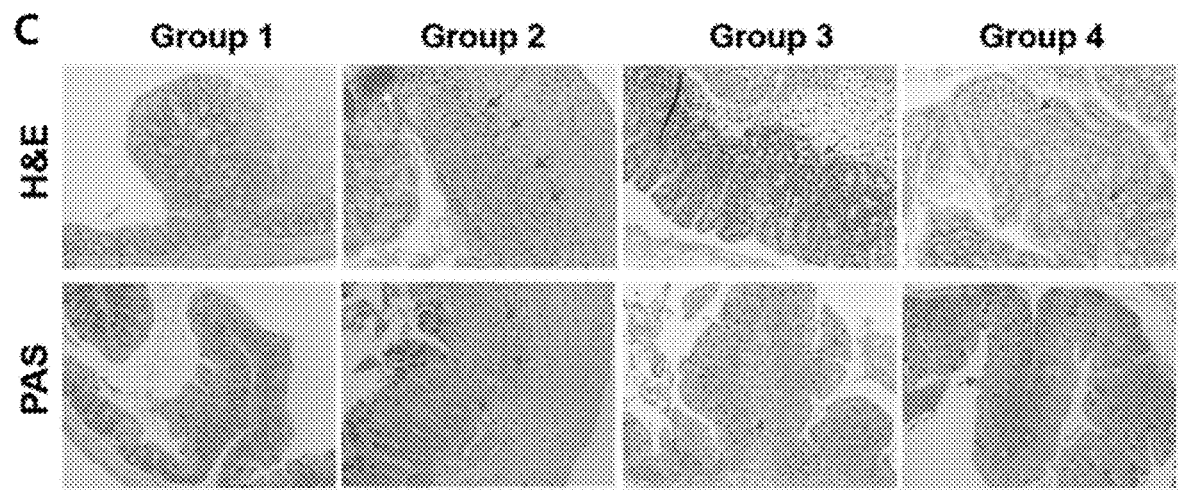
FIG. 23C illustrates the results of confirming the degree of tissue deformation in the proximal and distal regions of the excised intestine: Group 1—normal control group (Group 1, n=8); Group 2—inflammatory bowel disease-induced group; Group 3—inflammatory bowel disease induction+sulfasalazine (SAZ) administration; and Group 4—inflammatory bowel disease induction+GeTe-PVP NS administration.

As a result of staining, the thickness of the intestine became thicker in Group 2 compared to Group 1, and inflammatory findings of more than moderate severity and deformation of intestinal tissue were also observed. However, Groups 3 and 4 had similar intestinal tissue morphology to Group 1, and many inflammatory findings were not found (FIGS. 23A, 23B and 23C).

Figure 24:
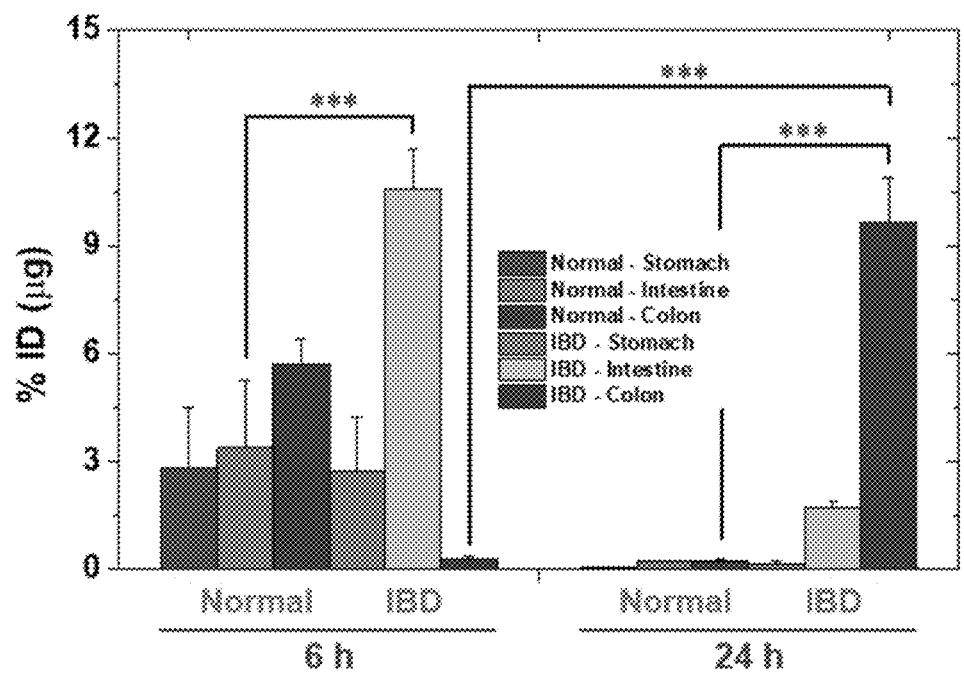
FIG. 24 illustrates the results of confirming the amounts of GeTe-PVP NSs remaining in the stomach, small intestine and large intestine at predetermined times after administering GeTe-PVP NSs to normal mice and inflammatory bowel disease-induced mice.

9-4. Evaluation of Targeting and Retention of GeTe-PVP NSs in Inflammatory Bowel Disease Model and General Model GeTe-PVP NSs were orally administered to inflammatory bowel disease model mice and normal mice. The targeting and retention of the inflammatory site of GeTe-PVP NSs were evaluated by ICP-MS in the stomach, small intestine, and large intestine at 6 and 24 hours after administration. 6 hours after oral administration, more GeTe-PVP NSs were found in the small intestine of inflammatory bowel disease mice (IBD) compared to normal mice. 24 hours after oral administration, GeTe-PVP NSs were scarcely found in the stomach, small intestine, and large intestine of normal mice. However, it was confirmed that 9.6% of the administered GeTe-PVP NSs remained in the large intestine in inflammatory bowel disease model mice (FIG. 24). This result means that GeTe-PVP NSs can target the inflammatory site to stay in the corresponding site for a long time in the inflammatory bowel disease model.

Example 10: Evaluation of GeTe-PVP NS Biocompatibility

After a 1 mg/ml GeTe-PVP NS solution was orally administered to Balb/C mice (OrientBio Inc.; Seongnam, Korea), each organ and blood were isolated and analyzed over time.

Blood analysis items were as follows: alkaline phosphatase (ALP), alanine aminotransferase (ALT), aspartate aminotransferase (AST), total protein (TP) count, white blood cells (WBC), red blood cells (RBC), mean corpuscular hemoglobin concentration (MCH), platelets (PLT), lymphocytes (LY), blood urea nitrogen (BUN), creatinine (CRE), hemoglobin (Hb), mean corpuscular volume (MCV), monocytes (MO) and hematocrit (HCT).

Figure 25:
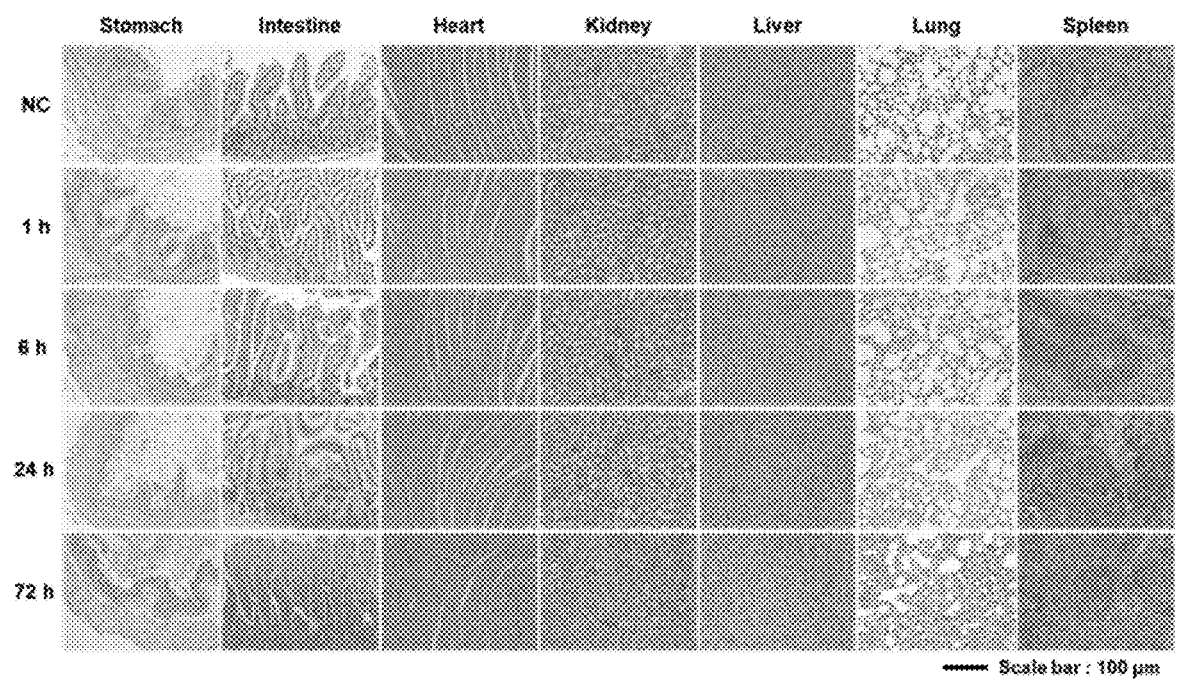
FIG. 25 illustrates the results of tissue staining by isolating each organ at predetermined times after administering a high concentration of GeTe-PVP NS to mice.
Figure 26A:
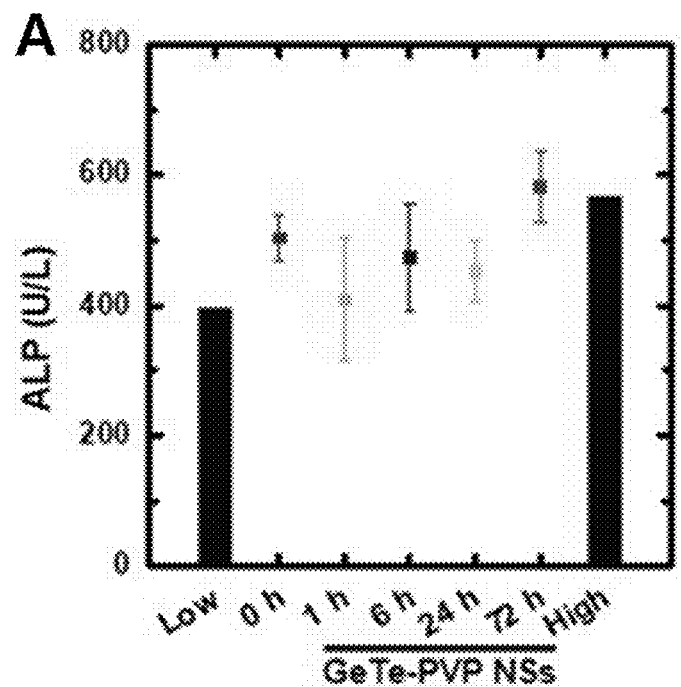
FIG. 26A illustrates the results of analyzing the level of alkaline phosphatase (ALP) in blood after administering a high concentration of GeTe-PVP NS to mice.
Figure 26B:
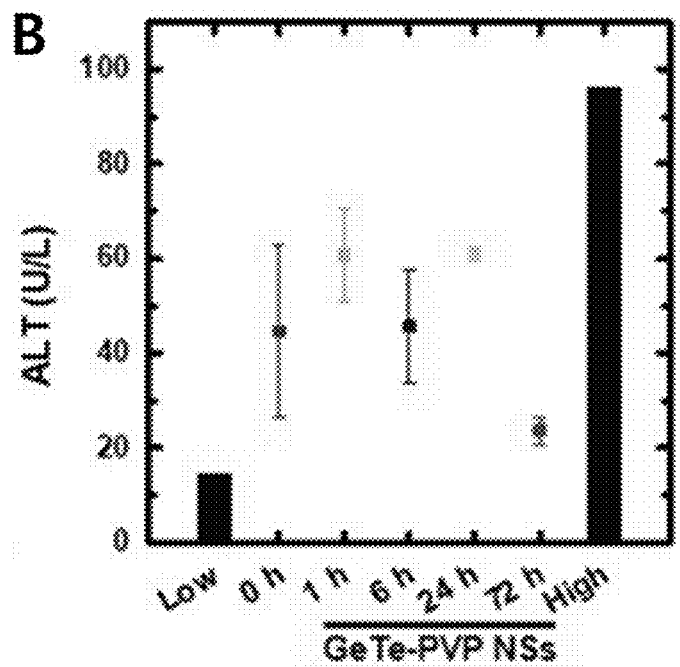
FIG. 26B illustrates the results of analyzing the level of alanine aminotransferase (ALT) in blood after administering a high concentration of GeTe-PVP NS to mice.
Figure 26C:
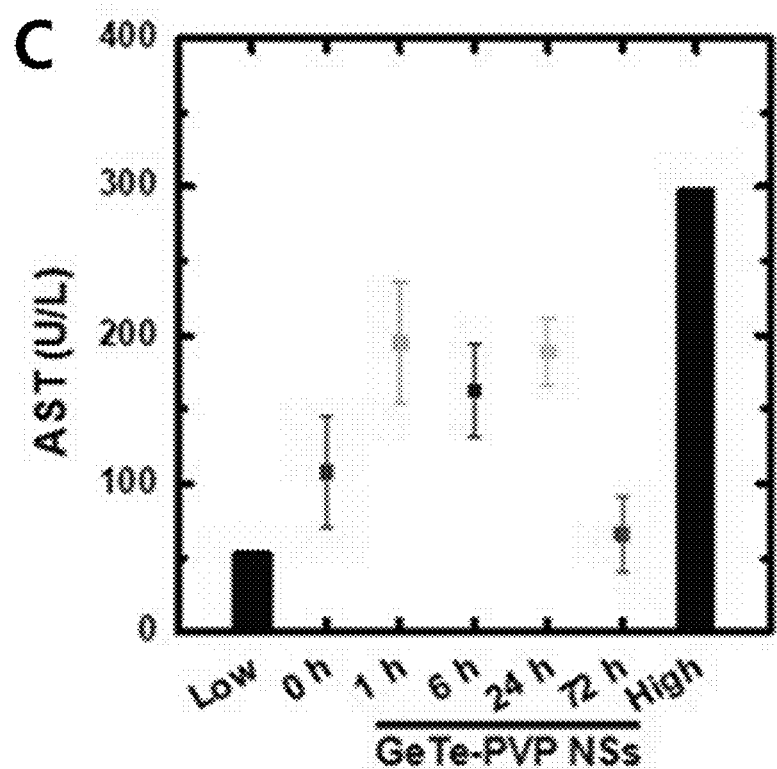
FIG. 26C illustrates the results of analyzing the level of aspartate aminotransferase (AST) in blood after administering a high concentration of GeTe-PVP NS to mice.
Figure 26D:
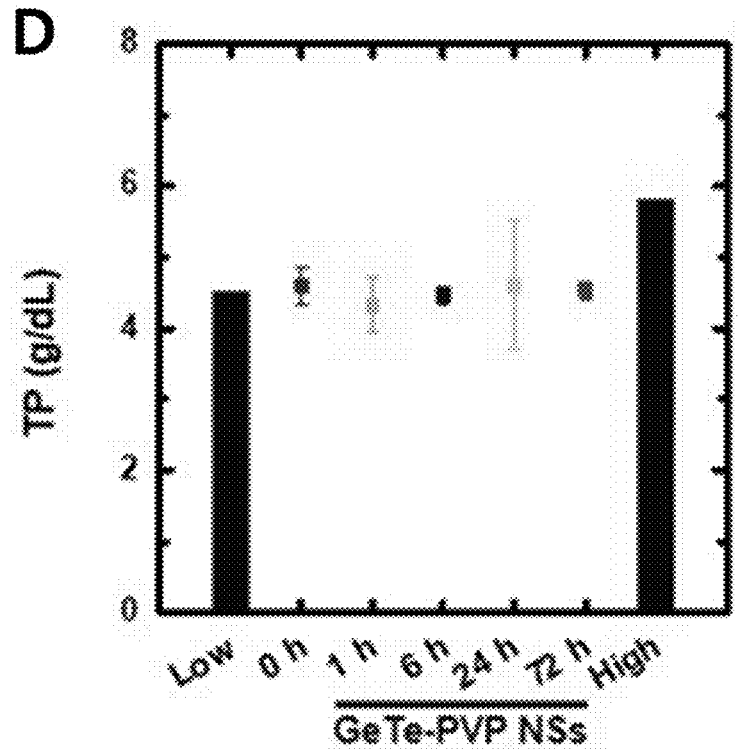
FIG. 26D illustrates the results of analyzing the level of total protein (TP) in blood after administering a high concentration of GeTe-PVP NS to mice.
Figure 26E:
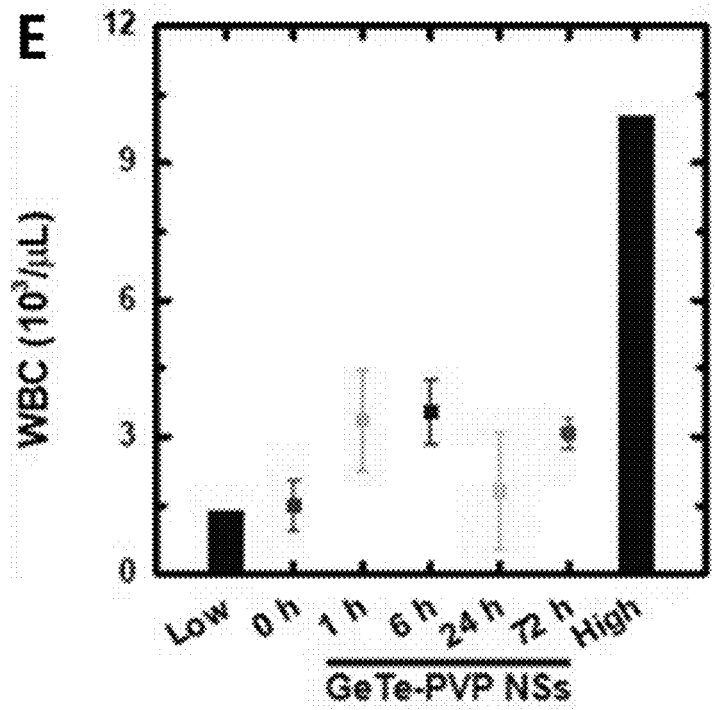
FIG. 26E illustrates the results of analyzing the level of white blood cells (WBC) in blood after administering a high concentration of GeTe-PVP NS to mice.
Figure 26F:
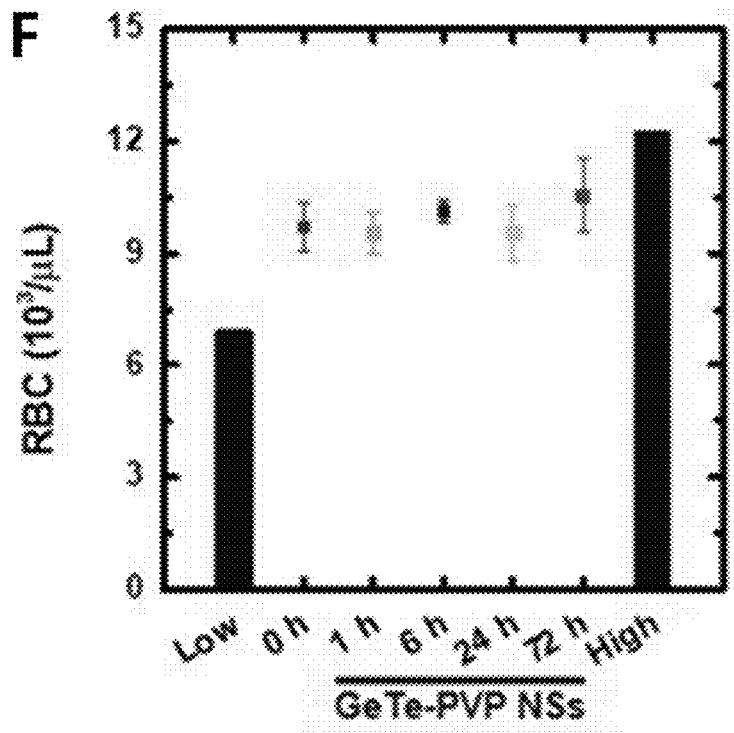
FIG. 26F illustrates the results of analyzing the level of red blood cells (RBC) in blood after administering a high concentration of GeTe-PVP NS to mice.
Figure 26G:
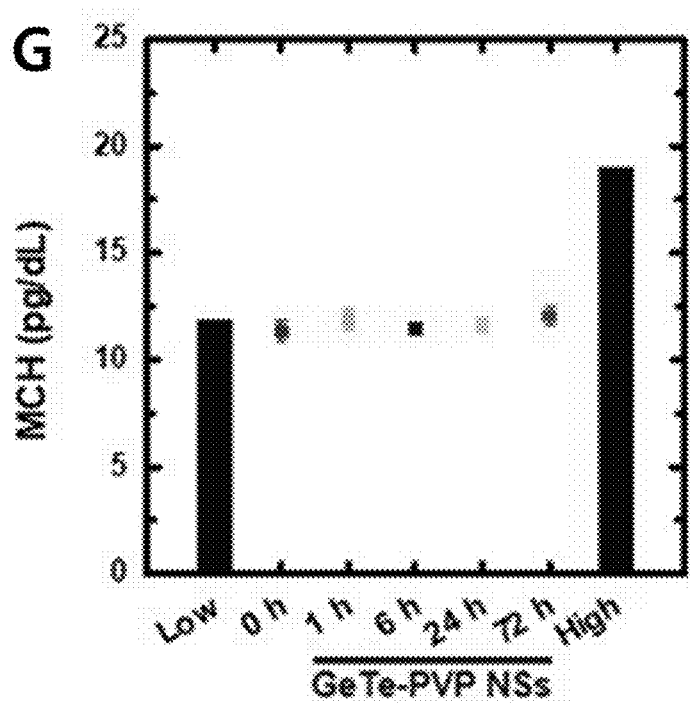
FIG. 26G illustrates the results of analyzing the level of mean corpuscular hemoglobin concentration (MCH) in blood after administering a high concentration of GeTe-PVP NS to mice.
Figure 26H:
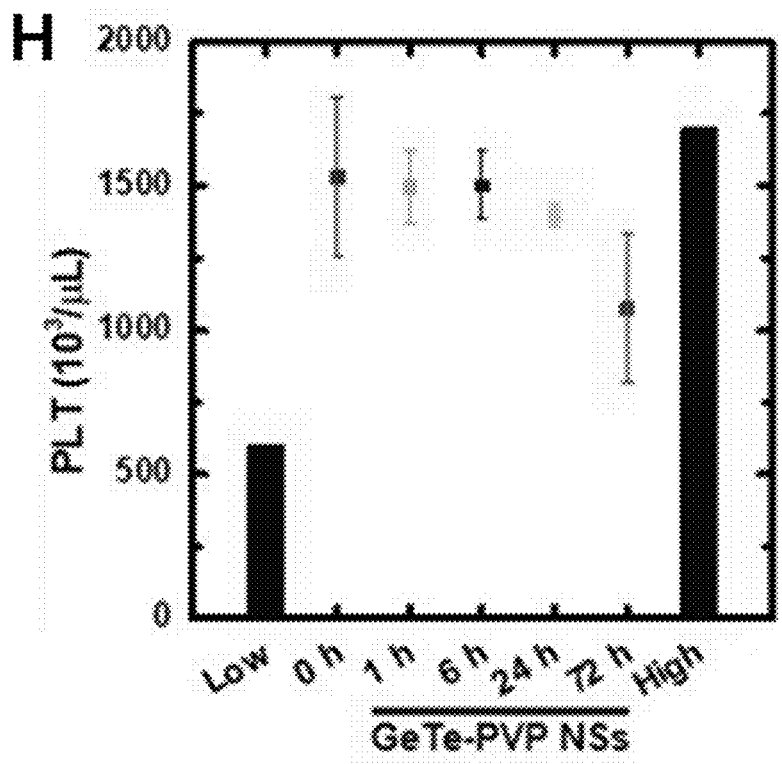
FIG. 26H illustrates the results of analyzing the level of platelets (PLT) in blood after administering a high concentration of GeTe-PVP NS to mice.
Figure 26I:
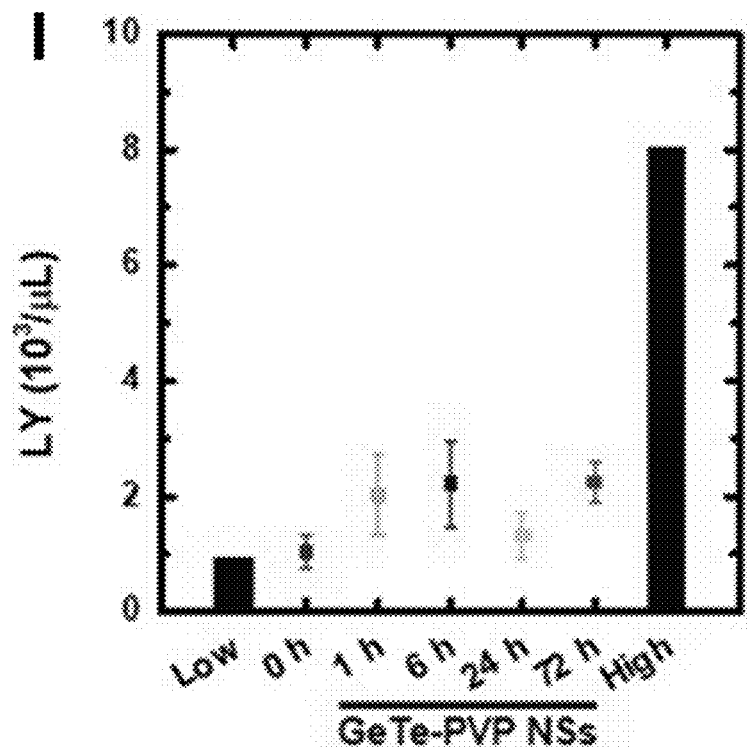
FIG. 26I illustrates the results of analyzing the level of lymphocytes (LY) in blood after administering a high concentration of GeTe-PVP NS to mice.
Figure 27A:
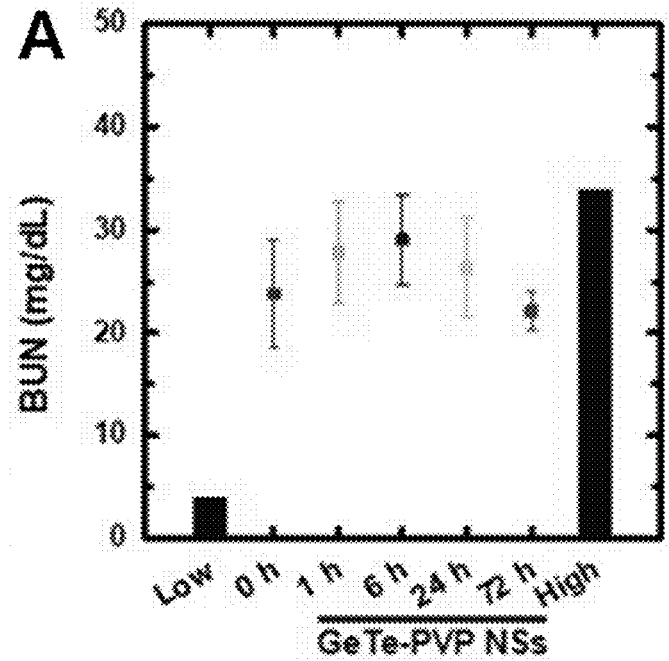
FIG. 27A illustrates the results of analyzing the level of blood urea nitrogen (BUN) in blood after administering a high concentration of GeTe-PVP NS to mice.
Figure 27B:
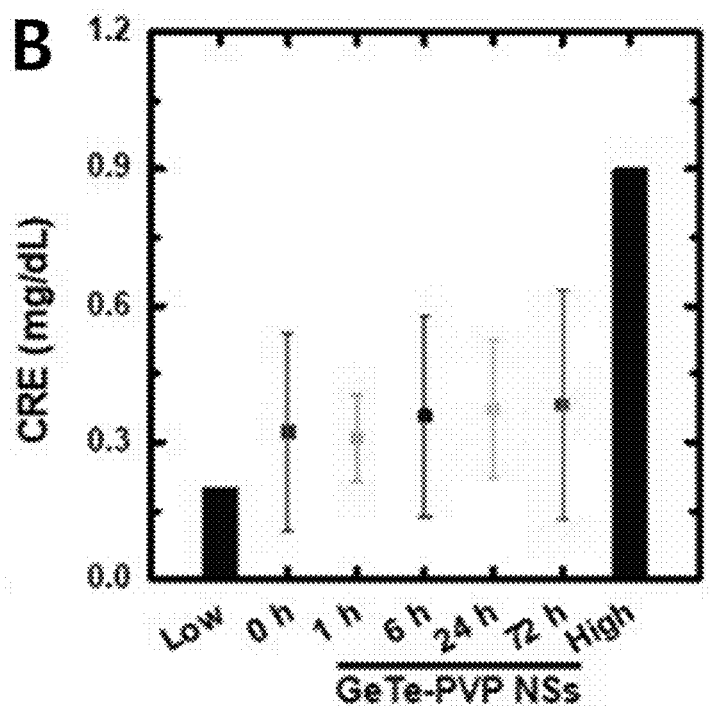
FIG. 27B illustrates the results of analyzing the level of creatinine (CRE) in blood after administering a high concentration of GeTe-PVP NS to mice.
Figure 27C:
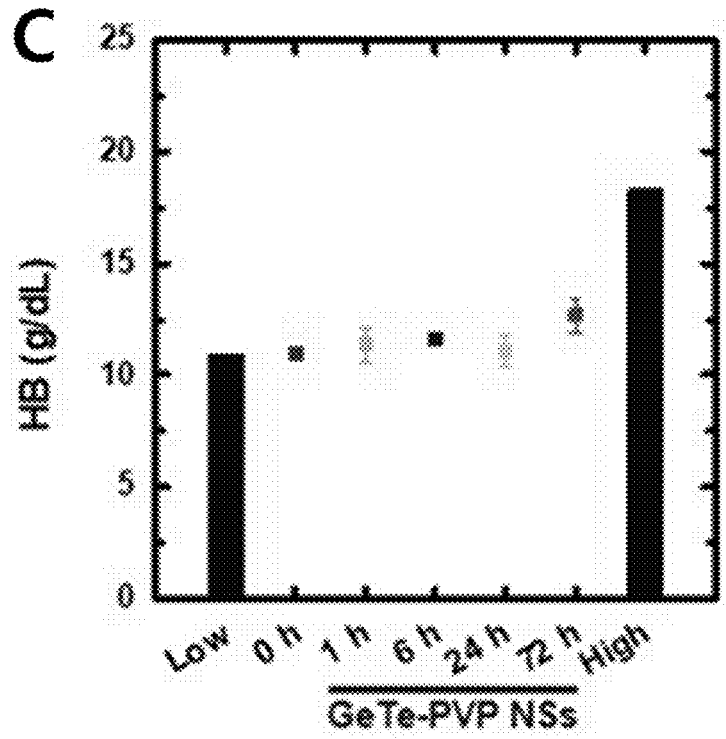
FIG. 27C illustrates the results of analyzing the level of hemoglobin (Hb) in blood after administering a high concentration of GeTe-PVP NS to mice.
Figure 27D:
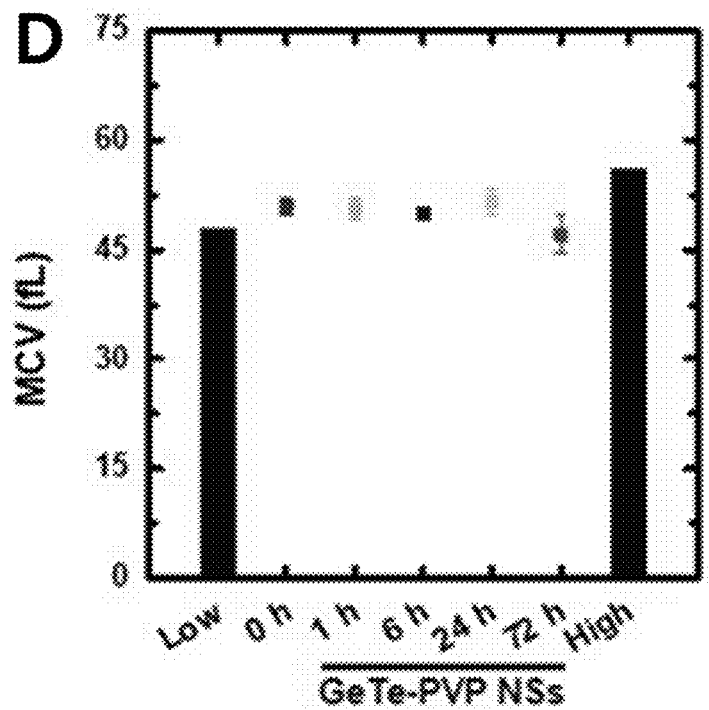
FIG. 27D illustrates the results of analyzing the level of mean corpuscular volume (MCV) in blood after administering a high concentration of GeTe-PVP NS to mice.
Figure 27E:
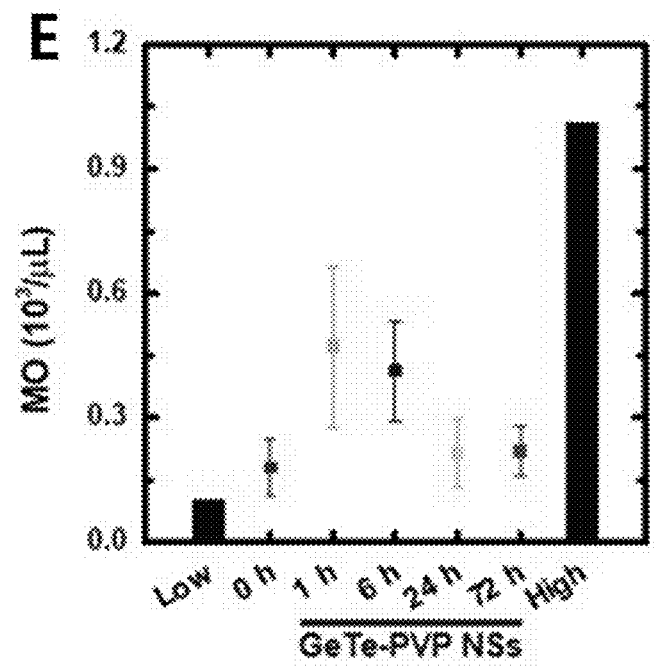
FIG. 27E illustrates the results of analyzing the level of monocytes (MO) in blood after administering a high concentration of GeTe-PVP NS to mice.
Figure 27F:
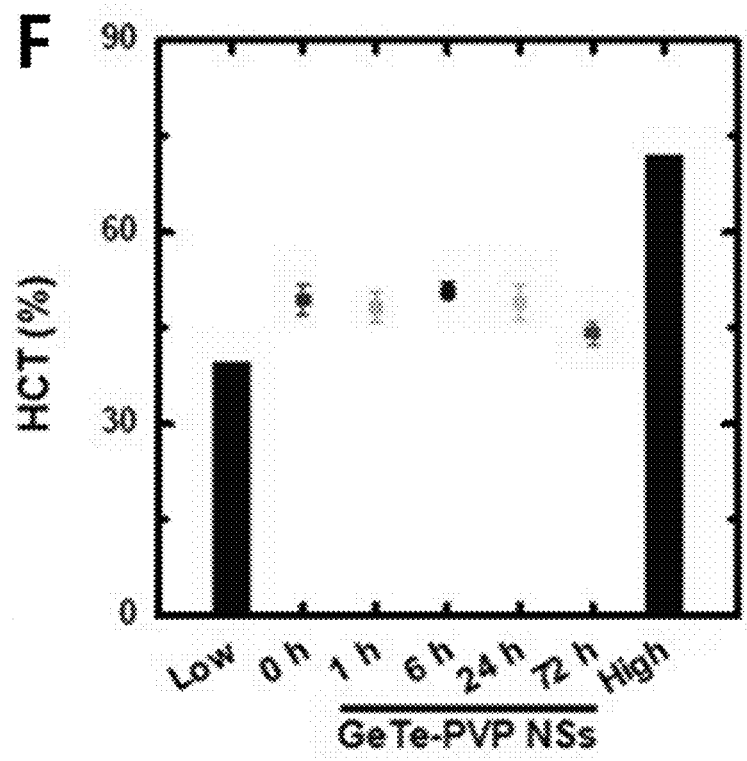
FIG. 27F illustrates the results of analyzing the level of hematocrit (HCT) in blood after administering a high concentration of GeTe-PVP NS to mice.

As a result of histological analysis, it could be confirmed that GeTe-PVP NSs are not toxic while being biocompatible by confirming that there was no abnormality in all the isolated tissues (FIG. 25). It could be seen that all blood analysis results were also within normal ranges (FIGS. 26A-26I and 27A-27F).

Example 11: Confirmation of Psoriasis Therapeutic Effect of GeTe-PVP NSs 11-1. Establishment of Psoriasis Animal Model C57BL/6 mice (7 weeks old, female) were purchased from Orient Bio Inc. (Korea). Mice were sufficiently fed solid food (no antibiotics added) and water until the day of the experiment, and were allowed to adapt to an environment with a temperature of $23\pm2°$ C., a humidity of $55\pm10\%$, and a light-dark cycle of 12-12 hours for one week, and then used for experiments.

As a psoriasis animal model, an imiquimod-induced psoriasis-like inflammation model commonly used in psoriasis research was used. Specifically, aldara cream (5% imiquimod (IMQ)), which is a TLR7 agonist, was applied to the depilated back and ears of mice for 7 days to induce psoriatic inflammatory responses such as scaling, redness, and skin thickening.

11-2. Evaluation of Therapeutic Effect (with Naked Eye)

In order to evaluate the therapeutic effect of GeTe-PVP NSs on psoriasis, the psoriasis animal models of 11-1 above were classified into four groups as shown in the following Table 2. Group 1 is the negative control group, and the same amount of Vaseline as imiquimod was topically applied on the back and ears. Anti-interleukin 17A known to be effective for treating psoriasis was intraperitoneally injected into Group 3. GeTe-PVP NS s were intradermally injected into Group 4.

TABLE 2

| | Denoted | Test material | Dose | Administration date | Administration Method |
|---|---|---|---|---|---|
| Group 1 | NC | Vaseline | Back 60 mg/mouse Ears 40 mg/mouse | 1 to 7 | Skin application |

TABLE 2-continued

| Denoted | Test material | Dose | Administration date | Administration Method |
|---|---|---|---|---|
| Group 2 IMQ | Imiquimod | Back 60 mg/mouse Ears 40 mg/mouse | 1 to 7 | Skin application |
| Group 3 Anti-17A | Anti-IL-17A | 3 mg/kg | 1, 3, 5 | Intraperitoneal injection |
| Group 4 GeTe-PVP NS | GeTe-PVP NS | 2.5 mg/kg | 1, 3, 5 | Intradermal injection |

The efficacy of GeTe-PVP NSs for treating psoriasis was visually evaluated using a psoriasis area severity index (PASI) score, which is the most commonly used evaluation method for clinical evaluation of psoriasis. In the animal model, skin thickness, redness and the degree of scaling were visually evaluated on a scale of 4 points each.

Thickness: the middle part of the skin on the back and the middle part of the right ear were measured using a caliper/the pattern of change was quantified as 0 to 3 points by setting the thickness of the brown skin on the first day of the experiment (Day 1) for each mouse as 100% and expressing the change in thickness as % (0 point: 1 to 5%, 1 point: 5 to 50%, 2 points: 50 to 100%, and 3 points: >100% change)

Redness (erythema): evaluated by visual observation

Scaling: evaluated by visual observation

Erythema and keratin were quantified on a scale of 0 to 3 points (0 point: no symptoms, 1 point: mild, 2 point: moderate, and 3 point: severe).

Figure 28A:
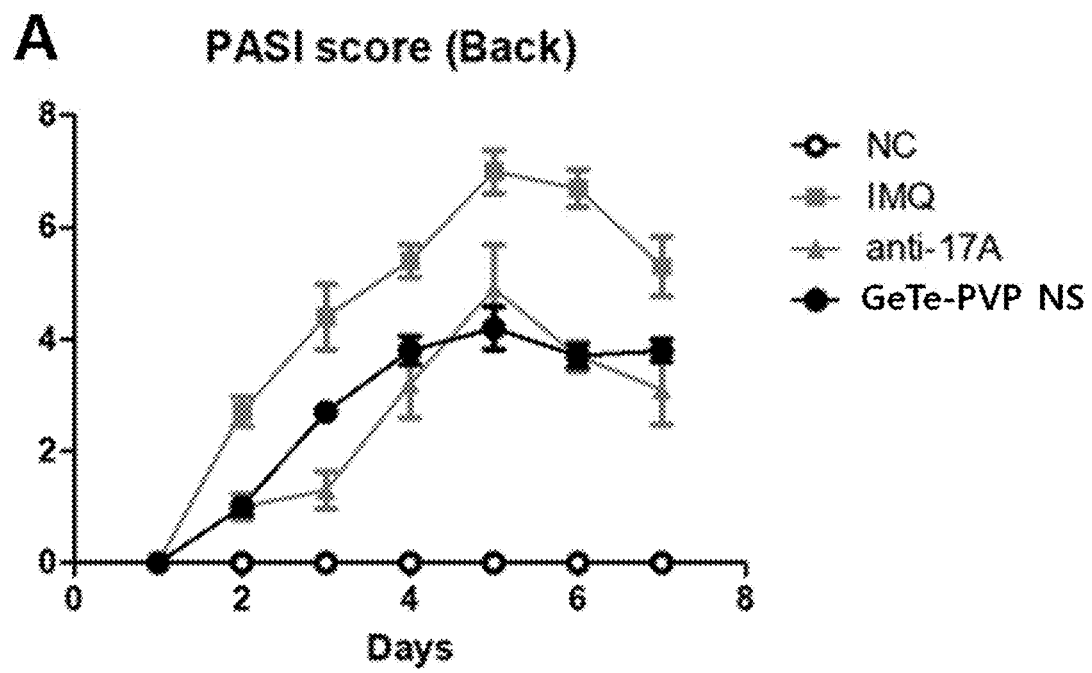
FIG. 28A illustrates the results of confirming the psoriasis area severity index (PASI) after applying or administering each test material to the back of mice: NC=negative control group (petrolatum application); IMQ=induction of psoriasis by applying imiquimod on the back and ears; Anti-17A=psoriasis induction and anti-interleukin 17A administration; and GeTe-PVP NS=psoriasis induction and GeTe-PVP NS administration.
Figure 28B:
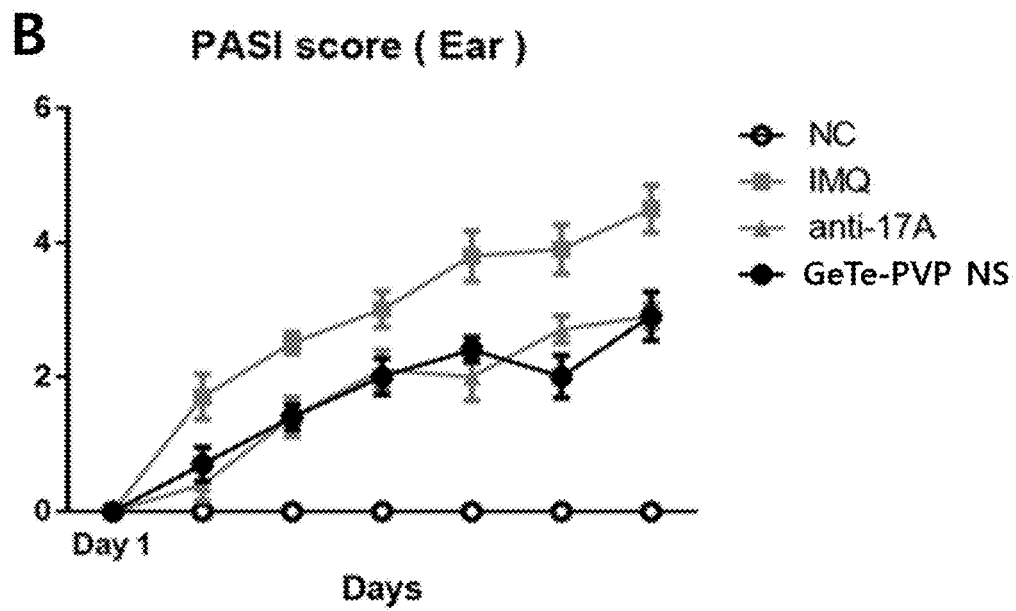
FIG. 28B illustrates the results of confirming the psoriasis area severity index (PASI) after applying or administering each test material to the ears of mice: NC=negative control group (petrolatum application); IMQ=induction of psoriasis by applying imiquimod on the back and ears; Anti-17A=psoriasis induction and anti-interleukin 17A administration; and GeTe-PVP NS=psoriasis induction and GeTe-PVP NS administration.

As a result of the evaluation, it was confirmed that Group 2 (IMQ) had severe inflammatory responses such as scaling, redness, and skin thickening on both the back and ears, and thus psoriasis was well induced. In contrast, it could be seen that Group 3 (anti-17A) administered anti-IL-17A known to treat psoriasis significantly alleviated scaling and redness induced by imiquimod. It could be confirmed that imiquimod-induced redness and skin thickening were also significantly alleviated in Group 4 (GeTe-PVP NSs) (FIGS. 28A and 28B).

11-3. Evaluation of Hematological and Histological Therapeutic Effect

Mice were sacrificed after visual observation was completed on the final day of the experiment. Blood was obtained through cardiac blood collection, and then organs (back, stomach, and spleen) were excised.

Paraffin sections were prepared by fixing back skin and ears in 4% formalin, and then stained with Masson trichrome (MT) and hematoxylin & eosin (H&E). Thereafter, histological evaluation was performed by taking photographs under a microscope. Next, the epidermis thickness was measured by analyzing photographs of stained tissues with the Image J program.

Figure 29:
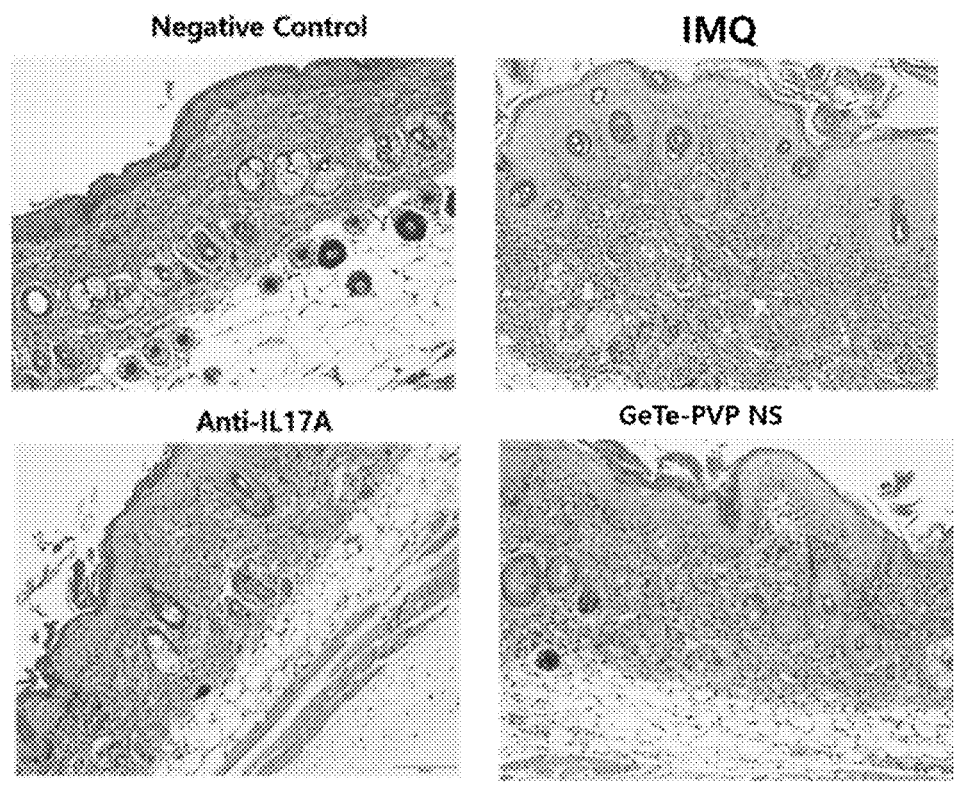
FIG. 29 illustrates the results of isolating tissues and staining them with Masson trichrome after applying or administering each test material to the back and ears of mice: NC=negative control; IMQ=induction of psoriasis by applying imiquimod on the back and ears; Anti-17A=psoriasis induction and anti-interleukin 17A administration; and GeTe-PVP NS=psoriasis induction and GeTe-PVP NS administration.

In MT staining, the red-stained area is the epidermis, and the blue-stained area is the dermis. It could be confirmed that the epidermis was thicker in Group 2 (IMQ) compared to Group 1 (NC), but the thickness of the epidermis was thinner in Group 3 (Anti-17A) and Group 4 (GeTe-PVP NSs) compared to the imiquimod-applied group (FIG. 29).

Figure 30:
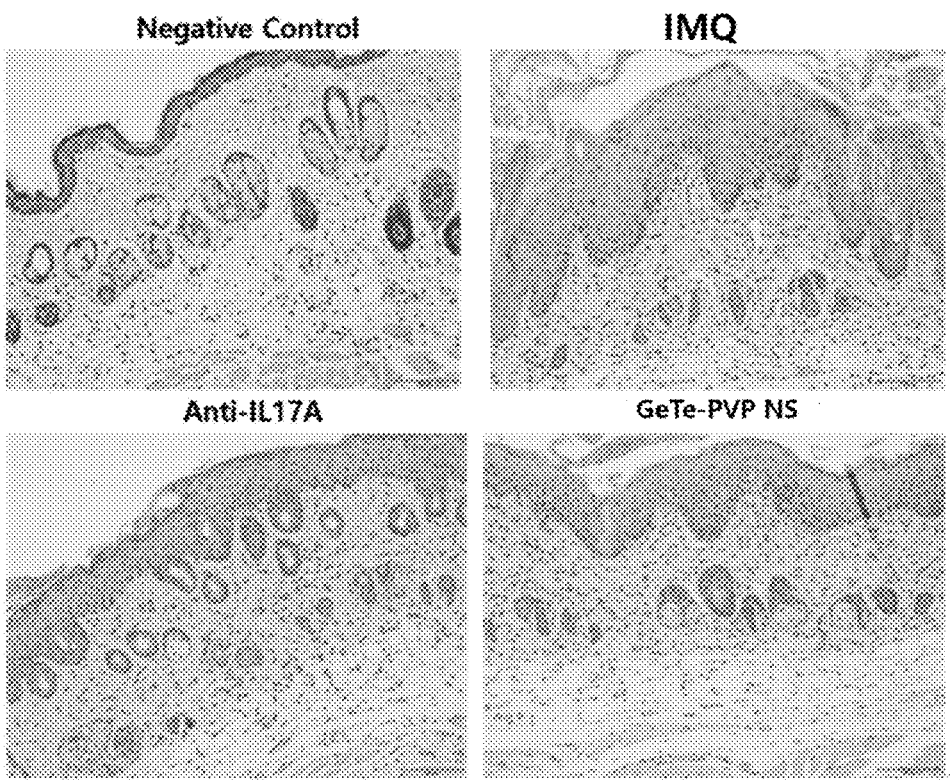
FIG. 30 illustrates the results of isolating tissues and staining them with hematoxylin & eosin after applying or administering each test material to the back and ears of mice: NC=negative control; IMQ=induction of psoriasis by applying imiquimod on the back and ears; Anti-17A=psoriasis induction and anti-interleukin 17A administration; and GeTe-PVP NS=psoriasis induction and GeTe-PVP NS administration.

The same result could be confirmed with H&E staining. In H&E staining, it could be seen that the dark purple-stained area at the top of the tissue is the epidermis, but the epidermis was thicker in Group 2 (IMQ) compared to Group 1 (NC), and inflammatory cells appearing as dots infiltrated the epidermis area to a large extent. In addition, in group 2 (IMQ), many symptoms occurring in psoriasis diseases such as parakeratosis, hyperkeratosis, and microabscesses were observed, indicating that psoriasis was well induced. In contrast, it could be confirmed that in Group 3 (Anti-17A) and Group 4 (GeTe-PVP NSs), the thickness of the epidermis was thinner compared to Group 2 (IMQ), the infiltration of inflammatory cells in the dermis is also reduced, and the pattern of psoriasis diseases appearing in the stratum corneum of the skin, such as parakeratosis, was alleviated (FIG. 30).

The blood was centrifuged at 13,200 rpm for 5 minutes to isolate only plasma (serum). The levels of interleukin-6 (IL-6) and nitric oxide (NO), which are inflammatory cytokines in plasma, were analyzed with ELISA assay.

Figure 31A:
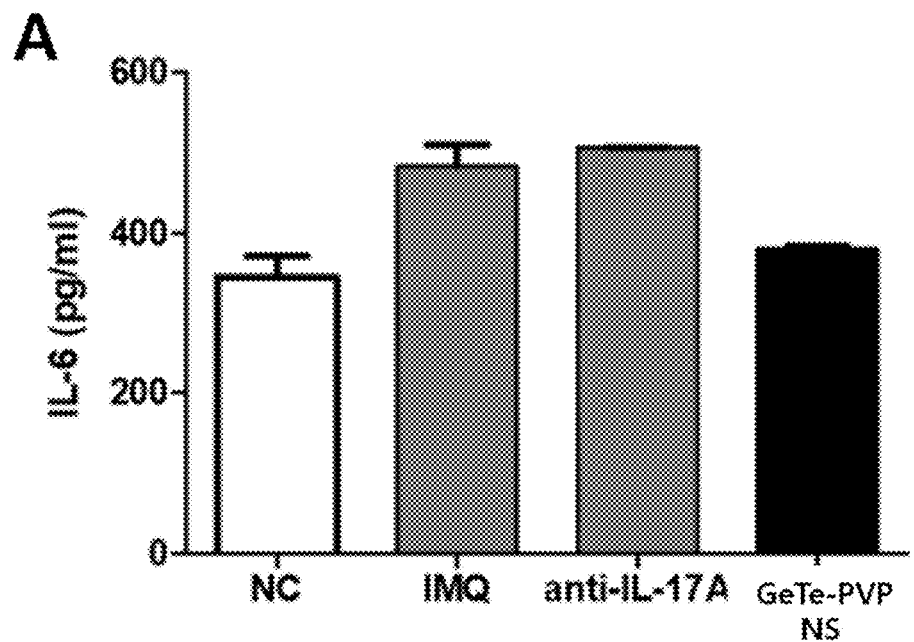
FIG. 31A illustrates the results of isolating blood and confirming the level of IL-6 after applying or administering each test material to the back and ears of mice: NC=negative control; IMQ=induction of psoriasis by applying imiquimod on the back and ears; Anti-17A=psoriasis induction and anti-interleukin 17A administration; and GeTe-PVP NS=psoriasis induction and GeTe-PVP NS administration.
Figure 31B:
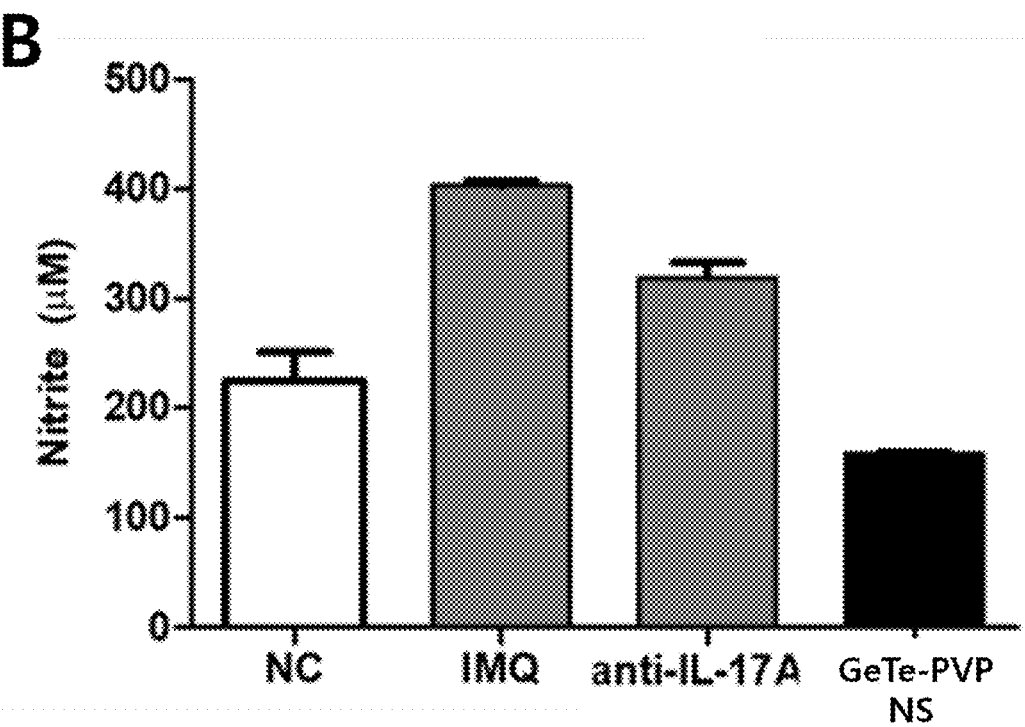
FIG. 31B illustrates the results of isolating blood and confirming the level of nitrite after applying or administering each test material to the back and ears of mice: NC=negative control; IMQ=induction of psoriasis by applying imiquimod on the back and ears; Anti-17A=psoriasis induction and anti-interleukin 17A administration; and GeTe-PVP NS=psoriasis induction and GeTe-PVP NS administration.

As a result of analysis, levels of all inflammatory factors in Group 2 (IMQ) were increased compared to Group 1 (NC). In contrast, levels of inflammatory factors were decreased in Group 3 (Anti-17A) and Group 4 (GeTe-PVP NSs) compared to Group 2 (IMQ). In particular, it could be confirmed that the NO (measured at the level of nitrite) level was significantly reduced in Group 4 (GeTe-PVP NSs) (FIGS. 31A and 31B).

After the excised spleen was ground, splenocytes were obtained through a red blood cell lysis process. After incubation of splenocytes with antibodies specific for each cell, Th1, Th17, and Treg cell populations were analyzed through flow cytometry (Sony). Th1 cells include inflammatory cytokines $CD4^+$, T-bet and IFN-γ positive T cells, and Th17 cells include inflammatory cytokines $CD4^+$, RAR (retinoic acid receptor)—related orphan receptor gamma (RORγ) and IL-17A positive T cells.

Figure 32A:
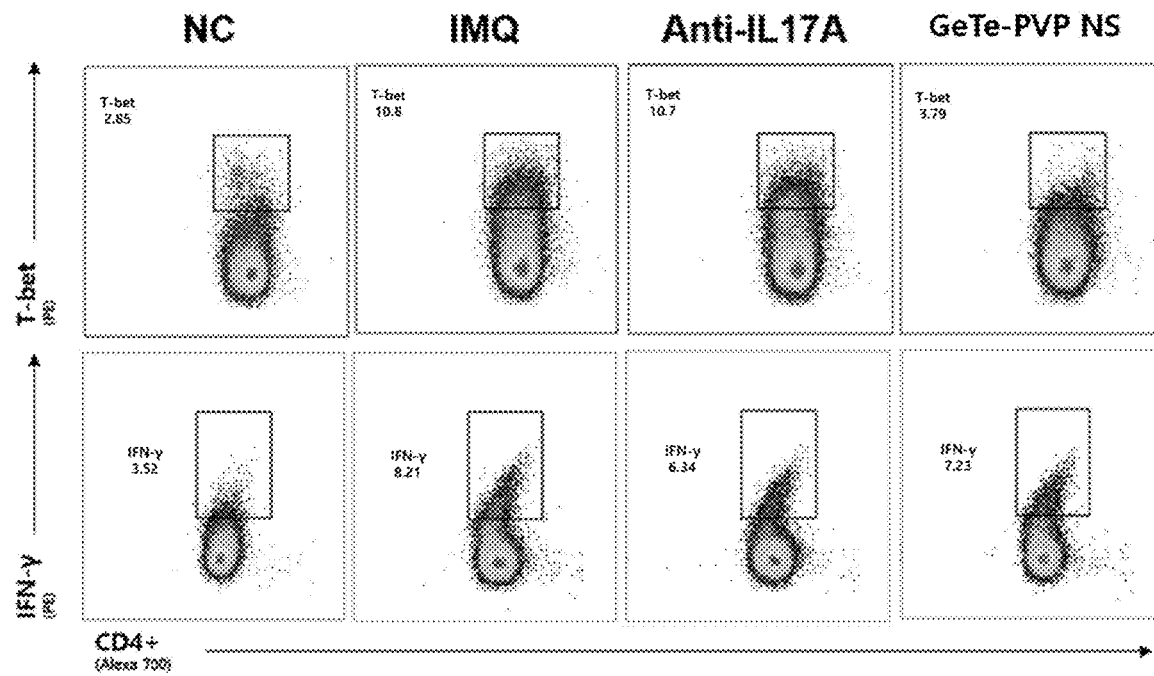
FIG. 32A illustrates the results of isolating spleen cells and confirming Th1 cell populations through flow cytometry after applying or administering each test material to the back and ears of mice: NC=negative control; IMQ=induction of psoriasis by applying imiquimod on the back and ears; Anti-17A=psoriasis induction and anti-interleukin 17A administration; and GeTe-PVP NS=psoriasis induction and GeTe-PVP NS administration.
Figure 32B:
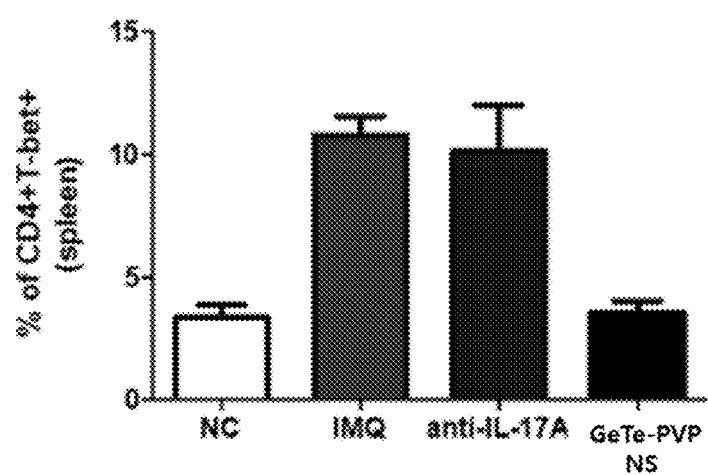
FIG. 32B illustrates the results of isolating spleen cells and confirming the CD4$^+$ T-bet$^+$ T cell populations among Th1 cells after applying or administering each test material to the back and ears of mice: NC=negative control; IMQ=induction of psoriasis by applying imiquimod on the back and ears; Anti-17A=psoriasis induction and anti-interleukin 17A administration; and GeTe-PVP NS=psoriasis induction and GeTe-PVP NS administration.
Figure 32C:
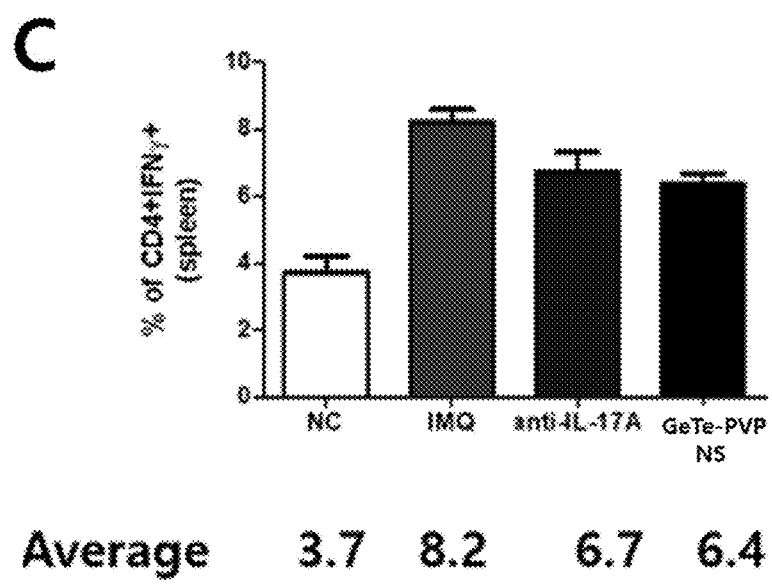
FIG. 32C illustrates the results of isolating spleen cells and confirming the CD4$^+$ IFNγ$^+$ T cell populations among Th1 cells after applying or administering each test material to the back and ears of mice: NC=negative control; IMQ=induction of psoriasis by applying imiquimod on the back and ears; Anti-17A=psoriasis induction and anti-interleukin 17A administration; and GeTe-PVP NS=psoriasis induction and GeTe-PVP NS administration.
Figure 33A:
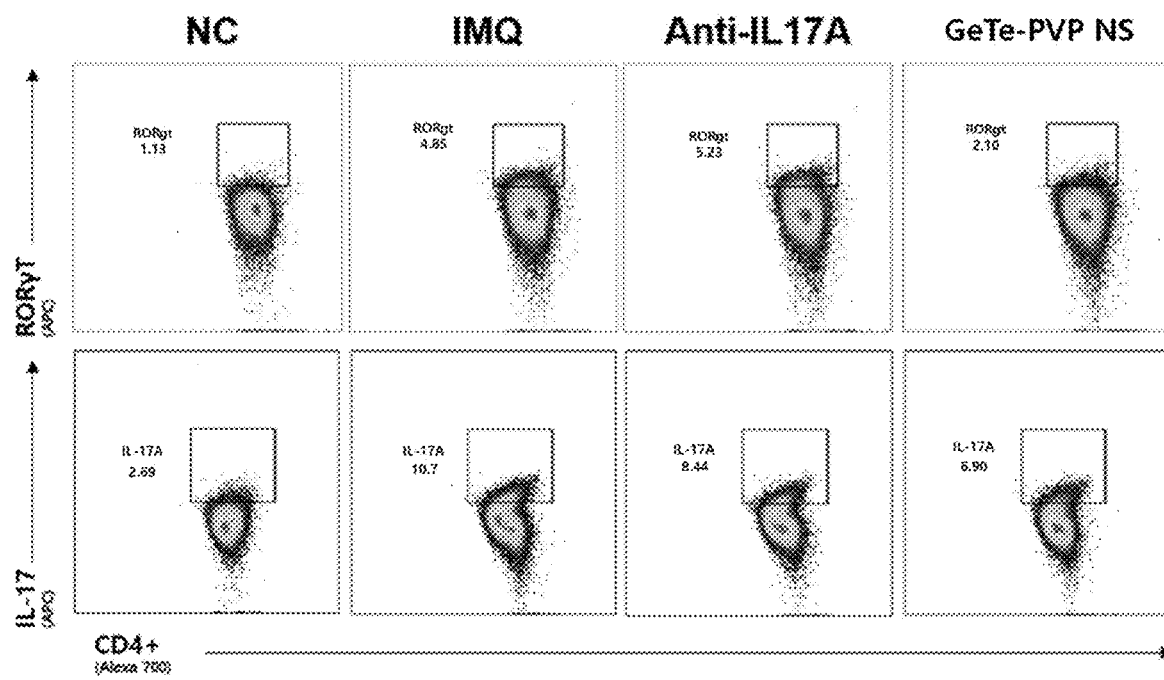
FIG. 33A illustrates the results of isolating spleen cells and confirming Th17 cell populations through flow cytometry after applying or administering each test material to the back and ears of mice: NC=negative control; IMQ=induction of psoriasis by applying imiquimod on the back and ears; Anti-17A=psoriasis induction and anti-interleukin 17A administration; and GeTe-PVP NS=psoriasis induction and GeTe-PVP NS administration.
Figure 33B:
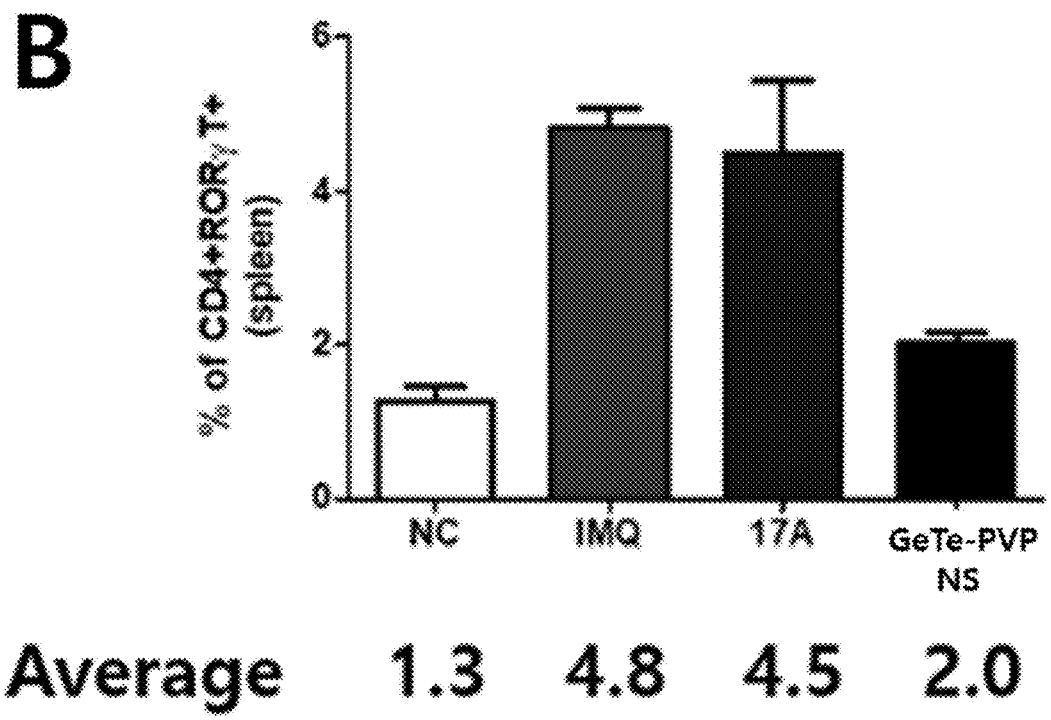
FIG. 33B illustrates the results of isolating spleen cells and confirming the CD4+ RORγ+ T cell populations among Th1 cells after applying or administering each test material to the back and ears of mice: NC=negative control; IMQ=induction of psoriasis by applying imiquimod on the back and ears; Anti-17A=psoriasis induction and anti-interleukin 17A administration; and GeTe-PVP NS=psoriasis induction and GeTe-PVP NS administration.
Figure 33C:
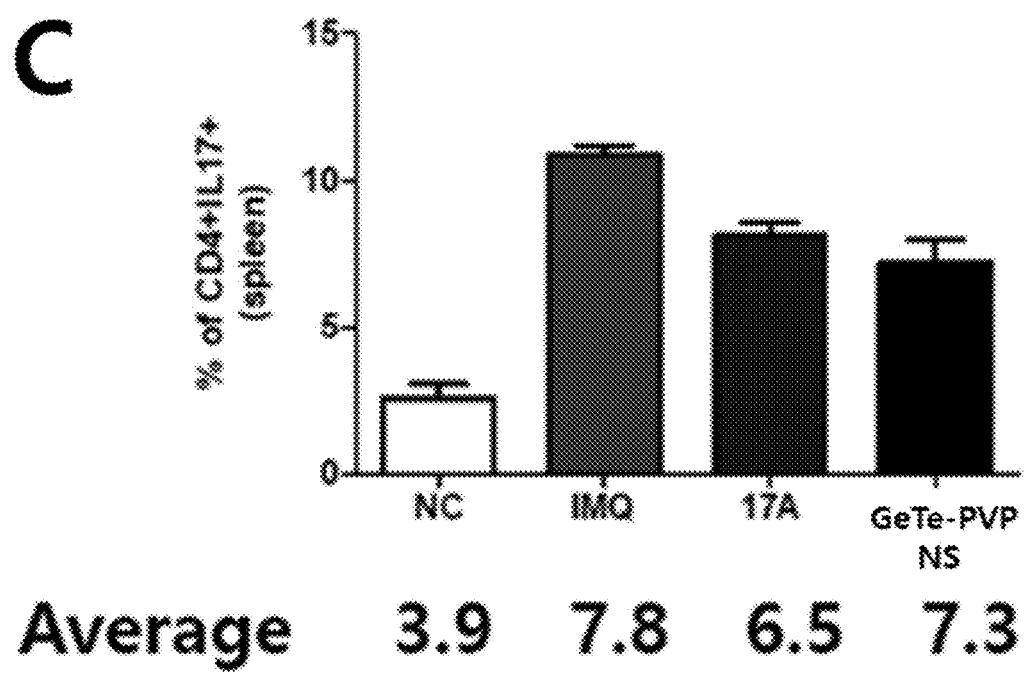
FIG. 33C illustrates the results of isolating spleen cells and confirming the CD4+ IL17+ T cell populations among Th1 cells after applying or administering each test material to the back and ears of mice: NC=negative control; IMQ=induction of psoriasis by applying imiquimod on the back and ears; Anti-17A=psoriasis induction and anti-interleukin 17A administration; and GeTe-PVP NS=psoriasis induction and GeTe-PVP NS administration.

As a result of the analysis, the number of Th1 cells was remarkably increased in Group 2 (IMQ) compared to Group 1 (NC), and slightly decreased in Group 3 (Anti-17A) compared to Group 2 (IMQ). In contrast, it could be seen that in Group 4 (GeTe-PVP NSs), the number of Th1 cells was remarkably reduced (FIGS. 32A, 32B and 32C). Analysis of Th17 cells also showed a similar tendency (FIGS. 33A, 33B and 33C).

Example 12: Evaluation of Inflammatory Therapeutic Effect Using GeTe-PVP NSs and Near-Infrared Rays 12-1. Induction of Inflammation, GeTe-PVP NS and Near-Infrared Treatment RAW264.7 cells were cultured in an incubator at 5% $CO_2$, 95% humidity and 37° C. using DMEM supplemented with 10% FBS and 1% penicillin/streptomycin. Cells were subcultured when they showed a confluence of 70 to 80%.

RAW264.7 cells were seeded in 12-well plates at a density of $3 \times 10^5$ cells/well and cultured for 24 hours as in the existing experiment. Thereafter, the cells were simultaneously treated with 0.5 μg/ml lipopolysaccharide (LPS) and 12.5 μg/ml GeTe-PVPNS and additionally cultured for 24 hours. The next day, the plate was removed, irradiated with a laser at 42° C. for 10 minutes, and incubated in an incubator. After 12 hours, RNA was isolated by harvesting media and cells, and cDNA was synthesized for further experiments.

Figure 34:
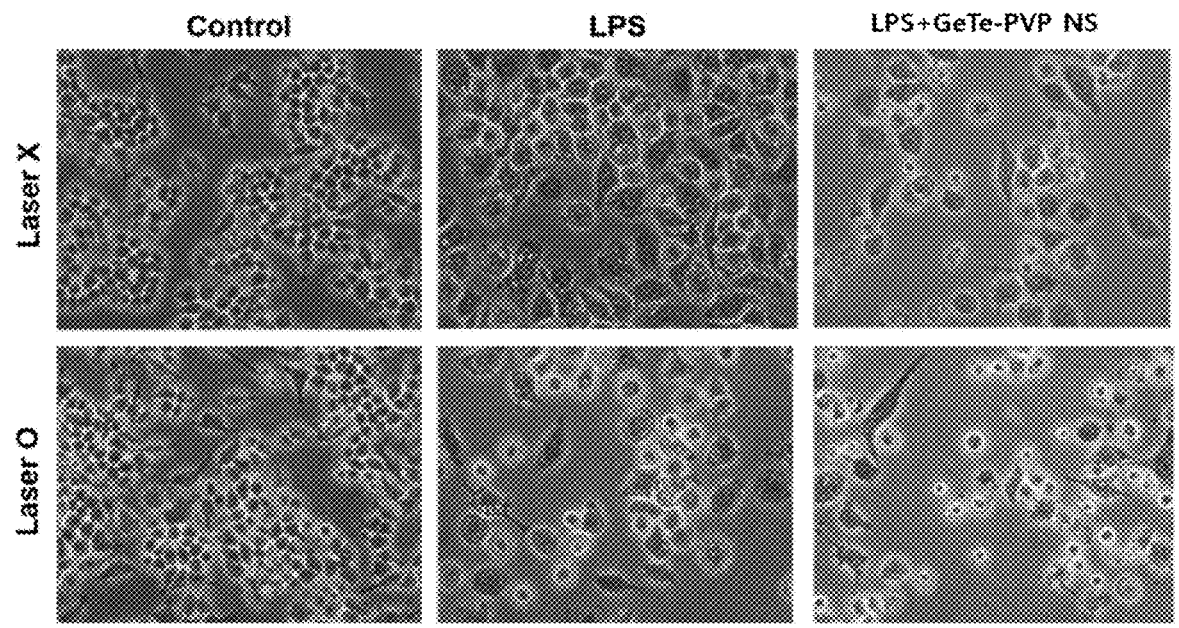
FIG. 34 shows the results of observing cell morphology after treating macrophage cells with LPS and GeTe-PVP NS and irradiating the macrophage cells with laser.

As a result of observing the cell morphology before harvesting the cells, it could be confirmed that there was no change (FIG. 34).

12-2. Evaluation of Inflammatory Therapeutic Effect

Figure 35A:
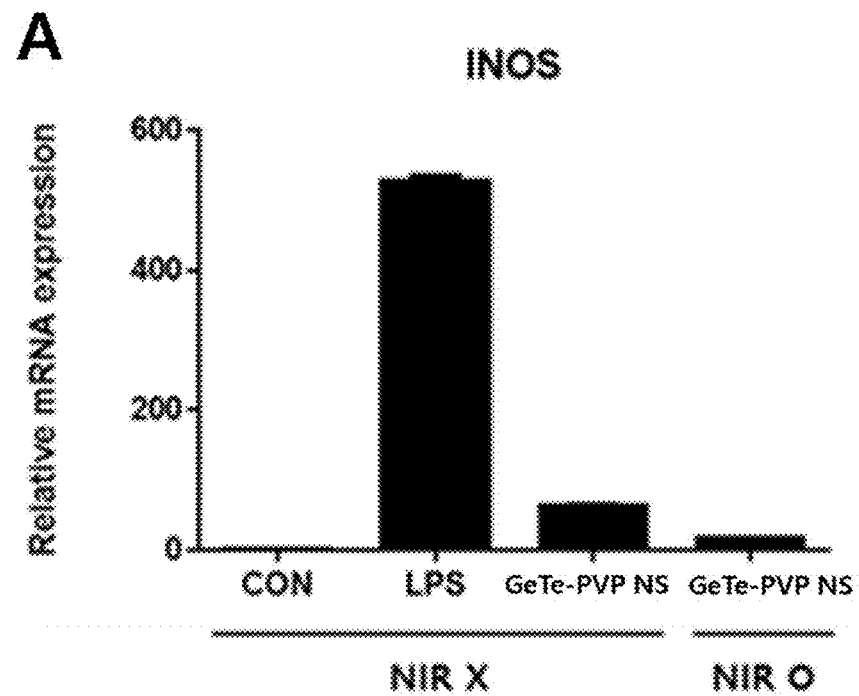
FIG. 35A illustrates the results of confirming the expression change of nitric oxide synthase (INOS) after treating macrophage cells with LPS and GeTe-PVP NS and irradiating the macrophage cells with laser.
Figure 35B:
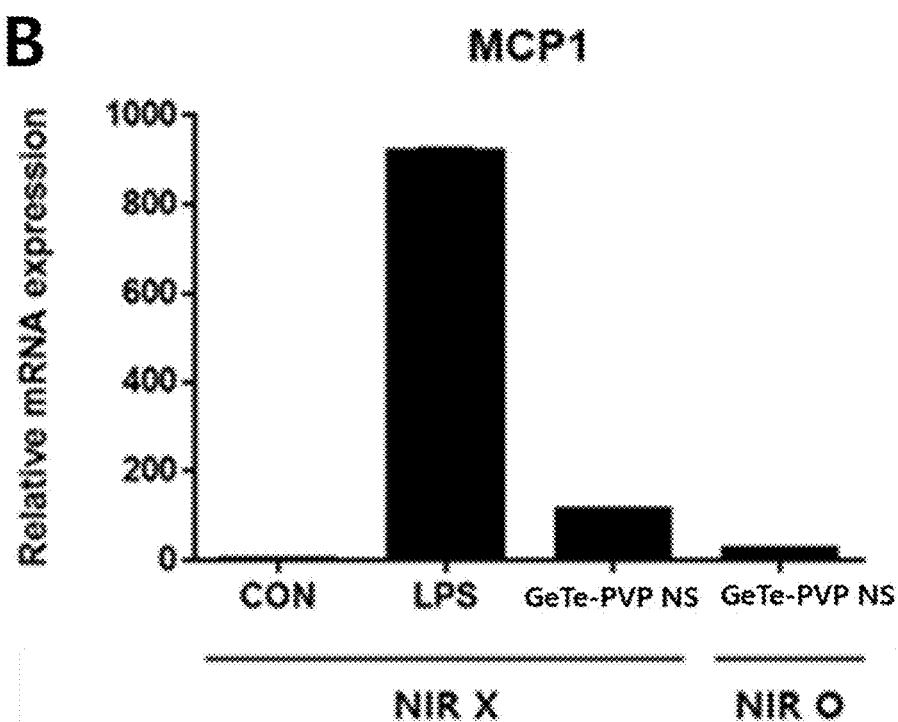
FIG. 35B illustrates the results of confirming the expression change of monocyte chemoattractant protein-1 (MCP-1) after treating macrophage cells with LPS and GeTe-PVP NS and irradiating the macrophage cells with laser.

RT-PCR was performed on the synthesized cDNA to confirm changes in expression of nitric oxide synthase (INOS) and monocyte chemoattractant protein-1 (MCP-1), which are inflammation-promoting materials. As a result, it could be seen that the levels of INOS and MCP-1, which were increased by LPS treatment, were decreased by GeTe-PVPNS treatment, and were further remarkably decreased by near-infrared irradiation (FIGS. 35A and 35B).

It was confirmed through macroscopic, blood, and histological evaluations that GeTe-PVP NSs according to the present invention had a therapeutic effect not only on inflammatory bowel disease but also on psoriasis, which is a systemic inflammatory disease through disease animal models. In addition, through in vitro cell experiments, it could be confirmed that when concurrent administration of GeTe-PVP NS and near-infrared irradiation, the production of inflammation promoting materials was further suppressed. This indicates that when both GeTe-PVP NSs and near-infrared irradiation are applied to treat inflammatory diseases, better therapeutic effects can be obtained.

The germanium telluride nanosheets coated with polyvinylpyrrolidone of the present invention have excellent anti-inflammatory and anticancer activity and absorb light in the ultraviolet to near-infrared region, and thus can be used as a composition for treating inflammatory diseases and cancer and a contrast agent composition.

What is claimed is:

1. A method of treating inflammatory diseases, comprising administering a pharmaceutically effective amount of a pharmaceutical composition to a subject in need thereof, wherein the pharmaceutical composition comprise a single layer of germanium telluride nanosheets coated with polyvinylpyrrolidone as an active ingredient.

2. The method of claim 1, wherein the inflammatory diseases are is one or more diseases selected from the group consisting of inflammatory bowel disease, psoriasis, atopic dermatitis, psoriatic arthritis, rheumatoid arthritis, ankylosing spondylitis and systemic lupus erythematosus.

3. The method of claim 1, wherein the inflammatory bowel diseases are Crohn's disease or ulcerative colitis.

4. The method of claim 1, wherein the nanosheets suppress the expression of pro-inflammatory factors and increases the expression of anti-inflammatory factors.

5. The method of claim 4, wherein the pro-inflammatory factors are is selected from the group consisting inducible nitric oxide synthase (iNOS), tumor necrosis factor-α(TNF-α) and interleukin-1β.

6. The method of claim 4, wherein the anti-inflammatory factors are Arginasel (Arg 1) or cluster of differentiation 206 (CD206).

7. The method of claim 1, wherein the pharmaceutical composition is a formulation for oral or parenteral administration.

* * * * *

UNITED STATES PATENT AND TRADEMARK OFFICE
CERTIFICATE OF CORRECTION

Page 1 of 1

PATENT NO. : 11,896,609 B2
APPLICATION NO. : 17/893937
DATED : February 13, 2024
INVENTOR(S) : Kyung-Hwa Yoo et al.

It is certified that error appears in the above-identified patent and that said Letters Patent is hereby corrected as shown below:

In the Claims

Claim 1, Column 22, Line 5 reads: wherein the pharmaceutical composition comprise a single
Whereas it should read: wherein the pharmaceutical composition comprises a single Claim 2, Column 22, Line 9 reads: diseases are is one or more diseases selected from the group
Whereas it should read: diseases are one or more diseases selected from the group Claim 5, Column 22, Line 20 reads: factors are is selected from the group consisting inducible
Whereas it should read: factors are selected from the group consisting inducible Claim 6, Column 22, Line 24 reads: factors are Arginasel (Arg 1) or cluster of differentiation 206
Whereas it should read: factors are Arginase1 (Arg 1) or cluster of differentiation 206

Signed and Sealed this
Fourth Day of June, 2024

Katherine Kelly Vidal
*Director of the United States Patent and Trademark Office*